US009915613B2

(12) United States Patent
Heinz et al.

(10) Patent No.: US 9,915,613 B2
(45) Date of Patent: Mar. 13, 2018

(54) SYSTEMS AND METHODS FOR DISTINGUISHING OPTICAL SIGNALS OF DIFFERENT MODULATION FREQUENCIES IN AN OPTICAL SIGNAL DETECTOR

(71) Applicant: GEN-PROBE INCORPORATED, San Diego, CA (US)

(72) Inventors: Robert E. Heinz, San Diego, CA (US); Dennis Newell, Fallbrook, CA (US); David Opalsky, San Diego, CA (US); Jason Rhubottom, Oceanside, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 599 days.

(21) Appl. No.: 14/222,160

(22) Filed: Mar. 21, 2014

(65) Prior Publication Data

US 2014/0203189 A1   Jul. 24, 2014

Related U.S. Application Data

(62) Division of application No. 13/404,437, filed on Feb. 24, 2012, now Pat. No. 8,718,948.

(60) Provisional application No. 61/446,280, filed on Feb. 24, 2011.

(51) Int. Cl.
*G01N 33/48* (2006.01)
*G01N 21/64* (2006.01)
*G06G 7/58* (2006.01)

(52) U.S. Cl.
CPC ..... *G01N 21/6486* (2013.01); *G01N 21/6428* (2013.01)

(58) Field of Classification Search
CPC .......... G06F 19/18; G06F 19/20; G06F 19/22; G06F 19/24; G01N 33/582
See application file for complete search history.

(56) References Cited

U.S. PATENT DOCUMENTS

| | | |
|---|---|---|
| 749,104 A | 1/1904 | Schoenefeldt |
| 1,010,016 A | 11/1911 | Campau |
| 2,313,045 A | 3/1943 | Brown |
| 3,504,376 A | 3/1970 | Bendnar et al. |
| 3,562,962 A | 2/1971 | Ohno |
| 3,565,582 A | 2/1971 | Young |
| 3,626,190 A | 12/1971 | Cannon |
| 3,644,095 A | 2/1972 | Netheler et al. |
| 3,663,816 A | 5/1972 | Scherzer et al. |
| 3,676,076 A | 7/1972 | Grady |
| 3,754,444 A | 8/1973 | Ure et al. |
| 3,883,305 A | 5/1975 | Hoskins et al. |
| 3,985,649 A | 10/1976 | Eddleman |
| 4,039,288 A | 8/1977 | Moran |
| 4,054,415 A | 10/1977 | Seligson et al. |
| 4,110,079 A | 8/1978 | Schaeffer et al. |
| 4,169,125 A | 9/1979 | Rodriquez et al. |
| 4,170,625 A | 10/1979 | Welch |
| 4,234,539 A | 11/1980 | Ginsberg et al. |
| 4,235,840 A | 11/1980 | Mendoza et al. |
| 4,268,477 A | 5/1981 | Herzstark |
| 4,276,051 A | 6/1981 | Ginsbert et al. |
| 4,291,230 A | 9/1981 | Heiss |
| 4,298,571 A | 11/1981 | Difulvio et al. |
| 4,305,668 A | 12/1981 | Bilbrey |
| 4,313,735 A | 2/1982 | Yamashita et al. |
| 4,315,891 A | 2/1982 | Sakurada |
| 4,344,768 A | 8/1982 | Parker et al. |
| 4,346,056 A | 8/1982 | Sakurada |
| RE31,108 E | 12/1982 | Ginsberg et al. |
| 4,366,119 A | 12/1982 | Takeuchi |
| RE31,150 E | 2/1983 | Ginsberg et al. |
| 4,451,433 A | 5/1984 | Yamashita et al. |
| 4,459,265 A | 7/1984 | Berglund |
| 4,477,575 A | 10/1984 | Vogel et al. |
| 4,478,095 A | 10/1984 | Bradley et al. |
| 4,479,720 A | 10/1984 | Mochida et al. |
| 4,483,823 A | 11/1984 | Umetsu et al. |
| 4,483,927 A | 11/1984 | Takekawa |
| 4,497,774 A | 2/1985 | Scordato |
| 4,501,164 A | 2/1985 | Stockdale et al. |
| 4,528,159 A | 7/1985 | Liston |
| 4,595,562 A | 6/1986 | Liston et al. |
| 4,612,289 A | 9/1986 | Furuta et al. |
| 4,647,199 A | 3/1987 | Ferber et al. |
| 4,647,432 A | 3/1987 | Wakatake |
| 4,678,752 A | 7/1987 | Thorne et al. |
| 4,683,195 A | 7/1987 | Mullis et al. |
| 4,683,202 A | 7/1987 | Mullis |

(Continued)

FOREIGN PATENT DOCUMENTS

| | | |
|---|---|---|
| CN | 101421598 A | 4/2009 |
| DE | 4128698 A1 | 3/1993 |
| DE | 9405224.7 | 5/1994 |
| EP | 0171140 A2 | 2/1986 |
| EP | 0272055 A2 | 6/1988 |

(Continued)

OTHER PUBLICATIONS

US 5,998,201, 12/1999, Maes et al. (withdrawn)
SIPO Office Action, Chinese Patent Application No. 201280010534.1, dated Feb. 15, 2015.
SIPO Search Report, Chinese Patent Application No. 201280010534.1, dated Feb. 15, 2015.

(Continued)

*Primary Examiner* — Eric S Dejong
(74) *Attorney, Agent, or Firm* — Charles B. Cappellari; David L. Devernoe; Richard Wydeven

(57) ABSTRACT

Systems and method for detecting optical signals, and for discriminating optical signals emitted by an emission moiety that is excited by an associated excitation signal from background signals and other optical noise, employing digital techniques for determining the portion of a detected optical signal having a modulation frequency corresponding to a modulation of the associated excitation signal.

10 Claims, 27 Drawing Sheets

(56) References Cited

U.S. PATENT DOCUMENTS

| | | |
|---|---|---|
| 4,695,430 A | 9/1987 | Coville et al. |
| 4,699,766 A | 10/1987 | Yamashita |
| 4,699,767 A | 10/1987 | Aihara |
| 4,731,225 A | 3/1988 | Wakatake |
| 4,747,693 A | 5/1988 | Kahl |
| 4,755,055 A | 7/1988 | Johnson et al. |
| 4,761,268 A | 8/1988 | Anderson et al. |
| 4,764,342 A | 8/1988 | Kelln et al. |
| 4,774,055 A | 9/1988 | Wakatake et al. |
| 4,781,891 A | 11/1988 | Galle et al. |
| 4,826,660 A | 5/1989 | Smith et al. |
| 4,834,944 A | 5/1989 | Wakatake |
| 4,844,868 A | 7/1989 | Rokugawa |
| 4,848,917 A | 7/1989 | Benin et al. |
| 4,849,176 A | 7/1989 | Sakagami |
| 4,855,110 A | 8/1989 | Marker et al. |
| 4,863,690 A | 9/1989 | Berthold et al. |
| 4,865,986 A | 9/1989 | Coy et al. |
| 4,871,676 A | 10/1989 | Yamada |
| 4,883,644 A | 11/1989 | Perlman |
| 4,895,650 A | 1/1990 | Wang |
| 4,906,433 A | 3/1990 | Minekane |
| 4,908,186 A | 3/1990 | Sakamaki |
| 4,908,320 A | 3/1990 | Zakowski et al. |
| 4,919,887 A | 4/1990 | Wakatake |
| 4,961,906 A | 10/1990 | Anderson et al. |
| 4,965,049 A | 10/1990 | Lillig et al. |
| 4,981,801 A | 1/1991 | Suzuki et al. |
| 5,043,141 A | 8/1991 | Wilson et al. |
| 5,051,238 A | 9/1991 | Umetsu et al. |
| 5,075,079 A | 12/1991 | Kerr et al. |
| 5,082,628 A | 1/1992 | Andreotti et al. |
| 5,084,242 A | 1/1992 | Sakuma et al. |
| 5,086,233 A | 2/1992 | Stafford et al. |
| 5,089,233 A | 2/1992 | Devaney et al. |
| 5,104,231 A | 4/1992 | Collier et al. |
| 5,104,621 A | 4/1992 | Pfost et al. |
| 5,104,807 A | 4/1992 | Mitsumaki et al. |
| 5,104,808 A | 4/1992 | Laska et al. |
| 5,122,343 A | 6/1992 | Ishizaka et al. |
| 5,128,103 A | 7/1992 | Wang et al. |
| 5,128,104 A | 7/1992 | Murphy et al. |
| 5,139,743 A | 8/1992 | Ishizaka et al. |
| 5,139,745 A | 8/1992 | Barr et al. |
| 5,141,871 A | 8/1992 | Kureshy et al. |
| 5,147,610 A | 9/1992 | Watanabe et al. |
| 5,154,888 A | 10/1992 | Zander et al. |
| 5,154,889 A | 10/1992 | Muraishi |
| 5,167,448 A | 12/1992 | Herold et al. |
| 5,183,638 A | 2/1993 | Wakatake |
| 5,186,827 A | 2/1993 | Liberti et al. |
| 5,192,505 A | 3/1993 | Sakagami |
| 5,192,506 A | 3/1993 | Kuresy et al. |
| 5,207,987 A | 5/1993 | Kuresy et al. |
| 5,208,651 A | 5/1993 | Buican |
| 5,213,761 A | 5/1993 | Sakagami |
| 5,215,714 A | 6/1993 | Okada et al. |
| 5,223,218 A | 6/1993 | Fukuoka et al. |
| 5,229,297 A | 7/1993 | Schnipelsky et al. |
| 5,232,665 A | 8/1993 | Burkovich et al. |
| 5,232,669 A | 8/1993 | Pardinas |
| 5,234,665 A | 8/1993 | Ohta et al. |
| 5,240,678 A | 8/1993 | Litsche |
| 5,240,679 A | 8/1993 | Stettler |
| 5,246,665 A | 9/1993 | Tyranski et al. |
| 5,250,261 A | 10/1993 | Porte |
| 5,254,315 A | 10/1993 | Nurse et al. |
| 5,260,028 A | 11/1993 | Astle |
| 5,270,210 A | 12/1993 | Weyrauch et al. |
| 5,277,871 A | 1/1994 | Fuji et al. |
| 5,288,463 A | 2/1994 | Chemelli |
| 5,290,513 A | 3/1994 | Berthold et al. |
| 5,294,404 A | 3/1994 | Grandone et al. |
| 5,306,510 A | 4/1994 | Meltzer |
| 5,314,663 A | 5/1994 | Mimura |
| 5,314,825 A | 5/1994 | Weyrauch et al. |
| 5,316,726 A | 5/1994 | Babson et al. |
| 5,318,914 A | 6/1994 | Matte et al. |
| 5,320,809 A | 6/1994 | Dunn et al. |
| 5,320,966 A | 6/1994 | Mitsumaki et al. |
| 5,324,481 A | 6/1994 | Dunn et al. |
| 5,330,916 A | 7/1994 | Williams et al. |
| 5,332,549 A | 7/1994 | MacIndoe, Jr. |
| 5,340,747 A | 8/1994 | Folen |
| 5,346,303 A | 9/1994 | Heinonen et al. |
| 5,358,691 A | 10/1994 | Clark et al. |
| 5,360,741 A | 11/1994 | Hunnell |
| 5,374,395 A | 12/1994 | Robinson et al. |
| 5,380,666 A | 1/1995 | Wuerschum |
| 5,384,094 A | 1/1995 | Schacher |
| 5,389,339 A | 2/1995 | Petschek et al. |
| 5,397,709 A | 3/1995 | Berndt |
| 5,401,465 A | 3/1995 | Smethers et al. |
| 5,403,711 A | 4/1995 | Walder et al. |
| 5,415,839 A | 5/1995 | Zaun et al. |
| 5,415,840 A | 5/1995 | Sano et al. |
| 5,419,871 A | 5/1995 | Musak et al. |
| 5,422,271 A | 6/1995 | Chen et al. |
| 5,424,212 A | 6/1995 | Pinsl-Ober et al. |
| 5,434,083 A | 7/1995 | Mitsumaki et al. |
| 5,439,646 A | 8/1995 | Tanimizu et al. |
| 5,443,791 A | 8/1995 | Cathcart et al. |
| 5,443,959 A | 8/1995 | Kikuchi et al. |
| 5,445,794 A | 8/1995 | Wihlborg |
| 5,447,687 A | 9/1995 | Lewis et al. |
| 5,451,528 A | 9/1995 | Raymoure et al. |
| 5,460,780 A | 10/1995 | Devaney, Jr. et al. |
| 5,466,574 A | 11/1995 | Liberti et al. |
| 5,470,744 A | 11/1995 | Astle |
| 5,482,834 A | 1/1996 | Gillespie |
| 5,482,839 A | 1/1996 | Ashihara et al. |
| 5,482,861 A | 1/1996 | Clark et al. |
| 5,507,410 A | 4/1996 | Clark et al. |
| 5,525,300 A | 6/1996 | Danssaert et al. |
| 5,527,673 A | 6/1996 | Reinhartz et al. |
| 5,536,471 A | 7/1996 | Clark et al. |
| 5,536,475 A | 7/1996 | Moubayed et al. |
| 5,538,848 A | 7/1996 | Livak et al. |
| 5,538,849 A | 7/1996 | Uematsu et al. |
| 5,548,826 A | 8/1996 | Sayers |
| 5,558,839 A | 9/1996 | Matte et al. |
| 5,567,595 A | 10/1996 | Kok |
| 5,571,325 A | 11/1996 | Ueyama et al. |
| 5,571,481 A | 11/1996 | Powell et al. |
| 5,575,976 A | 11/1996 | Choperena et al. |
| 5,576,215 A | 11/1996 | Burns et al. |
| 5,578,269 A | 11/1996 | Yaremko et al. |
| 5,578,270 A | 11/1996 | Reichler et al. |
| 5,580,524 A | 12/1996 | Forrest et al. |
| 5,582,796 A | 12/1996 | Carey et al. |
| 5,585,068 A | 12/1996 | Panetz et al. |
| 5,587,129 A | 12/1996 | Kurosaki et al. |
| 5,595,707 A | 1/1997 | Copeland et al. |
| 5,599,501 A | 2/1997 | Carey et al. |
| 5,605,665 A | 2/1997 | Clark et al. |
| 5,610,069 A | 3/1997 | Clark et al. |
| 5,620,898 A | 4/1997 | Yaremko et al. |
| 5,635,364 A | 6/1997 | Clark et al. |
| 5,637,275 A | 6/1997 | Carey et al. |
| 5,639,425 A | 6/1997 | Komiyama et al. |
| 5,639,668 A | 6/1997 | Neel et al. |
| 5,646,049 A | 7/1997 | Tayi |
| 5,652,149 A | 7/1997 | Mileaf et al. |
| 5,653,940 A | 8/1997 | Carey et al. |
| 5,656,493 A | 8/1997 | Mullis et al. |
| 5,658,532 A | 8/1997 | Kurosaki et al. |
| 5,658,799 A | 8/1997 | Choperena et al. |
| 5,670,114 A | 9/1997 | Sakazume et al. |
| 5,670,120 A | 9/1997 | Degenhardt et al. |
| 5,670,375 A | 9/1997 | Seaton et al. |
| 5,677,188 A | 10/1997 | Mitsumaki et al. |
| 5,679,309 A | 10/1997 | Bell |
| 5,681,530 A | 10/1997 | Kuster et al. |
| 5,686,046 A | 11/1997 | Malek et al. |

(56) References Cited

U.S. PATENT DOCUMENTS

| | | | |
|---|---|---|---|
| 5,691,146 A | 11/1997 | Mayrand |
| 5,693,292 A | 12/1997 | Choperena et al. |
| 5,698,450 A | 12/1997 | Ringrose et al. |
| 5,702,950 A | 12/1997 | Tajima |
| 5,705,062 A | 1/1998 | Knobel |
| 5,714,380 A | 2/1998 | Neri et al. |
| 5,716,583 A | 2/1998 | Smethers et al. |
| 5,720,377 A | 2/1998 | Lapeus et al. |
| 5,720,923 A | 2/1998 | Haff et al. |
| 5,730,938 A | 3/1998 | Carbonari et al. |
| 5,730,939 A | 3/1998 | Kurumada et al. |
| 5,736,105 A | 4/1998 | Astle |
| 5,736,106 A | 4/1998 | Ishiguro et al. |
| 5,738,827 A | 4/1998 | Marquiss |
| 5,741,461 A | 4/1998 | Takahashi et al. |
| 5,746,977 A | 5/1998 | Imai et al. |
| 5,746,978 A | 5/1998 | Beinhaus et al. |
| 5,750,338 A | 5/1998 | Collins et al. |
| 5,762,872 A | 6/1998 | Büler et al. |
| 5,762,873 A | 6/1998 | Fanning et al. |
| 5,773,268 A | 6/1998 | Korenberg et al. |
| 5,773,662 A | 6/1998 | Imai et al. |
| 5,779,981 A | 7/1998 | Danssaert et al. |
| 5,784,157 A | 7/1998 | Gorfinkel et al. |
| 5,786,182 A | 7/1998 | Catanzariti et al. |
| 5,789,252 A | 8/1998 | Fujita et al. |
| 5,795,547 A | 8/1998 | Moser et al. |
| 5,795,784 A | 8/1998 | Arnquist et al. |
| 5,800,989 A | 9/1998 | Linn et al. |
| 5,807,523 A | 9/1998 | Watts et al. |
| 5,814,277 A | 9/1998 | Bell et al. |
| 5,826,129 A | 10/1998 | Hasebe et al. |
| 5,827,478 A | 10/1998 | Carey et al. |
| 5,827,479 A | 10/1998 | Yamazaki et al. |
| 5,827,653 A | 10/1998 | Sammes et al. |
| 5,837,195 A | 11/1998 | Malek et al. |
| 5,843,376 A | 12/1998 | Ishihara et al. |
| 5,846,491 A | 12/1998 | Choperena et al. |
| 5,849,247 A | 12/1998 | Uzan et al. |
| 5,855,847 A | 1/1999 | Oonuma et al. |
| 5,863,506 A | 1/1999 | Farren |
| 5,876,668 A | 3/1999 | Kawashima et al. |
| 5,876,930 A | 3/1999 | Livak et al. |
| 5,882,594 A | 3/1999 | Kawaguchi et al. |
| 5,882,596 A | 3/1999 | Breeser et al. |
| 5,882,918 A | 3/1999 | Goffe |
| 5,885,353 A | 3/1999 | Strodtbeck et al. |
| 5,885,529 A | 3/1999 | Babson et al. |
| 5,885,530 A | 3/1999 | Babson et al. |
| 5,888,454 A | 3/1999 | Leistner et al. |
| 5,897,783 A | 4/1999 | Howe et al. |
| 5,919,622 A | 7/1999 | Macho et al. |
| 5,928,869 A | 7/1999 | Nadeau et al. |
| 5,935,791 A | 8/1999 | Nadeau et al. |
| 5,948,691 A | 9/1999 | Ekiriwang et al. |
| 5,958,763 A | 9/1999 | Goffe |
| 5,985,670 A | 11/1999 | Markin |
| 5,985,671 A | 11/1999 | Leistner et al. |
| 5,985,672 A | 11/1999 | Kegelman et al. |
| 5,988,869 A | 11/1999 | Davidson et al. |
| 5,994,056 A | 11/1999 | Higuchi |
| 6,027,691 A | 2/2000 | Watts et al. |
| 6,033,574 A | 3/2000 | Siddiqi |
| 6,033,880 A | 3/2000 | Haff et al. |
| 6,042,786 A | 3/2000 | Oonuma et al. |
| 6,043,506 A | 3/2000 | Heffelfinger et al. |
| 6,043,880 A | 3/2000 | Andrews et al. |
| 6,051,101 A | 4/2000 | Ohtani et al. |
| 6,056,923 A | 5/2000 | Diamond et al. |
| 6,066,455 A | 5/2000 | Kruse-Mueller et al. |
| 6,068,978 A | 5/2000 | Zaun et al. |
| 6,071,395 A | 6/2000 | Lange |
| 6,086,827 A | 7/2000 | Horner et al. |
| 6,096,272 A | 8/2000 | Clark et al. |
| 6,103,193 A | 8/2000 | Iwahashi et al. |
| 6,110,676 A | 8/2000 | Coull et al. |
| 6,110,678 A | 8/2000 | Weisburg et al. |
| 6,117,392 A | 9/2000 | Hanawa et al. |
| 6,117,398 A | 9/2000 | Bienhaus et al. |
| 6,117,683 A | 9/2000 | Kodama et al. |
| 6,124,138 A | 9/2000 | Woudenberg et al. |
| 6,126,899 A | 10/2000 | Woudenberg et al. |
| 6,129,428 A | 10/2000 | Helwig et al. |
| 6,139,800 A | 10/2000 | Chandler |
| 6,140,054 A | 10/2000 | Wittwer et al. |
| 6,143,578 A | 11/2000 | Bendele et al. |
| 6,146,592 A | 11/2000 | Kawashima |
| 6,156,565 A | 12/2000 | Maes et al. |
| 6,165,778 A | 12/2000 | Kedar |
| 6,180,408 B1 | 1/2001 | Kwok et al. |
| 6,193,892 B1 | 2/2001 | Krueger et al. |
| 6,214,293 B1 | 4/2001 | Pantoliano et al. |
| 6,251,660 B1 | 6/2001 | Muir et al. |
| 6,277,332 B1 | 8/2001 | Sucholeiki |
| 6,300,068 B1 | 10/2001 | Berg et al. |
| 6,300,138 B1 | 10/2001 | Gleason et al. |
| 6,335,166 B1 | 1/2002 | Ammann et al. |
| 6,340,598 B1 | 1/2002 | Herron et al. |
| 6,346,384 B1 | 2/2002 | Poliner |
| 6,355,934 B1 | 3/2002 | Osgood et al. |
| 6,369,893 B1 | 4/2002 | Christel et al. |
| 6,377,342 B1 | 4/2002 | Coeurveille |
| 6,379,888 B1 | 4/2002 | Nadeau et al. |
| 6,387,621 B1 | 5/2002 | Wittwer |
| 6,396,581 B1 | 5/2002 | Hayashi et al. |
| 6,399,952 B1 | 6/2002 | Maher et al. |
| 6,409,925 B1 | 6/2002 | Gombinsky et al. |
| 6,410,235 B1 | 6/2002 | Weindel et al. |
| 6,426,230 B1 | 7/2002 | Feistel |
| 6,436,349 B1 | 8/2002 | Carey et al. |
| 6,440,725 B1 | 8/2002 | Pourhamadi et al. |
| 6,472,156 B1 | 10/2002 | Wittwer et al. |
| 6,503,751 B2 | 1/2003 | Hugh |
| 6,517,777 B2 | 2/2003 | Liljestrand et al. |
| 6,517,782 B1 | 2/2003 | Horner et al. |
| 6,517,783 B2 | 2/2003 | Horner et al. |
| 6,577,580 B2 | 6/2003 | Haga |
| 6,586,234 B1 | 7/2003 | Burg et al. |
| 6,597,450 B1 | 7/2003 | Andrews et al. |
| 6,605,213 B1 | 8/2003 | Ammann et al. |
| 6,617,138 B1 | 9/2003 | Rudi et al. |
| 6,699,661 B1 | 3/2004 | Kurane et al. |
| 6,730,501 B2 | 5/2004 | Eyre et al. |
| 6,764,649 B2 | 7/2004 | Ammann |
| 6,790,623 B2 | 9/2004 | Weindel et al. |
| 6,815,164 B2 | 11/2004 | Kurn |
| 6,818,437 B1 | 11/2004 | Gambini et al. |
| 6,825,921 B1 | 11/2004 | Modlin et al. |
| 6,852,986 B1 | 2/2005 | Lee et al. |
| 6,890,742 B2 | 5/2005 | Ammann et al. |
| 6,902,900 B2 | 6/2005 | Davies et al. |
| 6,919,058 B2 | 7/2005 | Andersson et al. |
| 6,919,175 B1 | 7/2005 | Beinhaus et al. |
| 6,929,779 B2 | 8/2005 | Amirkhanian |
| 6,940,598 B2 | 9/2005 | Christel et al. |
| 6,943,029 B2 | 9/2005 | Copeland et al. |
| 6,961,948 B2 | 11/2005 | Seki et al. |
| 7,015,484 B2 | 3/2006 | Gillispie et al. |
| 7,033,820 B2 | 4/2006 | Ammann et al. |
| 7,081,226 B1 | 7/2006 | Wittwer et al. |
| 7,081,339 B2 | 7/2006 | Siepnev |
| 7,087,414 B2 | 8/2006 | Gerdes et al. |
| 7,109,495 B2 | 9/2006 | Lee et al. |
| 7,115,384 B2 | 10/2006 | Clark et al. |
| 7,118,892 B2 | 10/2006 | Ammann et al. |
| 7,118,982 B2 | 10/2006 | Govyadinov et al. |
| 7,135,145 B2 | 11/2006 | Ammann et al. |
| 7,183,084 B2 | 2/2007 | Jaeger |
| 7,190,457 B2 | 3/2007 | Tabacco et al. |
| 7,214,544 B2 | 5/2007 | Poirier et al. |
| 7,220,385 B2 | 5/2007 | Blecka et al. |
| 7,252,937 B2 | 8/2007 | Kaltenboeck |
| 7,261,859 B2 | 8/2007 | Andersson et al. |
| 7,262,008 B2 | 8/2007 | Catanzariti et al. |

(56) References Cited

U.S. PATENT DOCUMENTS

| | | |
|---|---|---|
| 7,267,795 B2 | 9/2007 | Ammann et al. |
| 7,267,945 B2 | 9/2007 | Baskin et al. |
| 7,273,749 B1 | 9/2007 | Wittwer et al. |
| 7,276,368 B2 | 10/2007 | Saaski |
| 7,331,511 B2 | 2/2008 | Corson et al. |
| 7,354,707 B2 | 4/2008 | Kurane et al. |
| 7,373,253 B2 | 5/2008 | Eyre |
| 7,384,600 B2 | 6/2008 | Burns et al. |
| 7,390,459 B2 | 6/2008 | Lebl et al. |
| 7,396,509 B2 | 7/2008 | Burns |
| 7,498,164 B2 | 3/2009 | Oldham et al. |
| 7,508,498 B2 | 3/2009 | Huang et al. |
| 7,560,255 B2 | 7/2009 | Ammann et al. |
| 7,635,588 B2 | 12/2009 | King et al. |
| 7,794,659 B2 | 9/2010 | Lair et al. |
| 7,839,507 B2 | 11/2010 | Gunstream et al. |
| 7,897,337 B2 | 3/2011 | Macioszek et al. |
| 7,932,081 B2 | 4/2011 | Lair et al. |
| 7,964,413 B2 | 6/2011 | Macioszek et al. |
| 8,008,066 B2 | 8/2011 | Lair et al. |
| 8,264,687 B2 | 9/2012 | Lundquist et al. |
| 8,451,775 B2 | 5/2013 | Choi et al. |
| 8,663,922 B2 | 3/2014 | Hayes et al. |
| 8,718,948 B2 | 5/2014 | Heinz et al. |
| 2001/0033374 A1 | 10/2001 | Hoyt |
| 2002/0031446 A1 | 3/2002 | Friedlander et al. |
| 2002/0031768 A1 | 3/2002 | McMillan et al. |
| 2002/0062061 A1 | 5/2002 | Kaneko et al. |
| 2002/0064867 A1 | 5/2002 | Clark et al. |
| 2002/0086417 A1 | 7/2002 | Chen et al. |
| 2002/0090320 A1 | 7/2002 | Burow et al. |
| 2002/0123156 A1 | 9/2002 | Tajima |
| 2002/0137039 A1 | 9/2002 | Gessner |
| 2002/0155619 A1 | 10/2002 | Kurihara et al. |
| 2002/0197611 A1 | 12/2002 | Chagovetz |
| 2003/0058440 A1 | 3/2003 | Scott et al. |
| 2003/0064507 A1 | 4/2003 | Gallagher et al. |
| 2003/0087240 A1 | 5/2003 | Whitcombe |
| 2003/0087397 A1 | 5/2003 | Klein et al. |
| 2003/0129614 A1 | 7/2003 | Parameswaran et al. |
| 2004/0014202 A1 | 1/2004 | King et al. |
| 2004/0033518 A1 | 2/2004 | Wittwer et al. |
| 2004/0076983 A1 | 4/2004 | Karisen |
| 2004/0125377 A1 | 7/2004 | Huang et al. |
| 2004/0223878 A1 | 11/2004 | Chen |
| 2004/0245350 A1 | 12/2004 | Zeng |
| 2005/0064582 A1 | 3/2005 | Wittwer et al. |
| 2005/0123445 A1 | 6/2005 | Blecka et al. |
| 2005/0220669 A1 | 10/2005 | Malyarov et al. |
| 2005/0220670 A1 | 10/2005 | Palmieri et al. |
| 2005/0225745 A1 | 10/2005 | Nagai |
| 2005/0244308 A1 | 11/2005 | Tanaami et al. |
| 2006/0014494 A1 | 1/2006 | Vanderperren et al. |
| 2006/0030038 A1 | 2/2006 | Taylor et al. |
| 2006/0090800 A1 | 5/2006 | Banerjee et al. |
| 2006/0141539 A1 | 6/2006 | Taylor |
| 2006/0166233 A1 | 7/2006 | Wu et al. |
| 2006/0177850 A1 | 8/2006 | Schermer et al. |
| 2006/0275852 A1 | 12/2006 | Montagu et al. |
| 2007/0004028 A1 | 1/2007 | Lair et al. |
| 2007/0087362 A1 | 4/2007 | Church et al. |
| 2007/0098594 A1 | 5/2007 | Elkin et al. |
| 2007/0248958 A1 | 10/2007 | Jovanovich et al. |
| 2008/0171383 A1 | 7/2008 | Selker et al. |
| 2008/0259336 A1 | 10/2008 | Konno et al. |
| 2009/0021728 A1 | 1/2009 | Heinz et al. |
| 2009/0130658 A1 | 5/2009 | Barlag et al. |
| 2009/0134046 A1 | 5/2009 | Breidenthal et al. |
| 2009/0136913 A1 | 5/2009 | Breidenthal et al. |
| 2009/0136963 A1 | 5/2009 | Breidenthal et al. |
| 2009/0137029 A1 | 5/2009 | Breidenthal et al. |
| 2009/0139992 A1 | 6/2009 | Breidenthal et al. |
| 2009/0142745 A1 | 6/2009 | Breidenthal et al. |
| 2009/0142771 A1 | 6/2009 | Breidenthal et al. |
| 2009/0208072 A1 | 8/2009 | Seibel et al. |
| 2010/0075336 A1 | 3/2010 | Knight et al. |
| 2010/0240063 A1 | 9/2010 | Hayes et al. |

FOREIGN PATENT DOCUMENTS

| | | |
|---|---|---|
| EP | 0293782 A1 | 12/1988 |
| EP | 0295526 A1 | 12/1988 |
| EP | 0336309 A2 | 10/1989 |
| EP | 0409126 A2 | 1/1991 |
| EP | 0411620 A2 | 2/1991 |
| EP | 0435481 A2 | 7/1991 |
| EP | 0458138 A2 | 11/1991 |
| EP | 0502638 A2 | 9/1992 |
| EP | 0513618 A2 | 11/1992 |
| EP | 0525577 A2 | 2/1993 |
| EP | 0542422 A1 | 5/1993 |
| EP | 0569214 A2 | 11/1993 |
| EP | 0571033 A1 | 11/1993 |
| EP | 0628824 A1 | 12/1994 |
| EP | 0640828 B1 | 3/1995 |
| EP | 0136126 A2 | 4/1995 |
| EP | 0885958 A1 | 12/1998 |
| EP | 0 997 728 A2 | 5/2000 |
| EP | 1024355 A1 | 8/2000 |
| EP | 1063512 A2 | 12/2000 |
| EP | 1138784 A2 | 10/2001 |
| EP | 1179585 A2 | 2/2002 |
| EP | 1547686 A1 | 6/2005 |
| EP | 2 348 320 A2 | 7/2011 |
| GB | 2081118 A | 2/1982 |
| GB | 2131168 A | 6/1984 |
| JP | 57171266 | 4/1981 |
| JP | 60-241884 A | 11/1985 |
| JP | 61-274697 A | 12/1986 |
| JP | 62-000863 | 1/1987 |
| JP | 62-44663 | 2/1987 |
| JP | 63003265 | 1/1988 |
| JP | 02-66461 | 3/1990 |
| JP | 03-007571 A | 1/1991 |
| JP | 03-105251 A2 | 5/1991 |
| JP | 3-502167 A | 5/1991 |
| JP | 04-328467 A | 11/1992 |
| JP | 4-359154 | 12/1992 |
| JP | 05-10957 | 1/1993 |
| JP | 5-317030 A | 12/1993 |
| JP | 6-197797 | 7/1994 |
| JP | 6-509647 A | 10/1994 |
| JP | 07-75544 A | 3/1995 |
| JP | 7-501933 A | 3/1995 |
| JP | 7/107975 A2 | 4/1995 |
| JP | 7/107999 A2 | 4/1995 |
| JP | 7-191042 A | 7/1995 |
| JP | 7-506184 A | 7/1995 |
| JP | 8-9957 A | 1/1996 |
| JP | 8/320274 A | 12/1996 |
| JP | 9-224644 | 2/1997 |
| JP | 9-503660 A | 4/1997 |
| JP | 9-121899 A | 5/1997 |
| JP | 9-504428 A | 5/1997 |
| JP | 9-504610 A | 5/1997 |
| JP | 11-503315 A | 3/1999 |
| JP | 2000-500331 A | 1/2000 |
| JP | 2000-214090 A | 8/2000 |
| JP | 2001-503730 A | 3/2001 |
| JP | 2002-513936 A | 5/2002 |
| JP | 2004-520574 A | 7/2004 |
| JP | 2007-504477 A | 3/2007 |
| JP | 2007-143407 A | 6/2007 |
| JP | 2008-532526 A | 8/2008 |
| WO | WO 90/008840 A1 | 8/1990 |
| WO | WO 90/09575 A1 | 8/1990 |
| WO | WO 9115768 A1 | 10/1991 |
| WO | WO 93/03383 A1 | 2/1993 |
| WO | WO 93/07292 A1 | 4/1993 |
| WO | WO 93/20450 A1 | 10/1993 |
| WO | WO 93/25912 A2 | 12/1993 |
| WO | WO 94/18547 A1 | 8/1994 |
| WO | WO 95/11454 A1 | 4/1995 |

(56) References Cited

FOREIGN PATENT DOCUMENTS

| | | |
|---|---|---|
| WO | WO 96/31781 A1 | 10/1996 |
| WO | WO 97/16561 A1 | 5/1997 |
| WO | WO 97/27324 A1 | 7/1997 |
| WO | WO 9731105 A1 | 8/1997 |
| WO | WO 97/34908 A1 | 9/1997 |
| WO | WO 97/46712 A2 | 12/1997 |
| WO | WO 9746707 A2 | 12/1997 |
| WO | WO 98/00697 A1 | 1/1998 |
| WO | WO 99/00655 A2 | 1/1999 |
| WO | WO 99/57561 A2 | 11/1999 |
| WO | WO 00/13014 A1 | 3/2000 |
| WO | WO 00/42418 A1 | 7/2000 |
| WO | WO 01/04608 A | 1/2001 |
| WO | WO 02/33383 A1 | 4/2002 |
| WO | WO 2003/023379 A1 | 3/2003 |
| WO | WO 03/098278 A2 | 11/2003 |
| WO | 2004-104547 A2 | 2/2004 |
| WO | WO 04/073486 A2 | 9/2004 |
| WO | WO 04/087950 A2 | 10/2004 |
| WO | WO 05/029041 A2 | 3/2005 |
| WO | WO 05/121963 A2 | 12/2005 |
| WO | WO 2006/092317 A1 | 9/2006 |
| WO | WO 06/119166 A2 | 11/2006 |
| WO | WO 06/121997 A2 | 11/2006 |
| WO | WO 07/076023 A2 | 7/2007 |
| WO | 2007/095235 A2 | 8/2007 |
| WO | WO 07/093939 A1 | 8/2007 |
| WO | WO 07/094758 A2 | 8/2007 |
| WO | WO 07/120816 A2 | 10/2007 |
| WO | WO 08/055915 A2 | 5/2008 |
| WO | 2012/116308 A1 | 8/2012 |

OTHER PUBLICATIONS

Anonymous, "Cup and Tip Supply Ring," Research Disclosure, Mason Publications, Emsworth GB, No. 318, 3 pages (Oct. 1990).

Bowie et al., "α-Thalassemia Subtyping the the Detection of Silent Mutations by High-Resolution Fragment Analysis and DNA Sequencing", Mol. Diagn., 3: 43-53 (Mar. 1998).

Kristensen et al., "High-Throughput Screening for Known Mutations by Automated Analysis of Single Sequencing Reactions", BioTechniques, 24: 832-835 (May 1998).

Leonard et al., "Preparation of PCR Products for DNA Sequencing", BioTechniques, 24: 314-317 (Feb. 1998).

Schmitz et al., "Recent Advances in Molecular Genetics of Cardiovascular Disorders—Implications for Atherosclerosis and Diseases of Cellular Lipid Metabolism", Pathol. Oncol. Res. 4: 153-161 (1998).

Van Gemen, et al., "The One-tube Quantitative HIV-1 RNA NASBA: Precision, Accuracy, and Application", PCR Methods and Applications, 4:S177-S184, Cold Spring Harbor Laboratory (1995).

Wu et al., "Strategies for Unambiguous Detection of Allelic Heterozygosity via Direct DNA Sequencing of PCR Products: Application to the HLA DRB1 Locus", Mol. Diagn., 1: 89-98 (Jun. 1996).

Notice of Allowance in co-pending U.S. Appl. No. 11/372,222, 15 pages, (dated Dec. 27, 2010).

Notice of Reasons for Rejection and English translation in Japanese Application No. 2008-501021, 11 pages, (dated Sep. 7, 2011).

USPTO Office Action, U.S. Appl. No. 12/939,420, dated Dec. 1, 2011.

USPTO Office Action, U.S. Appl. No. 13/031,889, dated Dec. 6, 2011.

Notice of Final Rejection, Japanese Application No. 2008-501021, dated Feb. 27, 2012.

European Patent Office Communication Rule 62 EPC issued in EP Application No. 10000735.0-2204, 9 pages (dated May 3, 2010).

European Patent Office Communication Article 94(3) EPC issued in EP Application No. 10000735.0-2204, 6 pages (dated Apr. 29, 2011).

Intellectual Property Office of Australia Examiner's Report issued in AU Application No. 2008265610, 2 pages (dated Feb. 7, 2012).

Non-final Office Action in U.S. Appl. No. 12/143,593, 38 pages (dated Apr. 1, 2010).

Non-final Office Action in U.S. Appl. No. 12/143,593, 21 pages (dated Sep. 2, 2010).

Final Office Action in U.S. Appl. No. 12/143,593, 22 pages (dated Feb. 17, 2011).

Advisory Action in U.S. Appl. No. 12/143,593, 10 pages (dated May 9, 2011).

Non-final Office Action in U.S. Appl. No. 12/143,593, 23 pages (dated Feb. 10, 2012).

Unknown, "Fiber Optic Fluorometer," Analyte 2000™, Research International, USA, 2 pages.

Wu et al., "Time-resolved multichannel imaging of fluorescent objects embedded in turbid media," Optics Letters, Optical Society of America, USA, 20(5): 489-491 (1995).

Zimmer-Faust et al., "A fast, multichannel fluorometer for investigating aquatic chemoreception and odor trails," Limnol. Oceanogr., 33(6) pt. 2:1586-1595, American Society of Limnology and Oceanography, Inc., USA, (1988).

International Search Report and Written Opinion issued in co-pending Application No. PCT/US2012/026579, 10 pages (dated Jun. 11, 2012).

International Search Report and Written Opinion issued in International Application No. PCT/US2008/067760, 16 pages (dated May 30, 2011).

Non-final Office Action issued in co-pending U.S. Appl. No. 12/791,390, 69 pages (dated Jun. 27, 2012).

Non-final Office Action issued in U.S. Appl. No. 12/143,593, 19 pages (dated Jan. 18, 2013).

Final Office Action issued in U.S. Appl. No. 12/143,593, 17 pages (dated May 9, 2013).

Non-final Office Action issued in U.S. Appl. No. 12/143,593, 31 pages (dated Jul. 26, 2013).

Final Office Action issued in U.S. Appl. No. 12/791,390, 11 pages (dated Nov. 8, 2012).

Non-final Rejection issued in U.S. Appl. No. 13/404,437, 6 pages (dated May 24, 2013).

Notice of Allowance issued in U.S. Appl. No. 13/404,437, 11 pages (dated Dec. 23, 2013).

Intellectual Property Office of Australia Examiner's Report issued in AU Application No. 2012222178, 3 pages (dated Dec. 17, 2013).

European Patent Office Communication issued in EP Application No. 11075040.3-1553, 11 pages (dated May 28, 2014).

"User Bulletin #2 ABI Prism 7700 Sequence Detection System", Internet Citation, Dec. 11, 1997 (Dec. 11, 1997, XP002346434, Retrieved from the Internet: URL:http://www.ukl.uni-freiburd.de/core-facility/taqman/user_bulletin_2.pdf [retrieved on Sep. 23, 2005].

USPTO Office Action, U.S. Appl. No. 14/222,180, dated Apr. 22, 2016.

EPO, Communication Pursuant to Article 94(3) EPC, European Patent Application No. 12716105.7, dated Jun. 3, 2016.

JPO Official Action, Japanese Patent Application No. 2015-109655, dated May 19, 2016.

Final Office Action issued in U.S. Appl. No. 14/222,180, 17 pages (dated Jan. 12, 2017).

Kress et al., Applied Digital Optics, 2009, pp. 2-3, John Wiley & Sons, UK.

EPO, Communication Pursuant to Article 94(3) EPC, European Application No. 12716105.7, dated Jun. 7, 2017.

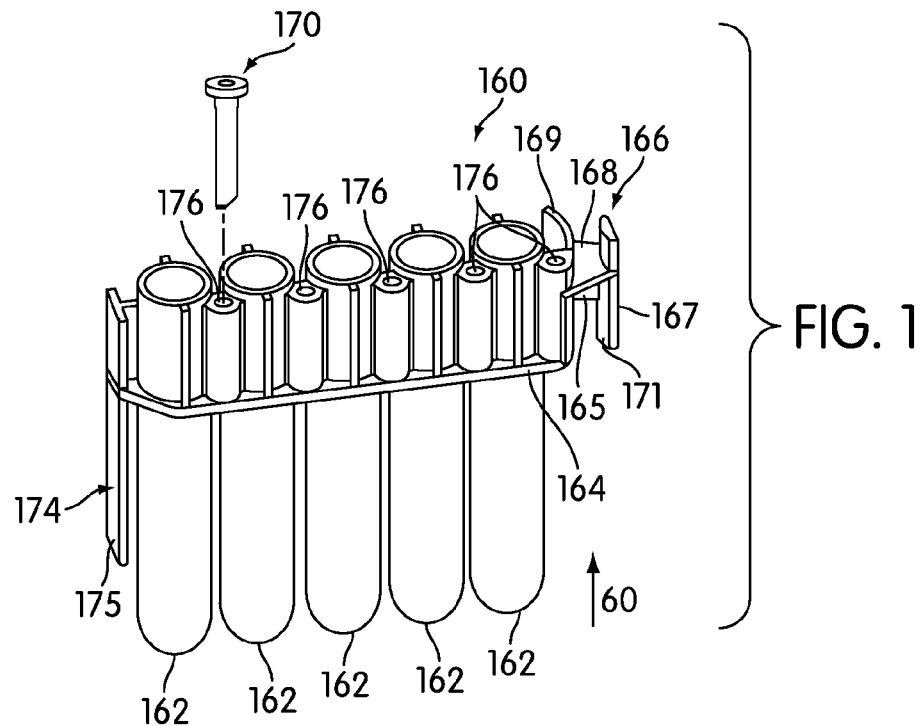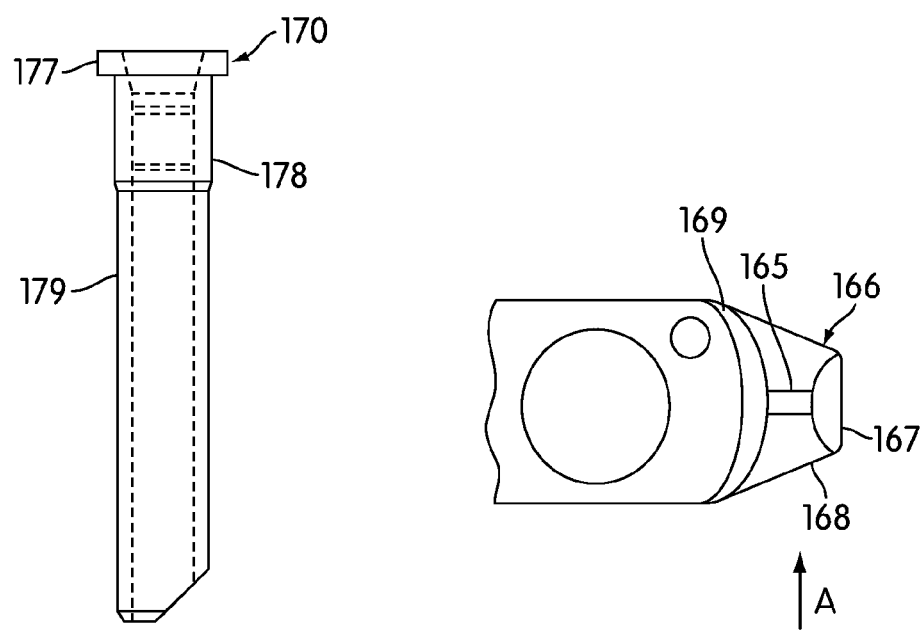

SYSTEMS AND METHODS FOR DISTINGUISHING OPTICAL SIGNALS OF DIFFERENT MODULATION FREQUENCIES IN AN OPTICAL SIGNAL DETECTOR

CROSS-REFERENCE TO RELATED APPLICATIONS

This application is a divisional application under 35 U.S.C. § § 120, 121 of U.S. patent application Ser. No. 13/404,437, filed Feb. 24, 2012, which claims the benefit under 35 U.S.C. § 119(e) of U.S. Provisional Application No. 61/446,280, filed Feb. 24, 2011, the disclosures of which are hereby incorporated by reference in their entirety.

BACKGROUND

Field of the Invention

The present invention relates to systems and methods for performing multiple diagnostic assays simultaneously, and more particularly to systems and methods for distinguishing different measured emission signals based on the modulation frequencies of the corresponding excitation signals that generated the emission signals.

Background of the Invention

None of the references described or referred to herein are admitted to be prior art to the claimed invention.

Diagnostic assays are widely used in clinical diagnosis and health science research to detect or quantify the presence or amount of biological antigens, cell or genetic abnormalities, disease states, and disease-associated pathogens or genetic mutations in an organism or biological sample. Where a diagnostic assay permits quantification, practitioners may be better able to calculate the extent of infection or disease and to determine the state of a disease over time. Diagnostic assays are frequently focused on the detection of chemicals, proteins or polysaccharides antigens, nucleic acids, biopolymers, cells, or tissue of interest. A variety of assays may be employed to detect these diagnostic indicators.

Nucleic acid-based assays, in particular, generally include multiple steps leading to the detection or quantification of one or more target nucleic acid sequences in a sample. The targeted nucleic acid sequences are often specific to an identifiable group of proteins, cells, tissues, organisms, or viruses, where the group is defined by at least one shared sequence of nucleic acid that is common to members of the group and is specific to that group in the sample being assayed. A variety of nucleic acid-based detection methods are fully described by Kohne, U.S. Pat. No. 4,851,330, and Hogan, U.S. Pat. No. 5,541,308.

Detection of a targeted nucleic acid sequence frequently requires the use of a nucleic acid molecule having a nucleotide base sequence that is substantially complementary to at least a portion of the targeted sequence or its amplicon. Under selective assay conditions, the probe will hybridize to the targeted sequence or its amplicon in a manner permitting a practitioner to detect the presence of the targeted sequence in a sample. Techniques of effective probe preparation are known in the art. In general, however, effective probes are designed to prevent non-specific hybridization with itself or any nucleic acid molecule that will interfere with detecting the presence of the targeted sequence. Probes may include, for example, a label capable of detection, where the label is, for example, a radiolabel, a fluorophore or fluorescent dye, biotin, an enzyme, a chemiluminescent compound, or another type of detectable signal known in the art.

Because the probe hybridizes to the targeted sequence or its amplicon in a manner permitting detection of a signal indicating the presence of the targeted sequence in a sample, the strength of the signal is proportional to the amount of target sequence or its amplicon that is present. Accordingly, by periodically measuring, during an amplification process, a signal indicative of the presence of amplicon, the growth of amplicon overtime can be detected. Based on the data collected during this "real-time" monitoring of the amplification process, the amount of the target nucleic acid that was originally in the sample can be ascertained. Systems and methods for real time detection and for processing real time data to ascertain nucleic acid levels are described, for example, in Lair, et al., U.S. Pat. No. 7,932,081, "Signal measuring system for conducting real-time amplification assays," the disclosure of which is hereby incorporated by reference.

To detect different nucleic acids of interest in a single assay, different probes configured to hybridize to different nucleic acids, each of which may provide detectably different signals can be used. For example, different probes configured to hybridize to different targets can be formulated with fluorophores that fluoresce at a predetermined wavelength when exposed to excitation light of a prescribed excitation wavelength. Assays for detecting different target nucleic acids can be performed in parallel by alternately exposing the sample material to different excitation wavelengths and detecting the level of fluorescence at the wavelength of interest corresponding to the probe for each target nucleic acid during the real-time monitoring process. Parallel processing can be performed using different signal detecting devices constructed and arranged to periodically measure signal emissions during the amplification process, and with different signal detecting devices being configured to generate excitation signals of different wavelengths and to measure emission signals of different wavelengths.

Occasionally, however, the excitation and emission wavelengths for one fluorophore will overlap the excitation and emission wavelengths of another fluorophore. In such circumstances, it becomes a challenge to ensure that a measured signal is entirely due to an emission of the fluorophore of interest, excited by an intended excitation signal. Such "optical crosstalk" can take a number of forms. For signal detecting devices configured to measure emissions from samples held in closely adjacent reaction receptacles, crosstalk can occur when one channel detects the excitation light from another channel (of the same or different signal detector) or when one signal detecting device picks up emission light from a receptacle that is excited by a different signal detecting device. In addition, crosstalk can occur when an excitation signal for a particular dye color excites a dye of a color that is not intended for that signal detector. Furthermore, crosstalk can occur when an emission signal for a particular dye color excites a dye of a color that is not intended for that signal detector.

Synchronous detection is a means to reduce some forms of crosstalk, as well as optical noise due to, for example, ambient light. Synchronous detection creates a narrow bandwidth filter that is sensitive to a narrow range of frequencies in the emission signal centered at a modulation frequency of the excitation signal. The excitation signal from the signal detecting device is demodulated at the modulation frequency, and a fluorescence detection circuit is configured to detect the frequency of the measured emission signal and to reject portions of the signal having a frequency that is inconsistent with the excitation frequency. Such a circuit-based "analog demodulator" is described, for example, in Lair, et al., U.S. Pat. No. 7,932,081.

SUMMARY OF THE INVENTION

The systems and methods of the present invention provide improved procedures for performing synchronous detection as well as improved procedures and mechanisms for exploiting synchronous detection for limiting or avoiding crosstalk.

Accordingly, aspects of the invention are embodied in a method for detecting multiple different optical signals emitted from the contents of each of two or more receptacles, each different optical signal indicating the presence of a different analyte of interest or amplification products thereof. The method comprises forming amplification products of an analyte of interest within each receptacle, and, while forming the amplification products, directing an excitation signal at each receptacle. The excitation signal has a predetermined excitation wavelength that excites an emission moiety, which emits an emission signal that is associated with the excitation wavelength and has a predetermined emission wavelength, and each excitation signal has a predetermined excitation frequency. With a signal detecting device, an optical signal, including an emission signal emitted from each receptacle, is detected and detection data from the detected signal is generated. The detection data is digitized by a computer-implemented algorithm. An amplitude of the detection data at the predetermined excitation frequency is determined from the digitized data by a computer-implemented algorithm to ascertain the portion of the detected signal that corresponds to the associated emission signal. The steps of directing the excitation signal, detecting an optical signal, digitizing the detection data, and detecting the amplitude of the detection data at the predetermined excitation frequency are repeated for each of the multiple different optical signals to be detected. The predetermined excitation frequency for an excitation signal associated with the emission signal of one emission moiety is different from the predetermined excitation frequency for at least one other emission moiety in the receptacle.

Further aspects of the invention are embodied in the method of detecting multiple different optical signals, wherein detecting an optical signal comprises measuring an intensity of an optical signal at each of a plurality of discrete times, and wherein the measured intensity of the optical signal at each discrete time comprises an average intensity measured over a range of time including the discrete time.

Further aspects of the invention are embodied in the method of detecting multiple different optical signals, wherein three or more different optical signals are detected from each of the receptacles.

Further aspects of the invention are embodied in the method of detecting multiple different optical signals, wherein the excitation frequencies are the same for two or more, but less than all, of the optical signals to be detected.

Further aspects of the invention are embodied in the method of detecting multiple different optical signals, wherein the emission signal is a fluorescent emission.

Further aspects of the invention are embodied in the method of detecting multiple different optical signals, wherein the emission moiety comprises a fluorescent dye, and each different optical signal is generated by a different fluorescent dye contained in the receptacle.

Further aspects of the invention are embodied in the method of detecting multiple different optical signals, wherein the at least one optical signal comprises first, second, and third optical signals. The first optical signal comprises a first range of optical wavelengths, the second optical signal comprises a second range of optical wavelengths, and the third optical signal comprises a third range of optical wavelengths. The spectra of the first and second range of optical wavelengths at least partially overlap each other, the spectra of the second and third range of optical wavelengths at least partially overlap each other, but the spectra of the first and third range of optical wavelengths do not overlap each other. The excitation frequencies of the excitation signals associated with the first and third optical signals are the same, and the excitation frequency of the excitation signal associated with the second optical signal is different from the excitation frequencies of the excitation signals associated with the first and third optical signals.

Further aspects of the invention are embodied in the method of detecting multiple different optical signals, wherein the two or more receptacles are arranged in a linear, side-by-side arrangement and wherein the predetermined excitation frequencies for adjacent receptacles are different. In some embodiments, the predetermined excitation frequencies for alternate receptacles are the same.

Further aspects of the invention are embodied in the method of detecting multiple different optical signals, wherein detecting the amplitude of the detection data at the predetermined excitation frequency comprises executing a Goertzel signal processing technique.

Further aspects of the invention are embodied in the method of detecting multiple different optical signals, which also includes the step of executing a computer-implemented algorithm for determining, from data relating to the portion of the detected signal that corresponds to the associated emission signal, the amount of an analyte present within each receptacle.

Further aspects of the invention are embodied in the method of detecting multiple different optical signals, wherein the detection data is digitized at a frequency that is at least twice the excitation frequency of an associated excitation signal.

Further aspects of the invention are embodied in the method of detecting multiple different optical signals, wherein the excitation frequency is within the range of 200-350 Hz, and the digitization frequency is about 4 kHz. Further aspects of the invention are embodied in the method of detecting multiple different optical signals, wherein the excitation frequency is within the range of 100 Hz-1 kHz, and the digitization frequency is within the range of 2 kHz-8 kHz. Further aspects of the invention are embodied in the method of detecting multiple different optical signals, wherein the excitation frequency is within the range of 10 Hz-5 kHz, and the digitization frequency is within the range of 1 kHz-1 GHz.

Further aspects of the invention are embodied in the method of detecting multiple different optical signals, which further includes the steps of forming amplification products of a control analyte and performing the steps of directing the excitation signal, detecting an optical signal, digitizing the detection data, and detecting the amplitude of the detection data at the predetermined excitation frequency for the control analyte.

Further aspects of the invention are embodied in the method of detecting multiple different optical signals, wherein the control analyte comprises a known analyte unrelated to the analyte of interest.

Further aspects of the invention are embodied in the method of detecting multiple different optical signals, which further includes adding a control probe having specificity for the control analyte to each receptacle, wherein the control probe comprises an emission moiety that emits an emission signal having an emission wavelength that is different from the emission wavelength of the emission moiety for the analyte of interest.

Further aspects of the invention are embodied in the method of detecting multiple different optical signals, which further includes executing a computer-implemented algorithm for determining from data relating to the portion of the detected signal that corresponds to the associated emission signal the amount of the control analyte.

Further aspects of the invention are embodied in the method of detecting multiple different optical signals, which further includes alternately exposing the contents of the receptacle to light energy at different excitation wavelengths and detecting the presence or absence of a signal having the emission wavelength of the emission moiety of the control probe as in indication of the successful formation of amplification products.

Further aspects of the invention are embodied in the method of detecting multiple different optical signals, wherein each receptacle is releasably fixed within the side-by-side arrangement.

Aspects of the invention are also embodied in a system for detecting an optical signal emitted from a receptacle. The system comprises an excitation device and a signal detecting device. The excitation device is constructed and arranged to generate an excitation signal. The excitation signal has a predetermined excitation wavelength and a predetermined excitation frequency and excites an emission moiety, which emits an emission signal that is associated with the excitation wavelength and has a predetermined emission wavelength. The excitation device is further constructed and arranged to direct the excitation signal at the receptacle. The signal detecting device is constructed and arranged to detect an optical signal, including an emission signal emitted from the receptacle, and to store detection data relating to the detected signal on a computer-readable medium. The system further includes a processor for executing an algorithm to digitize the stored detection data and a processor for executing an algorithm for determining, from the digitized detection data, an amplitude of the emission signal at the predetermined excitation frequency to ascertain the portion of the detected signal corresponding to the associated emission signal.

Further aspects of the invention are embodied in the system for detecting an optical signal emitted from a receptacle, which further includes a processor for executing an algorithm for determining the amount of an analyte present within the receptacle based on data relating to the portion of the detected signal corresponding to the associated emission signal.

Further aspects of the invention are embodied in the system for detecting an optical signal emitted from a receptacle, which further includes a plurality of excitation devices in fixed positions with respect to each other and a plurality of signal detecting devices in fixed positions with respect to each other. Each excitation device is constructed and arranged to (a) generate an excitation signal having a predetermined excitation wavelength and a predetermined excitation frequency that excites an emission moiety that emits an associated emission signal having a predetermined emission wavelength and (b) direct the excitation signal at a different receptacle. Each signal detecting device is constructed and arranged to detect an emission signal emitted from a receptacle and to store detection data relating to the detected signal on a computer-readable medium. Each excitation device corresponds with an associated detecting device such that the generated excitation signal and detected emission signal of each associated excitation and detecting device are directed at, and emitted from, an associated receptacle. The processor is configured to digitize the stored detection data associated with each signal detecting device, and the processor is configured to determine from the digitized detection data associated with each signal detecting device an amplitude of the emission signal at the associated predetermined excitation frequency and to ascertain the portion of the associated detected signal that corresponds to the associated emission signal.

Further aspects of the invention are embodied in the system for detecting an optical signal emitted from a receptacle, wherein the different associated receptacles comprise a plurality of receptacles arranged in a linear, side-by-side arrangement and wherein the associated predetermined excitation frequencies for adjacent receptacles are different.

Further aspects of the invention are embodied in the system for detecting an optical signal emitted from a receptacle, wherein the associated predetermined excitation frequencies for alternate receptacles are the same.

Further aspects of the invention are embodied in the system for detecting an optical signal emitted from a receptacle, which further includes a receptacle moving apparatus constructed and arranged to move the different associated receptacles relative to the plurality of excitation and detecting devices.

Further aspects of the invention are embodied in the system for detecting an optical signal emitted from a receptacle, which includes two or more sets of the plurality of excitation and associated detecting devices, wherein each set is spatially distinct from each other set within the system.

Further aspects of the invention are embodied in the system for detecting an optical signal emitted from a receptacle, which includes three to six sets of the plurality of excitation and associated detecting devices.

Further aspects of the invention are embodied in the system for detecting an optical signal emitted from a receptacle, wherein each set of the plurality of excitation and associated detecting devices is arranged radially around a central axis.

Further aspects of the invention are embodied in the system for detecting an optical signal emitted from a receptacle, wherein each receptacle is releasably fixed within the side-by-side arrangement.

Aspects of the invention are also embodied in a method for detecting an optical signal emitted from the contents of a receptacle in the presence of multiple, different optical signals originated from the same receptacle or a different receptacle. The method comprises forming amplification products of an analyte of interest within the receptacle, and, while forming the amplification products, directing an excitation signal at the receptacle. The excitation signal has a predetermined excitation wavelength that excites an emission moiety, which emits an emission signal that is associated with the excitation wavelength and has a predetermined emission wavelength, and the excitation signal has a predetermined excitation frequency. With a signal detecting device, an optical signal, including an emission signal emitted from the receptacle, is detected, and detection data from the detected signal is generated. The detection data is digitized using a computer-implemented algorithm. An amplitude of the detection data at the predetermined excitation frequency is determined from the digitized detection data by a computer-implemented algorithm to ascertain the portion of the detected signal that corresponds to the associated emission signal.

Further aspects of the invention are embodied in the method for detecting an optical signal emitted from the contents of a receptacle, which further includes detecting a second optical signal emitted from the contents of the receptacle. While forming the amplification products, a second excitation signal is directed at the receptacle, the second excitation signal having a second predetermined excitation wavelength that excites an emission moiety, which emits a second emission signal that is associated with the second excitation wavelength and has a predetermined second emission wavelength, wherein the second excitation signal has a predetermined second excitation frequency. With the same or a different signal detecting device, an optical signal including an emission signal emitted from the receptacle is detected and second detection data from the detected signal is generated. The second detection data is digitized by a computer-implemented algorithm. An amplitude of the second detection data at the predetermined second excitation frequency is determined from the second digitized detection data by a computer-implemented algorithm to ascertain the portion of the detected signal that corresponds to the associated second emission signal.

Further aspects of the invention are embodied in the method for detecting an optical signal emitted from the contents of a receptacle, wherein the excitation frequencies are different for at least two optical signals to be detected.

Further aspects of the invention are embodied in the method for detecting an optical signal emitted from the contents of a receptacle, wherein the emission signal is a fluorescent emission.

Further aspects of the invention are embodied in the method for detecting an optical signal emitted from the contents of a receptacle, wherein the emission moiety comprises a fluorescent dye.

Further aspects of the invention are embodied in the method for detecting an optical signal emitted from the contents of a receptacle, wherein first, second, and third optical signals are detected from the receptacle. The first optical signal comprises a first range of optical wavelengths, the second optical signal comprises a second range of optical wavelengths, and the third optical signal comprises a third range of optical wavelengths. The spectra of the first and second range of optical wavelengths at least partially overlap each other, the spectra of the second and third range of optical wavelengths at least partially overlap each other, but the spectra of the first and third range of optical wavelengths do not overlap each other. The excitation frequencies of the excitation signals associated with the first and third optical signals are the same and the excitation frequency of the excitation signal associated with the second optical signal is different from the excitation frequencies of the excitation signals associated with the first and third optical signals.

Further aspects of the invention are embodied in the method for detecting an optical signal emitted from the contents of a receptacle, wherein determining the amplitude of the detection data at the predetermined frequency comprises executing a Goertzel signal processing technique.

Further aspects of the invention are embodied in the method for detecting an optical signal emitted from the contents of a receptacle, which further includes executing a computer-implemented algorithm for determining, from data relating to the portion of the detected signal that corresponds to the associated emission signal, the amount of an analyte present within the receptacle.

Further aspects of the invention are embodied in the method for detecting an optical signal emitted from the contents of a receptacle, wherein the detection data is digitized at a frequency that is at least twice the excitation frequency of the associated excitation signal.

Further aspects of the invention are embodied in the method for detecting an optical signal emitted from the contents of a receptacle, wherein the excitation frequency is within the range of 200-350 Hz, and the digitization frequency is about 4 kHz. Further aspects of the invention are embodied in the method of detecting an optical signal emitted from the contents of a receptacle, wherein the excitation frequency is within the range of 100 Hz-1 kHz, and the digitization frequency is within the range of 2 kHz-8 kHz. Further aspects of the invention are embodied in the method of detecting an optical signal emitted from the contents of a receptacle, wherein the excitation frequency is within the range of 10 Hz-5 kHz, and the digitization frequency is within the range of 1 kHz-1 GHz.

These and other features, aspects, and advantages of the present invention will become apparent to those skilled in the art after considering the following detailed description, appended claims and accompanying drawings.

DESCRIPTION OF THE DRAWINGS

FIG. 1 is a perspective view of a reaction receptacle in the form of a multiple receptacle device unit employed in combination with an apparatus embodying aspects of the present invention.

FIG. 2 is a side elevation of a contact-limiting pipette tiplet employed in combination with an instrument for performing a magnetic separation procedure and carried on the multiple receptacle device shown in FIG. 1.

FIG. 3 is an enlarged bottom view of a portion of the multiple receptacle device, viewed in the direction of arrow "60" in FIG. 1.

DETAILED DESCRIPTION OF THE PREFERRED EMBODIMENT

Multiple Receptacle Devices

Figure 4:
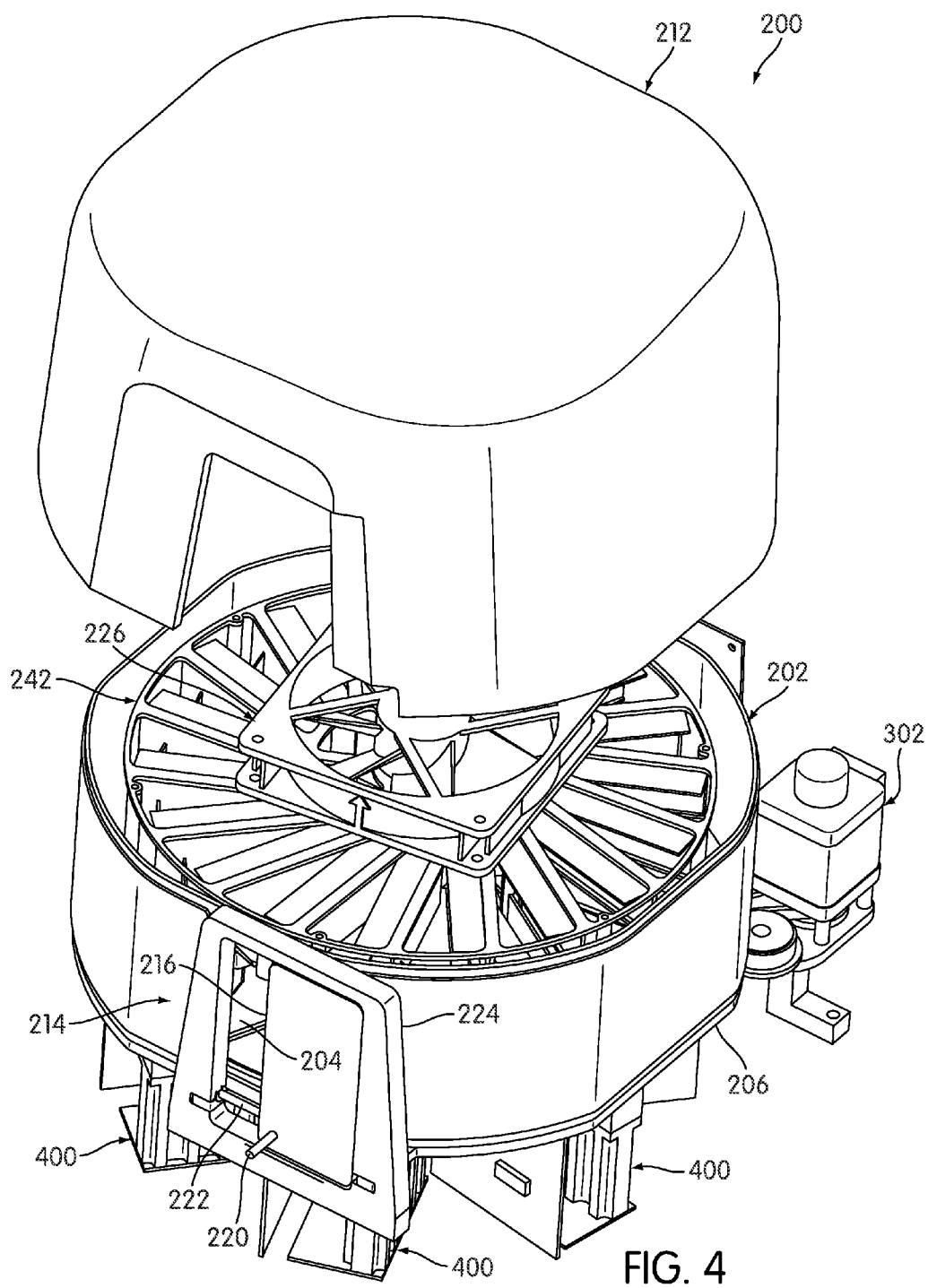
FIG. 4 is an exploded perspective view of an incubator configured to hold a plurality of receptacles while subjecting the reaction receptacles to prescribed temperature conditions and including signal detectors for detecting signals emitted by the contents of the reaction receptacles during an incubation process.

Referring to FIG. 1, a reaction receptacle in the form of a multiple receptacle device ("MRD") 160 comprises a plurality of individual receptacle vessels, or reaction tubes, 162, preferably five. The receptacle vessels 162, preferably in the form of cylindrical tubes with open top ends and closed bottom ends, are connected to one another by a connecting rib structure 164 which defines a downwardly facing shoulder extending longitudinally along either side of the MRD 160.

The MRD 160 is preferably formed from injection molded polypropylene, such as those sold by Montell Polyolefins, of Wilmington, Del., product number PD701NW or Huntsman, product number P5M6K-048. In an alternative embodiment, the receptacle vessels 162 of the MRD are releasably fixed with respect to each other by means such as, for example, a sample tube rack.

An arcuate shield structure 169 is provided at one end of the MRD 160. An MRD manipulating structure 166 extends from the shield structure 169. The manipulating structure is adapted to be engaged by a transport mechanism for moving the MRD 160 between different components of a diagnostic analyzer. An exemplary transport mechanism that is compatible with the MRD 160 is described in U.S. Pat. No. 6,335,166, the disclosure of which is hereby incorporated by reference. The MRD manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167.

As shown in FIG. 3, the shield structure 169 and vertical piece 167 have mutually facing convex surfaces. The MRD 160 may be engaged by a transport mechanism and other components, by moving an engaging member laterally (in the direction "A") into the space between the shield structure 169 and the vertical piece 167. The convex surfaces of the shield structure 169 and vertical piece 167 provide for wider points of entry for an engaging member undergoing a lateral relative motion into the space.

A label-receiving structure 174 having a flat label-receiving surface 175 is provided on an end of the MRD 160 opposite the shield structure 169 and MRD manipulating structure 166. Human and/or machine-readable labels, such as scanable bar codes, can be placed on the surface 175 to provide identifying and instructional information on the MRD 160.

The MRD 160 preferably includes tiplet holding structures 176 adjacent the open mouth of each respective receptacle vessel 162. Each tiplet holding structure 176 provides a cylindrical orifice within which is received conduit that is adapted to be placed onto the end of an aspirating tube, such as contact-limiting tiplet 170. Exemplary construction and function of the tiplet 170 is described below. Each holding structure 176 is constructed and arranged to frictionally receive a tiplet 170 in a manner that prevents the tiplet 170 from falling out of the holding structure 176 when the MRD 160 is inverted, but permits the tiplet 170 to be removed from the holding structure 176 when engaged by a pipette.

Referring to FIG. 2, the tiplet 170 comprises a generally cylindrical structure having a peripheral rim flange 177 and an upper collar 178 of generally larger diameter than a lower portion 179 of the tiplet 170. The tiplet 170 is preferably formed from conductive polypropylene. When the tiplet 170 is inserted into an orifice of a holding structure 176, the flange 177 contacts the top of structure 176 and the collar 178 provides a snug but releasable interference fit between the tiplet 170 and the holding structure 176. Alternatively, each holding structure 176 may be configured to loosely receive a tiplet 170 so that the tiplet is more easily removed from the holding structure when engaged by a pipette.

Further details regarding the MRD 160 may be found in U.S. Pat. No. 6,086,827, the disclosure of which is hereby incorporated by reference. Though a particular configuration of MRD 160 is exemplified, one of skill in the art would appreciate that a variety of configurations of single or multiple receptacle devices may be utilized according to the present invention.

Specimen Preparation Procedure

In an exemplary embodiment, samples are prepared for a magnetic separation procedure by dispensing an amount of target capture reagent, preferably mag-oligo reagent, e.g., by an automated, robotic pipetting apparatus, into each of the receptacle vessels 162 of the MRD 160. The target capture reagent includes a support material able to bind to and immobilize a target analyte. The support material preferably comprises magnetically responsive particles. The amount dispensed into each receptacle vessel 162 is typically 100-500 µl. Next, an amount of sample material is dispensed into each of the receptacle vessels 162 of the MRD 160 containing target capture reagent. A different sample may be dispensed into each of the five receptacle vessels 162, or the same sample may dispensed into two or more of the receptacle vessels 162. A magnetic separation procedure includes the steps of exposing the contents of the receptacle vessel to a magnetic field to draw the magnetically-responsive particles to a side of the receptacle vessel and out of suspension, withdrawing the fluid contents of the receptacle vessel (e.g., by vacuum aspiration) while holding the magnetically-responsive particles out of suspension, removing the magnetic field, and adding a wash solution to the receptacle vessel to re-suspend the magnetically-responsive particles. These steps may be repeated one or more times. A suitable magnetic separation wash procedure is described in Lair et al., U.S. Pat. No. 8,008,066, the disclosure of which is hereby incorporated by reference.

Real-Time Amplification Assays

Real-time amplification assays can be used to determine the presence and amount of a target nucleic acid in a sample which, by way of example, is derived from a pathogenic organism or virus. By determining the quantity of a target nucleic acid in a sample, a practitioner can approximate the amount or load of the organism or virus in the sample. In one application, a real-time amplification assay may be used to screen blood or blood products intended for transfusion for bloodborne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with, or suspected of being afflicted with, a disease characterized by aberrant or mutant gene expression. Real-time amplification assays may also be used for diagnostic purposes, as well as in gene expression determinations. In a preferred application of the present invention discussed above, the presence of an organism, virus, or gene of interest is determined using a probe which, under the particular conditions of use, exhibits specificity in a sample for a target nucleic acid sequence derived from the organism, virus, or gene of interest (i.e., contained within target nucleic acid obtained from the organism, virus, or gene of interest, or an amplification product thereof). To exhibit specificity, a probe generally has a nucleotide base sequence that is substantially complementary to at least a portion of the target or its complement such that, under selective assay conditions, the probe will detectably hybridize to the target sequence or its complement but not to any non-target nucleic acids that may be present in the sample.

Aspects of the present invention relate to systems and methods for performing "real-time" amplification assays which are distinguishable from "end-point" amplification assays. In "end-point" amplification assays, the presence of amplification products containing the target sequence or its complement is determined at the conclusion of an amplification procedure. The determination may occur in a detection station that may be located externally to the incubator in which the amplification reactions occur. In contrast, in "real-time" amplification assays, the amount of amplification products containing the target sequence or its complement is determined during an amplification procedure. In the real-time amplification assay, the concentration of a target nucleic acid can be determined using data acquired by making periodic measurements of signals that are functions of the amount of amplification product in the sample containing the target sequence, or its complement, and calculating the rate at which the target sequence is being amplified from the acquired data.

For real-time amplification assays, the probes are preferably unimolecular, self-hybridizing probes having a pair of interacting labels that interact and thereby emit different signals, depending on whether the probes are in a self-hybridized state or hybridized to the target sequence or its complement. See, e.g., Diamond et al., "Displacement Polynucleotide Assay Method and Polynucleotide Complex Reagent Therefor," U.S. Pat. No. 4,766,062; Tyagi et al., "Detectably Labeled Dual Conformation Oligonucleotide Probes, Assays and Kits," U.S. Pat. No. 5,925,517; Tyagi et al., "Nucleic Acid Detection Probes Having Non-FRET Fluorescence Quenching and Kits and Assays Including Such Probes," U.S. Pat. No. 6,150,097; and Becker et al., "Molecular Torches," U.S. Pat. No. 6,361,945. Other probes are contemplated for use in the present invention, including complementary, bimolecular probes, probes labeled with an intercalating dye and the use of intercalating dyes to distinguish between single-stranded and double-stranded nucleic acids. See, e.g., Morrison, "Competitive Homogenous Assay," U.S. Pat. No. 5,928,862; Higuchi, "Homogenous Methods for Nucleic Acid Amplification and Detection," U.S. Pat. No. 5,994,056; and Yokoyama et al., "Method for Assaying Nucleic Acid," U.S. Pat. No. 6,541,205. Examples of interacting labels include enzyme/substrate, enzyme/cofactor, luminescent/quencher, luminescent/adduct, dye dimers and Förrester energy transfer pairs. Methods and materials for joining interacting labels to probes for optimal signal differentiation are described in the above-cited references.

In a preferred real-time amplification assay, the interacting labels include a fluorescent moiety, or other emission moiety, and a quencher moiety, such as, for example, 4-(4-dimethylaminophenylazo) benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to nucleic acid present in the sample, the fluorescent and quencher moieties are separated from each other and light energy emitted by the fluorescent moiety can be detected. Fluorescent moieties which are excited and emit at different and distinguishable wavelengths can be combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties.

In one example of a multiplex, real-time amplification assay, the following may be added to a sample prior to initiating the amplification reaction: a first probe having a quencher moiety and a first fluorescent dye (having an excitation wavelength $\lambda_{ex1}$ and emission wavelength $\lambda_{em1}$) joined to its 5' and 3' ends and having specificity for a nucleic acid sequence derived from HCV; a second probe having a quencher moiety and a second fluorescent dye (having an excitation wavelength $\lambda_{ex2}$ and emission wavelength $\lambda_{em2}$) joined to its 5' and 3' ends and having specificity for a nucleic acid sequence derived from HIV Type 1 (HIV-1); and a third probe having a quencher moiety and a third fluorescent dye (having an excitation wavelength $\lambda_{ex3}$ and emission wavelength $\lambda_{em3}$) joined to its 5' and 3' ends and having specificity for a nucleic acid sequence derived from West Nile virus (WNV). After combining the probes in a sample with amplification reagents, the samples can be periodically and alternately exposed to excitation light at wavelengths $\lambda_{ex1}$, $\lambda_{ex2}$, and $\lambda_{ex3}$, and then measured for emission light at wavelengths, $\lambda_{em1}$, $\lambda_{em2}$, and $\lambda_{em3}$, to detect the presence (or absence) and amount of all three viruses in the single sample. The components of an amplification reagent will depend on the assay to be performed, but will generally contain at least one amplification oligonucleotide, such as a primer, a promoter-primer, and/or a promoter oligonucleotide, nucleoside triphosphates, and cofactors, such as magnesium ions, in a suitable buffer.

Where an amplification procedure is used to increase the amount of target sequence, or its complement, present in a sample before detection can occur, it is often desirable to include a "control" to ensure that amplification has taken place and, thereby, to avoid false negatives. Such a control can be a known nucleic acid sequence that is unrelated to the sequence(s) of interest, or another sequence. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye is likely indicative of a failed amplification, thus rendering any results from that assay suspect.

Systems and method for performing real-time amplification assays are described in Lair et al., "System for performing multi-formatted assays," U.S. Pat. No. 8,008,066, the disclosure of which is hereby incorporated by reference.

In accordance with aspects of the present invention, real-time amplification assays are performed in an incubator, such as incubator 200, features of which are shown in FIGS. 4-12. Incubator 200 is a rotary incubator in the sense that MRD's 160 are carried on a rotary carrier structure (e.g., a carousel) within a housing having a controlled temperature interior. Incubator 200 includes signal detectors, or signal detector blocks, 400 attached thereto for detecting, in a real-time manner, the amplification occurring within the reaction tubes 162 of an MRD 160 carried in the incubator, for example, by measuring the fluorescence emitted by a dye or dyes within each reaction tube 162 of the MRD 160 when the MRD 160 is illuminated with an excitation light corresponding to each dye. The incubator 200 can be integrated into an automated diagnostic analyzer (not shown) that may include one or more receptacle transport mechanisms for placing MRD's 160 into the incubator 200 and removing MRD's 160 from the incubator 200.

Features of an incubation station, or incubator 200, adapted for use in conjunction with the present invention, are shown in FIGS. 4-12. FIG. 4 shows an exploded perspective view of the incubator 200. The incubator 200 includes a housing that comprises an outer wall 202, a bottom wall 206, and a top wall (not shown), all of which are covered by a thermal insulating shroud, or hood, 212. The side, bottom and top walls are preferably formed of aluminum, and the insulating hood is preferably made from a suitable insulating material, such as polyurethane foam. A receptacle carrier 242, preferably in the form of a carousel rotatably mounted within the housing, is configured for carrying a plurality of reaction receptacles. Receptacles, such as MRDs 160, can be inserted into the receptacle carrier 242 and removed from the receptacle carrier 242 through a receptacle opening 204 formed in the sidewall 202. Receptacle opening 204 is covered by the sliding door 216 of a door assembly 214 (described in more detail below).

One or more signal detectors 400 are disposed beneath the bottom wall 206 of the incubator housing and are configured for detecting signals emitted by the contents of reaction MRDs 160 carried on the receptacle carrier 242 within the incubator 200. The signal detectors 400 are described in further detail below.

Heat may be generated within the incubator 200 by any suitable means. In one embodiment, resistive heating elements are disposed on the sidewall 202 of the incubator housing. Other suitable heating elements may include, for example, Peltier' thermoelectric heating elements. The heating elements may be under microprocessor control for maintaining a constant, desired temperature, and the incubator 200 may further include one or more temperature-sensing elements for providing temperature level signals to the microprocessor controller.

A circulating fan 226 may be positioned within the incubator housing, for example, atop the receptacle carrier 242. In one embodiment, fan 226 is an axial fan, as shown, configured for generating airflow through the receptacle carrier 242 and within the incubator 200.

Figure 5:
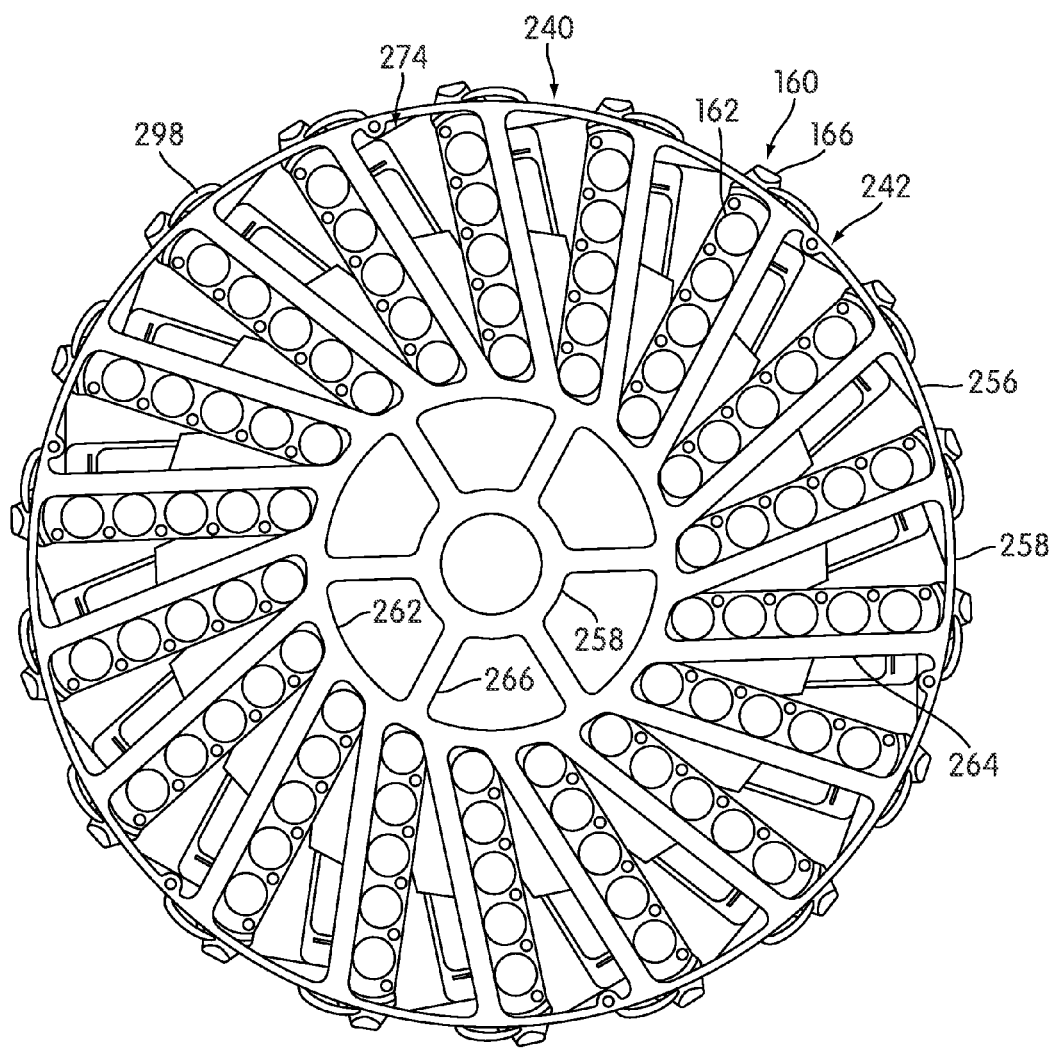
FIG. 5 is a bottom plan view of a receptacle carrier carousel of the incubator.
Figure 6:
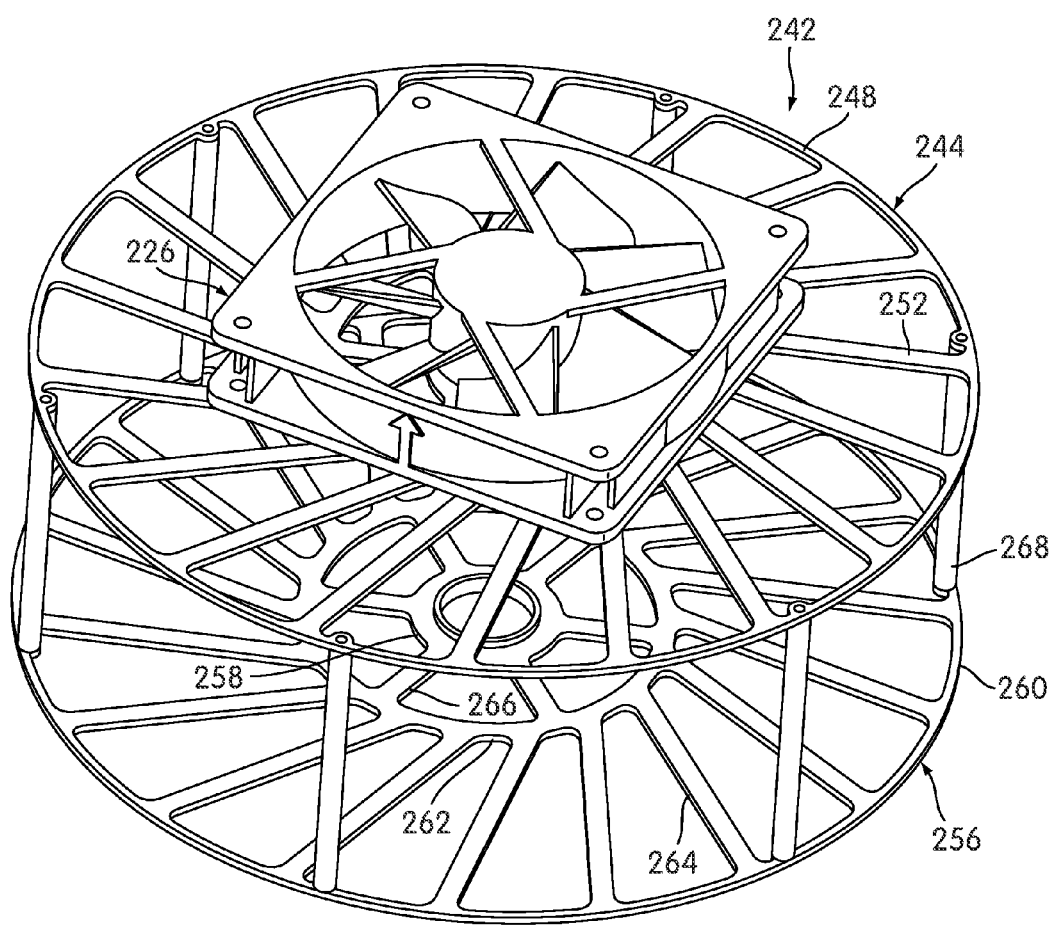
FIG. 6 is a perspective view of assembled components of a receptacle carrier carousel of the incubator and a circulating fan for generating airflow within the incubator.

Further details concerning the construction of the receptacle carrier 242 are shown in FIGS. 5 and 6. FIG. 5 is a bottom plan view of the receptacle carrier 242 with a plurality of MRDs 160 carried thereon. FIG. 6 is a perspective view of a portion of the receptacle carrier 242 and showing the fan 226 mounted atop the carrier 242.

Carrier 242 comprises an upper disk 244 and an identical lower disk 256. As shown in FIGS. 5 and 6, the lower disk includes an inner ring 258, an outer ring 260, and an intermediate ring 262 disposed concentrically between the inner ring 258 and outer ring 260. Inner radial spokes 266 extend between the inner ring 248 and the intermediate ring 262. Outer spokes 264 extend between the intermediate ring 262 and the outer ring 260 and are, in this embodiment, configured obliquely with respect to a true-radial orientation relative to the center of the intermediate ring 262 and outer ring 260.

The upper disk 244 has a similar construction, but only outer ring 248 and outer spokes 252 are visible in FIG. 6. The upper disk 244 further includes an inner ring, an intermediate ring, and inner spokes, all of which are obstructed from view by the fan 226 in FIG. 6.

The upper disk 244 and the lower disk 256 are secured relative to one another in a parallel, spaced-apart orientation by a plurality of spacer posts 268 disposed at angular intervals around the perimeters of the upper disk 244 and lower disk 256. Each spacer post 268 may be secured in place by means of a suitable fastener, such as a screw, extending through a hole in the upper disk 244 or lower disk 256 and into an opening (e.g. a threaded opening) formed in each end of each of the spacer posts 268.

The receptacle carrier 242 further includes a plurality of receptacle dividers 274 extending between each of the outer spokes 264 of the lower disk 256 and corresponding outer spokes 252 of the upper disk 244. The spaces between adjacently disposed receptacle dividers 274 define receptacle stations 240 each configured to receive a single reaction MRD 160. As shown in FIG. 5, which is a bottom plan view of a receptacle carrier carousel of the incubator, each MRD 160 is carried in a generally vertical orientation with the lower ends of each receptacle vessel 162 exposed at the bottom of the receptacle carrier 242 and with the receptacle manipulating structure 166 of each MRD 160 extending radially beyond the outer perimeter of the receptacle carrier 242.

Figure 7:
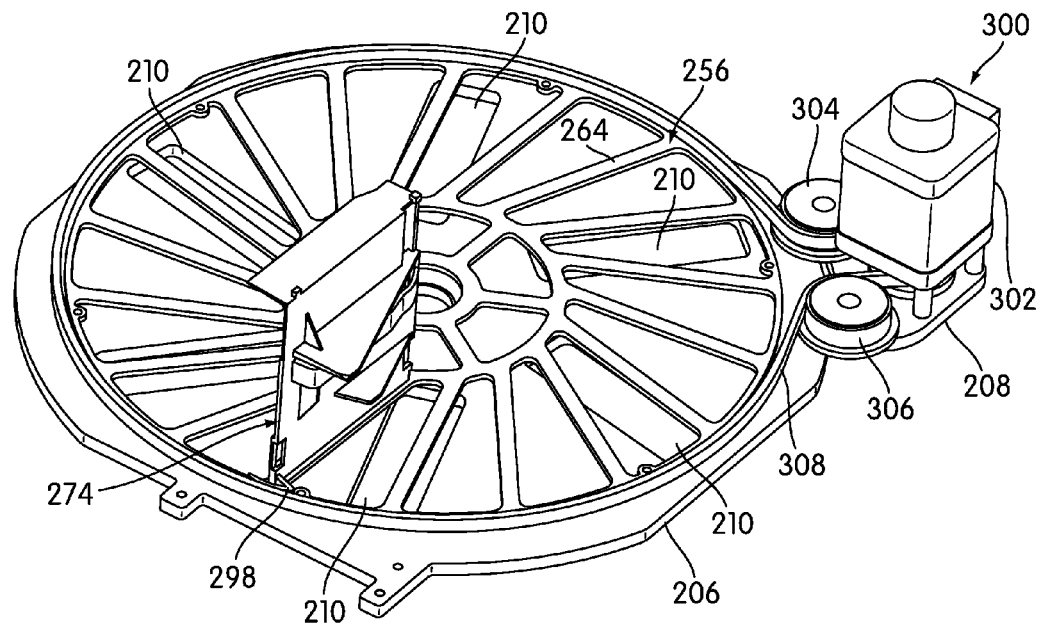
FIG. 7 is a perspective view of a bottom wall of the incubator housing, a portion of the receptacle carrier, and a receptacle carrier drive assembly.
Figure 8:
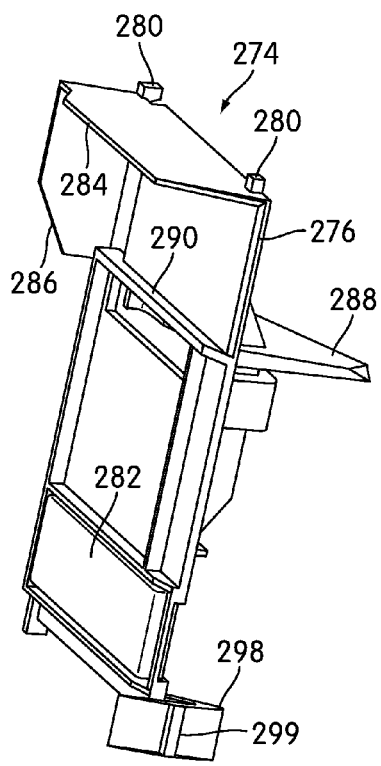
FIG. 8 is a perspective view of a receptacle divider of the receptacle carrier.
Figure 9:
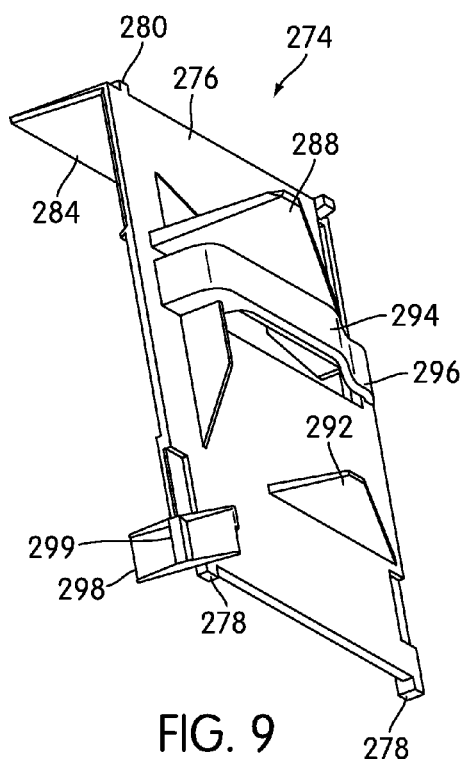
FIG. 9 is a perspective view of the receptacle divider from an opposite side of the divider.

Details of the receptacle dividers are shown in FIGS. 7-9. As noted, each receptacle divider 274 is attached to one of the outer spokes 264 of the lower disk 256, as shown in FIG. 7. The receptacle divider 274 includes a divider wall 276 that is oriented generally vertically when the divider 274 is installed between the upper disk 244 and lower disk 256. The divider wall 276 includes lower positioning posts 278 configured to be inserted into mating openings formed in the lower disk 256 (not shown) and upper positioning posts 280 configured to be inserted into mating openings (not shown) formed in the upper disk 244. A magnet 282 may be mounted alongside a lower end of the divider wall 276. The magnet 282 extends from one edge of the divider wall 276 to an opposite edge. The reaction receptacles carried in the incubator 200 may contain therein magnetically responsive particles for effecting a magnetic separation procedure for isolating an analyte of interest, and the presence of such particles within the contents of the reaction receptacle may obscure any signal emitted by the contents that is to be detected by the signal detectors 400. Accordingly, the magnet 282 mounted to the divider wall 276 aggregates at least a portion of the magnetic particles to one side of the receptacle vessels 162, thereby removing the particles from a suspension where they can obscure the signal. More specifically, the magnetic particles used for target capture in an embodiment of the invention can affect real-time detection of amplification products. Two particular interfering effects have been identified. First, magnetic particles can inhibit amplification by adsorption of oligonucleotides (e.g., amplification oligonucleotides and probes) and enzyme reagents (e.g., nucleic acid polymerases). In addition, the presence of magnetic particles (settled or in suspension) can result in the dissipation of the fluorescence, thereby blocking or partially blocking the amount of excitation light that reaches the detection dyes and the amount of light emitted from the reaction tubes 162 of the MRDs 160. This is known as the black cloud effect. Thus, to minimize this effect, the dividers 274 of the incubator 200 include a magnet 282 as shown in FIG. 8.

Each divider 274 includes a receptacle cover flange 284 which will cover the open upper ends of the receptacle vessels 162, and a receptacle stop wall 286 to prevent the reaction MRD 160 from being inserted into the receptacle station 240 beyond a desired position. Each divider 274 further includes, on one side thereof, a receptacle hanger flange 288 and a receptacle guide wing 292, and the opposite side of the divider wall 276 includes a receptacle support ledge 290. The angled shape of the receptacle hanger flange 288 defines a constant spacing between the edge of the hanger flange 288 of one divider 274 and the receptacle support ledge 290 of an adjacent divider 274 to provide parallel edges for supporting the connecting rib structure 164 of the MRD 160 when the MRD 160 is inserted into the receptacle station 240. The divider 274 further includes a receptacle retainer spring 294 configured as a resilient, cantilevered projection with a free end 296 slightly curved so as to conform to the radially innermost end receptacle vessel 162 when the MRD 160 is inserted into the receptacle station 240. The retainer spring 294, by its own resilience, releasably secures the MRD 160 in the receptacle station 240. Each divider 274 further includes a drive belt support element 298 at a lower edge of the divider wall 276. Each drive belt support 298 may include a raised rib 299.

In a preferred embodiment of the invention, the incubator 200 holds eighteen MRDs 160 at a time, each spaced at 20° increments around the carousel.

A drive assembly 300 of the receptacle carrier 242 includes a motor 302 mounted on a motor mount portion 208 of the bottom wall 206 of the incubator housing, guide wheels 304 and 306, and a drive belt 308. Drive belt 308 is secured around a drive shaft (not shown) of the motor 302, around the guide wheels 304 and 306, and further over the belt drive supports 298 of the plurality of dividers 274 mounted between the upper disk 244 and lower disk 256. As noted, each drive belt support 298 may include a vertical rib 299 for engaging the teeth (not shown) of the drive belt 308. As shown in FIG. 7, which shows a perspective view of a bottom wall of the incubator housing, a portion of the receptacle carrier, and a receptacle carrier drive assembly, the bottom wall 206 of the incubator housing includes a plurality of elongated openings 210, preferably formed at equal angular intervals about a point corresponding to the axis of rotation of the receptacle carrier 242. The openings 210 are oriented at the same angle at which each MRD 160 will be oriented when carried on the receptacle carrier 242, and each opening 210 is configured to receive an upper end of a signal detector 400 extending into the incubator 200 for detecting signals emitted by the contents of the MRDs 160 during the incubation process. Motor 302 is preferably a stepper motor under microprocessor control. A "home" position sensor (not shown) indicates when the receptacle carrier 242 is in a specified rotational position, and the motor 302 is provided with an encoder. Accordingly, movement of the receptacle carrier 242 can be controlled, e.g., by a microprocessor receiving signals from the home sensor and an encoder coupled to motor 302 to control and monitor the angular movement and positioning of the carrier 242, to sequentially place each MRD 160 on the receptacle carrier 242 into a signal detection position above the openings 210.

Figure 10:
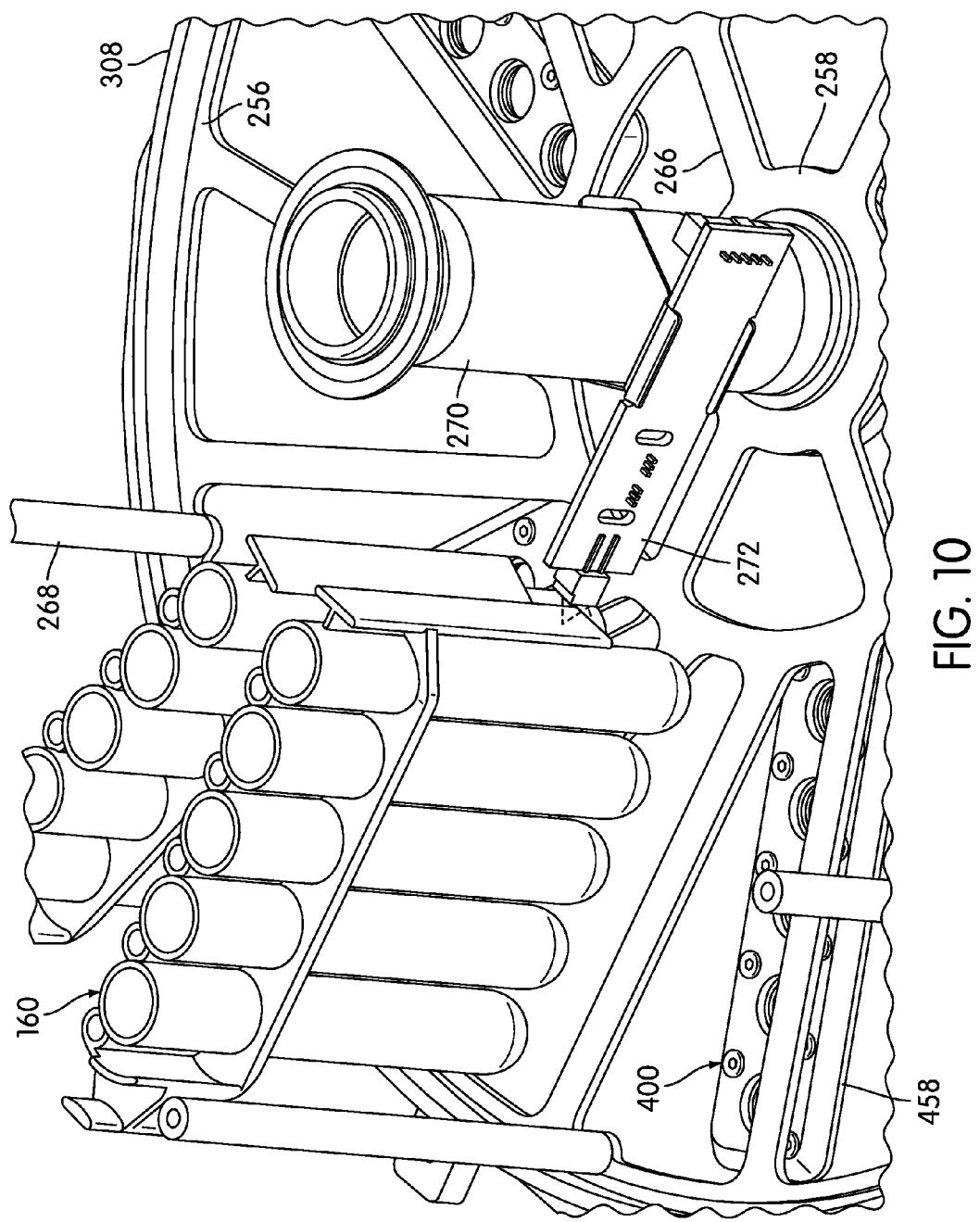
FIG. 10 is a partial perspective view of components of the receptacle carrier of the incubator including a receptacle present sensor for detecting the presence of reaction receptacles on the receptacle carrier.

As shown in FIG. 10, which shows a partial perspective view of components of the receptacle carrier of the incubator, the receptacle carrier 242 further includes a center post 270 extending between the inner ring 258 of the lower disk 256 and the inner ring of the upper disk 244 (not shown in FIG. 10). A receptacle present sensor 272 is mounted to the center post 270 and is configured to detect the presence of an MRD 160 inserted into a receptacle station 240 of the receptacle carrier 242. Microprocessor control, which controls and monitors the angular position of the receptacle carrier 242, also monitors the location of each specific MRD (160), which may be identified by, e.g., a label, such as a machine-readable bar-code or an RFID tag. That is, when an MRD 160, identified via its label or other means, is moved into the incubator 200, the angular position of the receptacle station 240 into which that MRD 160 is inserted is determined and tracked to monitor the position of that MRD 160 at all times while the MRD is inside the incubator 200.

In one embodiment, the center post 270 and the receptacle present sensor 272 are fixed with respect to the receptacle carrier 242. The presence or absence of an MRD in any receptacle station 240 of the receptacle carrier 242 can be determined by rotating the receptacle station 240 in front of the receptacle present sensor 272.

Figure 11:
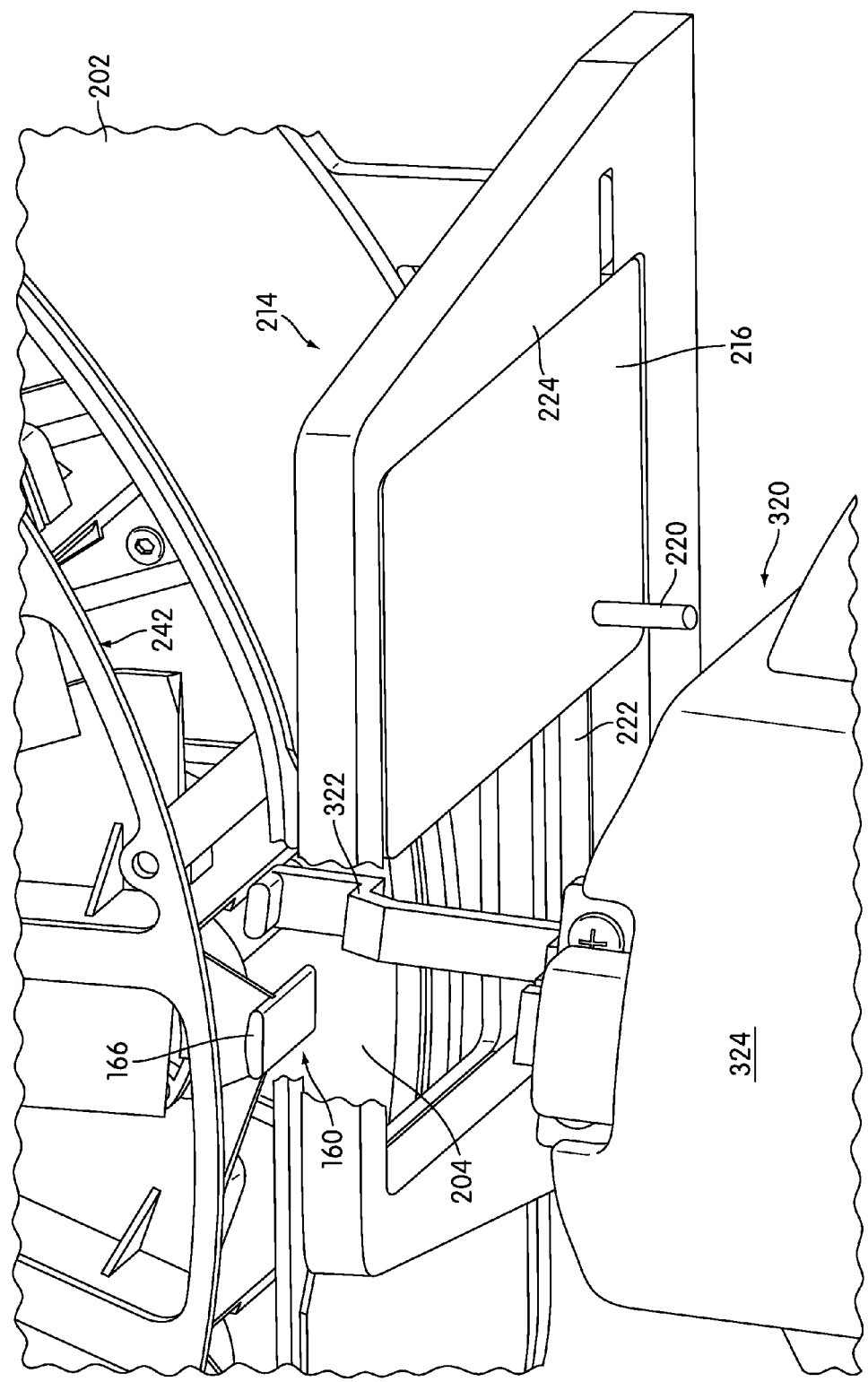
FIG. 11 is a partial perspective view of the incubator and a receptacle transport mechanism adapted to place reaction receptacles into the incubator and remove reaction receptacles from the incubator.

Details of the door assembly 214 are shown in FIGS. 4 and 11. The door assembly 214 includes a door 216 that is slidably disposed in a frame 224 secured with respect to a portion of the side wall 202 adjacent the receptacle opening 204. In FIG. 11, a portion of the frame 224 and the side wall 202 above the opening 204 is omitted so as not to obstruct view of the MRD 160. As noted, the door 216 is slidably disposed within the frame 224 and may include a groove or ridge along the top and/or bottom edge thereof which engage a ridge or groove along the edges of the opening of the frame 224 within which the door 216 is disposed. A generally horizontal guide rod 222 spans the opening formed in the frame 224 and extends through a lower portion of the door 216. A spring mechanism (not shown), such as a coil spring, may be provided to bias the door 216 into a closed position with respect to the opening 204. A sensor (not shown), such as an optical sensor, may be included to provide a signal to an instrument controller indicating that the door is a closed and/or opened position.

FIG. 11 also shows a portion of a receptacle transport mechanism 320 having a manipulating hook 322 configured to engage the manipulating structure 166 of an MRD 160. The receptacle transport mechanism 320 includes a housing 324 within which it carries an MRD 160 to and from the incubator 200 and/or any other station of an instrument that includes the incubator 200. Details of suitable receptacle transport mechanisms are described in more detail at Ammann, et al., "Automated Process For Isolating and Amplifying a Target Nucleic Acid Sequence" U.S. Pat. No. 6,335,166 or Hoerger, et al., "Method and Apparatus for Effecting Transfer of Reaction Receptacles in an Instrument for Multi-Step Analytical Procedures" International Patent Publication No. WO 2010/132885, the contents of which are hereby incorporated by reference. The door assembly 214 includes an actuating post 220 extending from the sliding door 216, and a contact element (not shown) of the receptacle transport mechanism 320 engages the actuating post 220 to push the sliding door 216 to an open position so that the manipulating hook 322 can be extended through the receptacle opening 204 to insert an MRD 160 into the receptacle carrier 242 or to retrieve an MRD 160 from the receptacle carrier 242.

The signal detectors 400 are part of a system that measures, for example, the concentration of unquenched fluorescent dye molecules in real time. The assay performed within each receptacle vessel 162 of each MRD 160 may be preferably designed such that the fluorescent signal increases as the concentration of target is increased by amplification. The signal detector 400 is used to monitor the amplification process by monitoring the emergence of the fluorescent signal.

An exemplary embodiment of the incubator 200 may include between three and six signal detectors 400, where each detector is designed to measure a particular fluorescent dye (i.e., color). Each signal detector 400 houses, for example, five individual detectors, which may comprise fluorometers. The five individual fluorometers (also referred to herein as "channels") are spaced with the same spacing as that of the receptacle vessels 162 of each MRD 160. The signal detector 400 may be provided with additional or fewer individual detectors, but the number of detectors generally corresponds to the number of receptacle vessels in each MTU 160. The signal detectors 400 are mounted to the amplification incubator 200 with such an orientation that each of them can detect signal emitted by each receptacle vessel 162 of an MRD 160 when the receptacle carrier 242 stops at preset angular increments corresponding to the angular positions of the signal detectors 400. Therefore, each MRD 160 can be scanned by each signal detector 400 once per revolution of the carrier 242.

Figure 12:
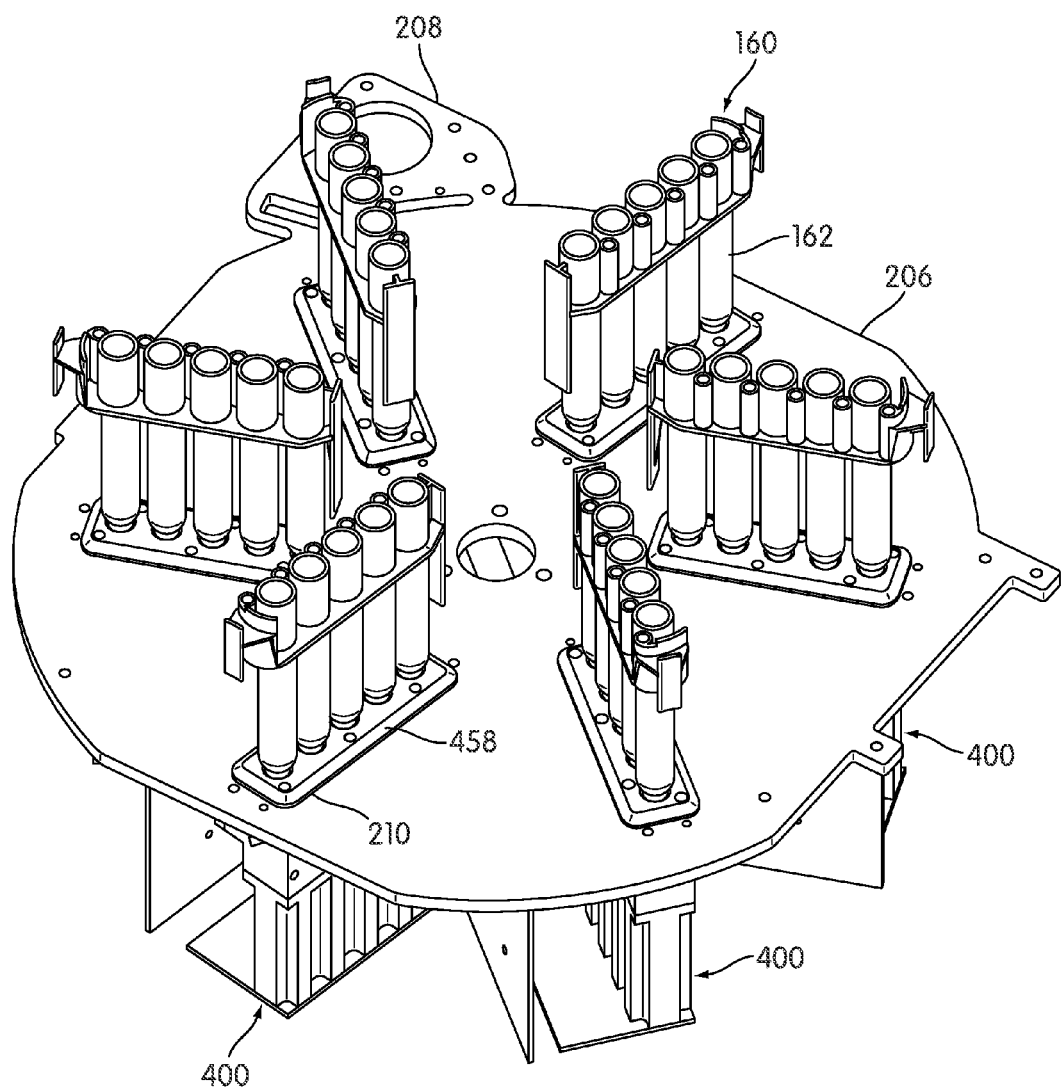
FIG. 12 is a partial perspective view of a portion of the incubator including the incubator floor, signal detectors disposed beneath the incubator floor, and reaction receptacles disposed in signal detecting positions with respect to the signal detectors.

As shown in FIG. 12, which is a partial perspective view of a portion of the incubator, in one embodiment, six signal detectors 400 are constructed and arranged to detect signals emitted by the contents of each of the five receptacle vessels 162 of six different MRD's 160 carried within the housing of the incubator 200. That is, each signal detector 400 is configured to detect a signal emitted by each of the five receptacle vessels 162 of an MRD 160 operatively positioned with respect to the signal detector 400 by the carrier 242. The signal detectors 400 may be of substantially identical constructions, but each may be adapted to detect a signal characteristic of a different measureable or detectable value. For example, each signal detector 400 may be configured to detect fluorescence of a different wavelength, and thus each may be configured, or tuned, to detect a different fluorescent dye within the contents of the receptacle vessel 162. Each signal detector 400 may also be configured to emit light at a predefined wavelength or within a range of wavelengths. The wavelength of the emitted light from the signal detector 400 frequently corresponds to an excitation wavelength window of a fluorescent dye within the contents of the receptacle vessel 162. The motor 302, which drives the receptacle carrier 242, is under the control of a microprocessor which may receive signals from a home sensor coupled to the carrier 242, a timer, and an encoder coupled to the motor 302 for controlling movement and angular positioning of the carrier 242. The carrier 242 is controlled to (a) move MRDs 160 into operative, sensing positions with respect to the signal detector(s) 400, (b) pause for a sufficient period of time to permit the signal detector(s) to take and process a signal reading from the MRD operatively positioned with respect to it, and (c) index the carrier 242 to position the next MRD(s) 160 into operative position(s) with respect to the signal detector(s) 400. The signal detectors 400 attached to the incubator 200 for real-time fluorescence detection are known as optical detection modules (a type of a signal detector or signal measuring device), as will now be described.

Figure 13:
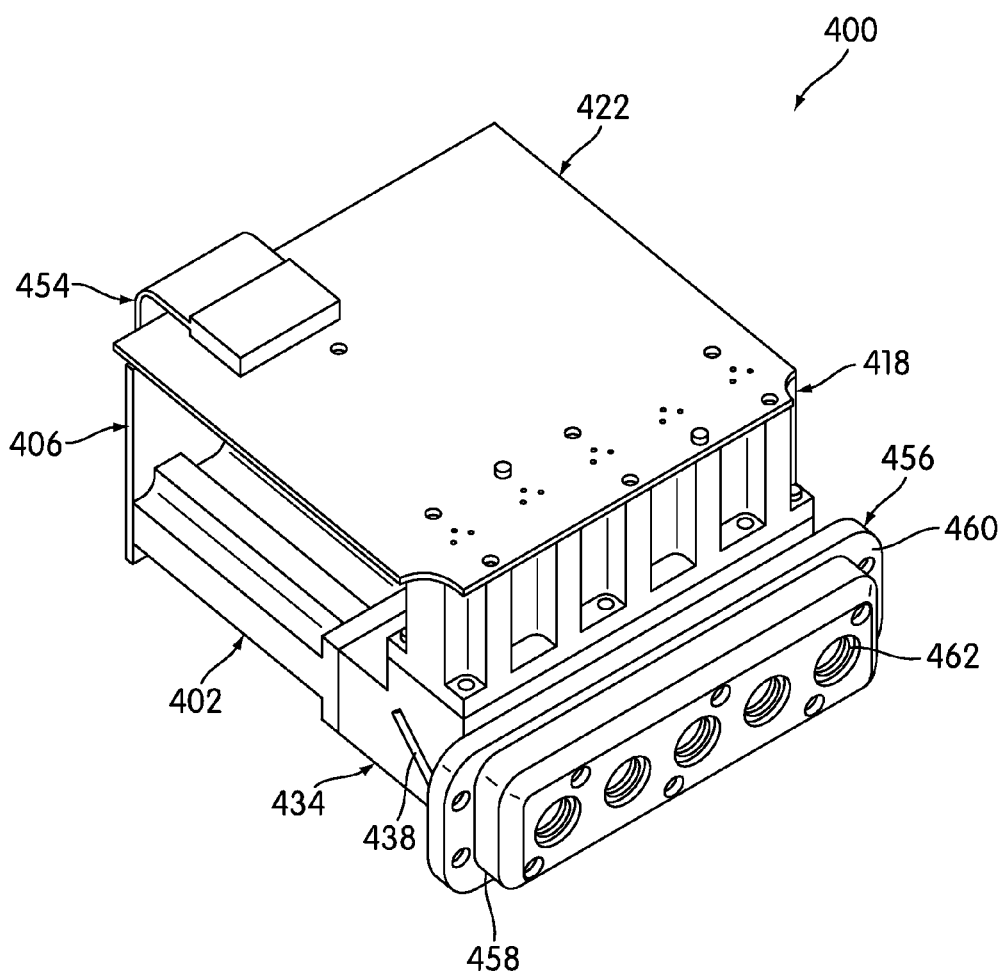
FIG. 13 is a perspective view of a signal detector for use in conjunction with the present invention.
Figure 14:
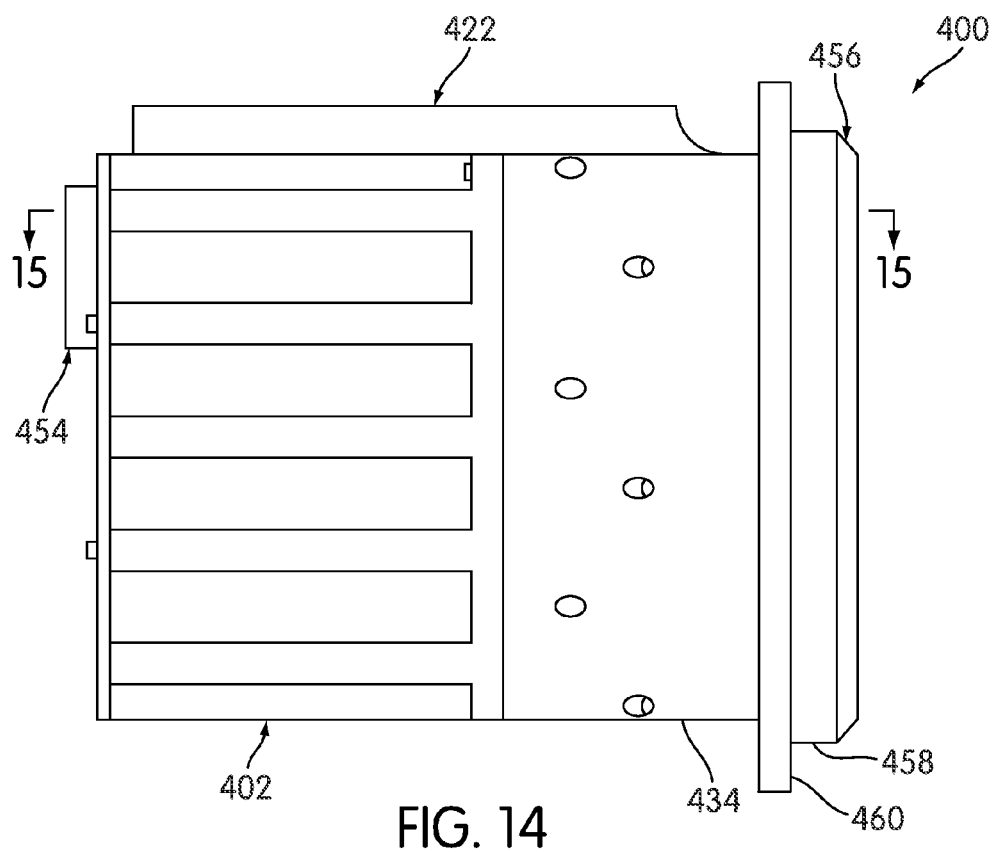
FIG. 14 is a bottom plan view of the signal detector.

Details of a signal detector 400 for use in conjunction with the present invention are shown in FIGS. 13-16. As shown in FIG. 13, which is a perspective view of a signal detector, the detector 400 includes a housing that comprises a detector housing 418 and an excitation housing 402, both connected at a right angle with respect to each other to a lens and filter, or optics, housing 434. An interface cap 456 is attached to the optics housing 438. Each of the housing components 402, 418 and 434 may be made from machined aluminum and secured to one another by suitable fasteners, such as screws, and are preferably anodized. The interface cap 456 is preferably machined from non-thermally conductive material, such as Delrin®, so as to minimize thermal conduction between the incubator 200 and the detector 400. An excitation printed circuit board ("PCB") 406 is connected to an end of the excitation housing 402, and a detector PCB 422 is connected to an end of the detector housing 418. Excitation and detector circuitry disposed on the excitation PCB 406 and the detector PCB 422, respectively, are described below. A flexible cable 454 connects the excitation PCB 406 with the detector PCB 422.

The interface cap 456 includes a rim flange 460 surrounding the periphery of the cap 456 and a dome portion 458 projecting above the rim flange 460. As shown, for example, in FIG. 12, the dome 458 of the interface cap 456 extends into the detector opening 210 formed in the bottom wall 206 of the incubator 200, and the rim flange 460 abuts the bottom portion of the bottom wall 206 surrounding the detector opening 210 so as to provide a light-tight seal between the interface cap 456 and the bottom wall 206. A gasket material may be provided between the rim flange 460 and the bottom wall 206 to further enhance the light-tight seal. Five detection openings 462 are provided in the interface cap 456.

Figure 15:
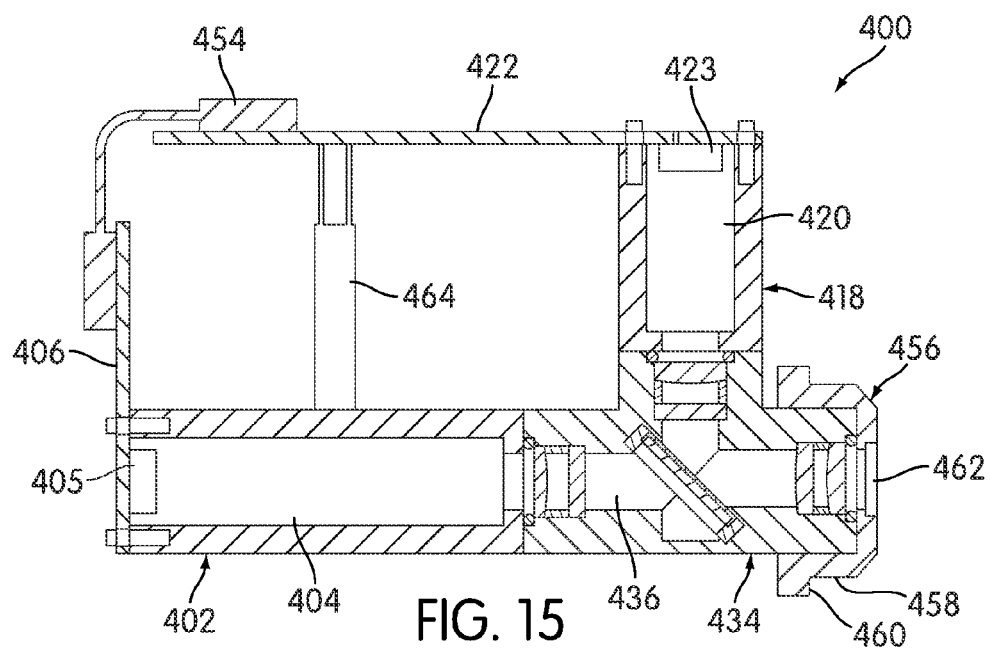
FIG. 15 is a side cross-sectional view of the signal detector taken along the line 15-15 in FIG. 14.
Figure 16:
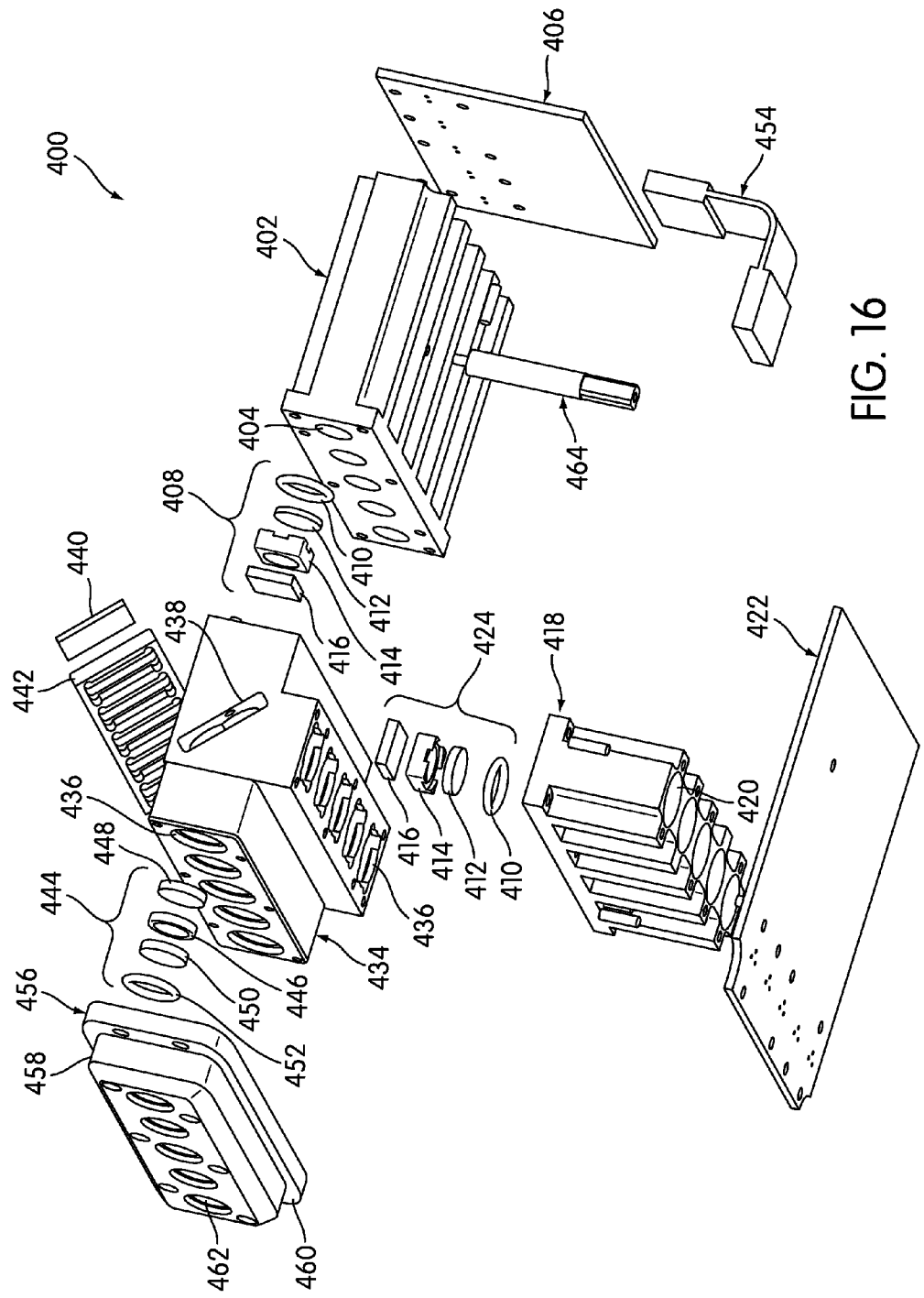
FIG. 16 is an exploded perspective view of the signal detector.

As shown in FIGS. 15 and 16, which show a side cross-sectional view and an exploded perspective view, respectively, of the signal detector, the excitation housing 402 includes five excitation channels 404. An excitation source 405, such as a light-emitting diode ("LED") coupled to the excitation PCB 406 is located at the end of each excitation channel 404. Similarly, the detector housing 418 includes five emission channels 420, and a detector element 423, such as a photodiode, is provided in each emission channel 420 and is coupled to the detector PCB 422. A standoff 406 is mounted between the excitation housing 402 and the detector PCB 422 at a distance from the detector housing 418 to provide additional stability for the detector PCB 422.

Within each individual fluorometer, or channel, of each detector 400, there are two optical paths defined by excitation optics and emission optics disposed, at least partially, within the excitation and emission channels, respectively. As described in more detail below, the excitation optical path begins with an LED as the light source, which light is collimated by an excitation lens and then filtered through an excitation filter. The filtered light passes upward through a beam splitter and is focused onto a receptacle vessel 162 by objective lenses between the receptacle vessel 162 and the beam splitter. The emission optical path originates from the light emitted by the contents of the receptacle vessel 162, which is collimated by the objective lenses as the light passes toward the beam splitter and is reflected by the beam splitter toward the emission channel. Within the emission channel, after being filtered through an emission filter, the light is focused by an emission lens onto the detector element 423, such as a photodetector.

The various optical elements of the detector 400 are located in the optics housing 434. For each excitation channel 404 of the excitation housing 402, the optics housing 434 contains excitation optics 408, for each emission channel 420 of the detector housing 418, the optics housing 434 contains emission optics 424, and for each detector opening 462 of the interface cap 456, the optics housing 434 contains input/output optics 444. The excitation optics 408, emission optics 424, and input/output optics 444 are disposed within optics channels 436 formed within the optics housing 434.

The excitation optics include an excitation lens 412, a lens holder 414, and an excitation filter 416. An O-ring 410 provides a light-tight seal between the excitation housing 402 and the optics housing 434. The excitation filter 416 is selected so as to pass excitation light from the light source 405 within the excitation channel 404 having a desired excitation characteristic (e.g., wavelength).

The emission optics include an emission lens 428, a lens holder 430 and an emission filter 432. An O-ring 426 provides a light-tight seal between the detector housing 418 and the optics housing 434. The emission filter 432 is selected so as to transmit only that portion of a signal emitted by the contents of a reaction receptacle to the detector 423 within the emission channel 420 having a desired signal characteristic (e.g., wavelength).

The input/output optics 444 include a first objective lens 450 and a second objective lens 448 with a spacer ring 446 disposed therebetween. An O-ring 452 provides a light-tight seal between the interface cap 456 and the optics housing 434.

The detector 400 further includes dichroic beam-splitters comprising dichroic beam-splitter elements 440 held within a beam-splitter frame 442 which is inserted into a beam-splitter opening 438 of the optics housing 434. A beam-splitter 440 is provided for each excitation channel 404 and corresponding emission channel 420. The beam-splitter 440 is selected so as to pass excitation light having a prescribed excitation wavelength in a straight optic path from the excitation channel 404 and to deflect emission light from the contents of the receptacle 162 having a prescribed detection wavelength toward the detection channel 420.

Figure 17:
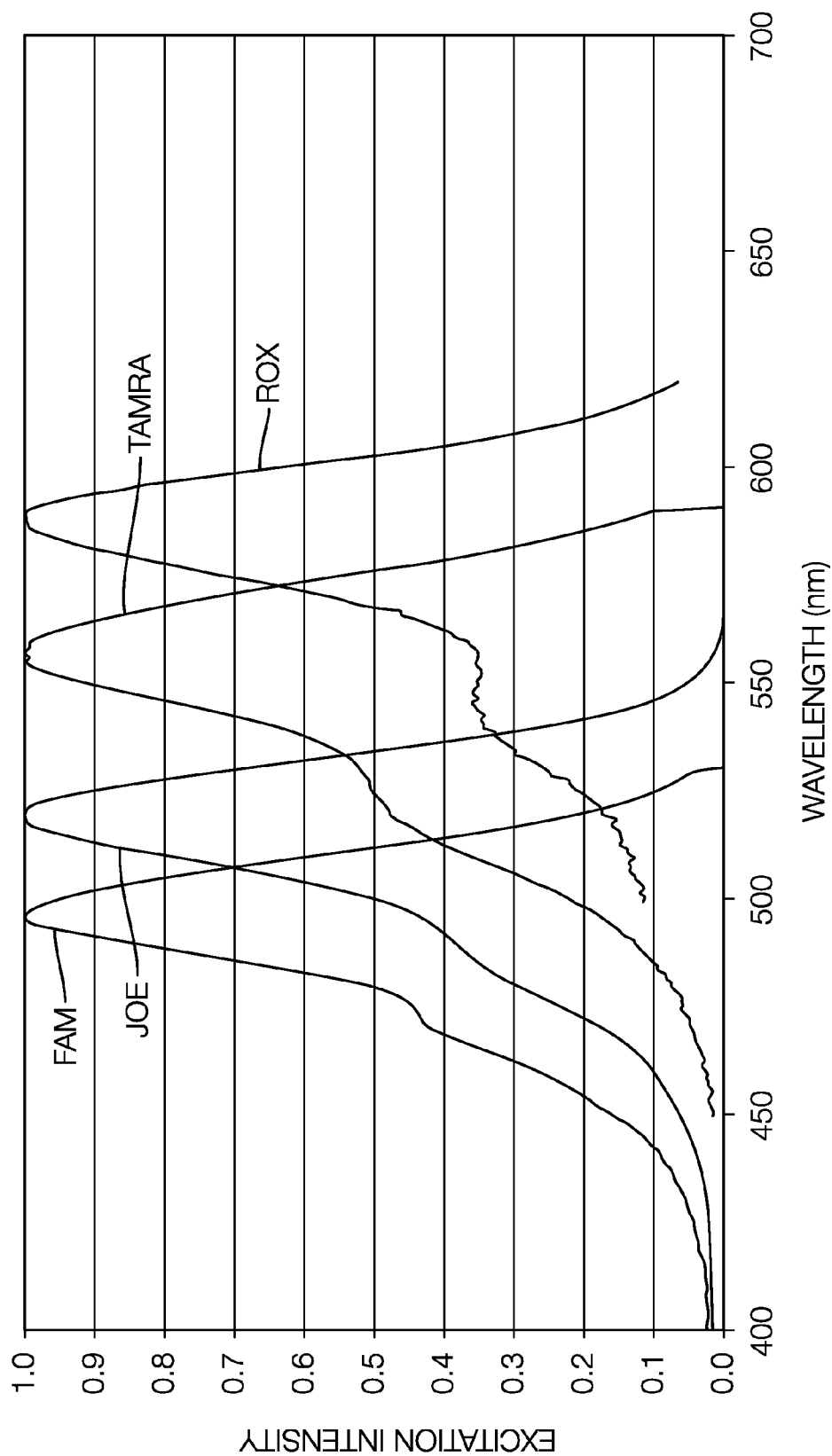
FIG. 17 is a graph showing excitation spectra of preferred amplification detection dyes.
Figure 18:
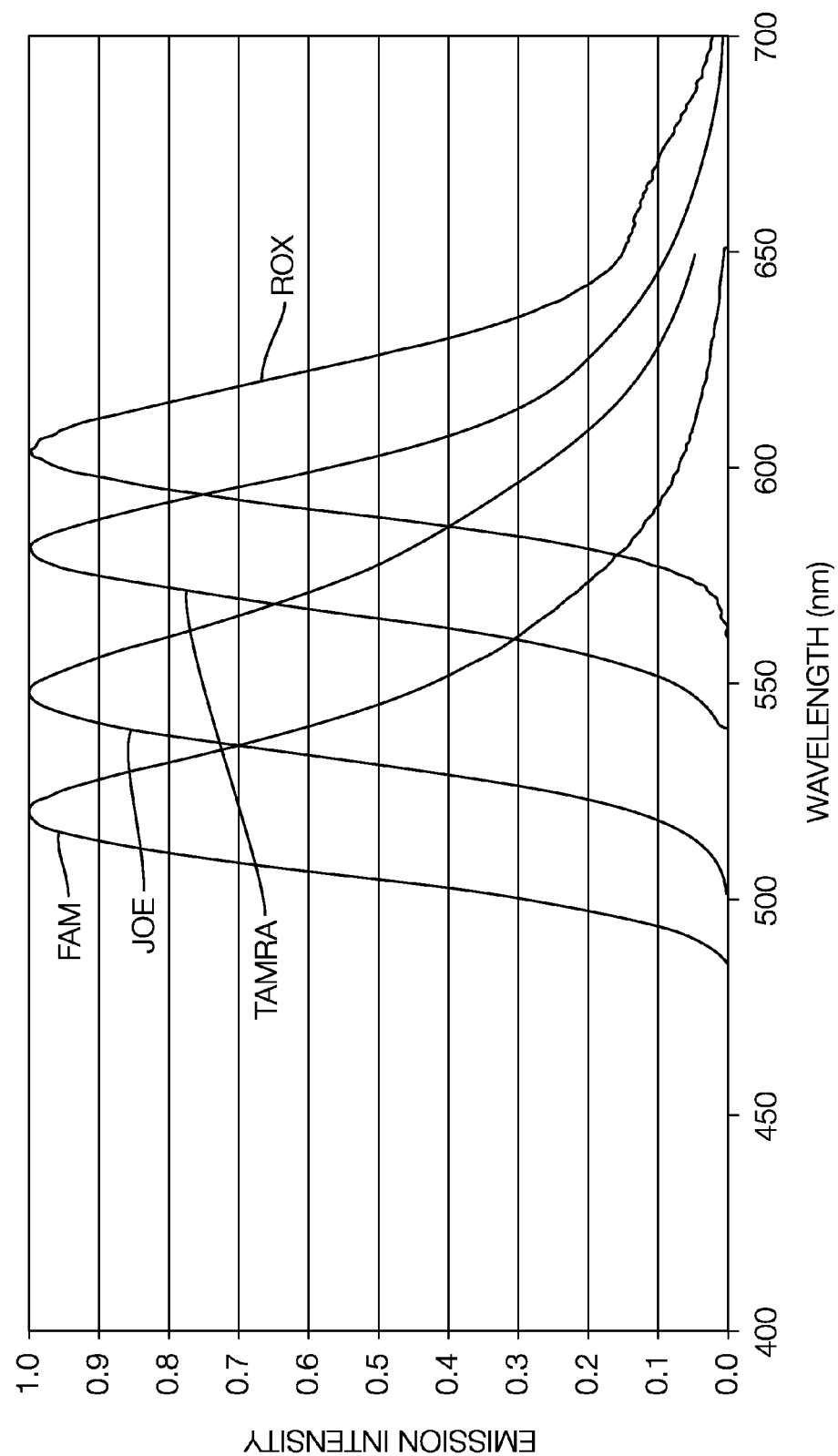
FIG. 18 is a graph showing emission spectra of preferred amplification detection dyes.

Different fluorescent dyes are excited at different wavelengths. In one multiplex application of the present invention, suitable dyes include the rhodamine dyes tetramethyl-6-rhodamine ("TAMRA") and tetrapropano-6-carboxyrhodamine ("ROX") and the fluorescein dyes 6-carboxyfluorescein ("FAM") and, each in combination with a DABCYL quencher. Additional suitable fluorescent dyes include 6-carboxy-1,4-dichloro-2',7'-dichloro-fluorescein ("TET"), 6-carboxy-4',5'-dichloro-2',7'-dimethoxy-fluorescein ("JOE"), NED, CAL FLUOR Red 610, CAL FLUOR Orange 560, Cy5, QUASAR 670, Texas Red, among others. Another suitable dye includes 5'-hexachloro-fluorescein phosphoramidite ("HEX"). A variety of additional fluorescent dyes are known in the art and can be readily employed in the methods and systems of the present disclosure. The excitation spectra of the preferred dyes are shown in FIG. 17. Because the preferred dyes are excited at different wavelengths, each detector 400 preferably emits an excitation light at or near the desired excitation wavelength (i.e., color) for the particular dye for which the optical detection module is intended. Accordingly, component selection for the optical system will, in many instances, be governed by the particular dye for which the detector 400 is intended. For example, with respect to the light source 405, the particular LED selection will depend on the dye for which the detector is intended.

The detectors 400 are often identical in design and components, with the exception of components that are dye specific. The components that are dye specific include, for example, the light source 405, the excitation filter 416, the emission filter 432, and the beam splitter 440.

The following table provides specifications for the different filters for different types of exemplary dyes:
Filter Specifications

TABLE 1

| Description | Center Wavelength (nm) | Bandwidth (nm) | Dimensions (mm) | Thickness |
|---|---|---|---|---|
| FAM Excite Filter | 460 | 60 | 8.9 × 8.9 square | 2 |
| FAM Emission Filter | 525 | 30 | 8.9 × 8.9 square | 2 |
| FAM Short Wave Pass Dichroic | | | 10 × 14.8 rectangular | 1.05 |
| HEX Excite Filter | 535 | 22 | 8.9 × 8.9 square | 2 |
| HEX Emission Filter | 567 | 15 | 8.9 × 8.9 square | 2 |

TABLE 1-continued

| Description | Center Wavelength (nm) | Bandwidth (nm) | Dimensions (mm) | Thickness |
|---|---|---|---|---|
| HEX Short Wave Pass Dichroic | | | 10 × 14.8 rectangular | 1.05 |
| ROX Excite Filter | 585 | 29 | 8.9 × 8.9 square | 2 |
| ROX Emission Filter | 632 | 22 | 8.9 × 8.9 square | 2 |
| ROX Short Wave Pass Dichroic | | | 10 × 14.8 rectangular | 1.05 |

The following table provides specifications for the different lenses corresponding to different types of dyes:

Lens and o-Ring Specifications

TABLE 2

Dye = FAM, HEX, ROX

| Part No. | Description | Vendor |
|---|---|---|
| NT47-475 | Emission Lens | Edmund or Ross |
| NT47-477 | Excitation Lens | Edmund or Ross |
| NT47-476 | Objective Lens | Edmund or Ross |
| 94115K478 | O-ring | McMaster |

The following table shows preferred characteristics for LED's for different colors:

LED Specifications

TABLE 3

| Characteristic | Blue | Green | Amber |
|---|---|---|---|
| Chip Size | 24 mil | 11 mil | 25 mil |
| Dominant Wavelength | 462 nm | 533 nm | 590 nm |
| Radiant Flux | 4 mW | 2 mW | 1.2 mW |
| Max DC forward current | 200 mA | 50 mA | 150 mA |

Note that in the illustrated embodiment, the beam splitter 440 passes the excitation light and reflects the emission light. Since the excitation channel is longer than the emission channel, this arrangement provides a narrow profile for the housing of the signal detector 400, thereby maximizing the number of detectors 400 that can be positioned at angular intervals beneath the incubator 200, as shown in FIG. 12. Spatial limitations and preferences may be accounted for in designing the excitation and emission channels, which can be interchanged from the format depicted in FIG. 12. In such an embodiment a beam splitter that reflects the excitation light and passes the emission light could be used.

Figure 19:
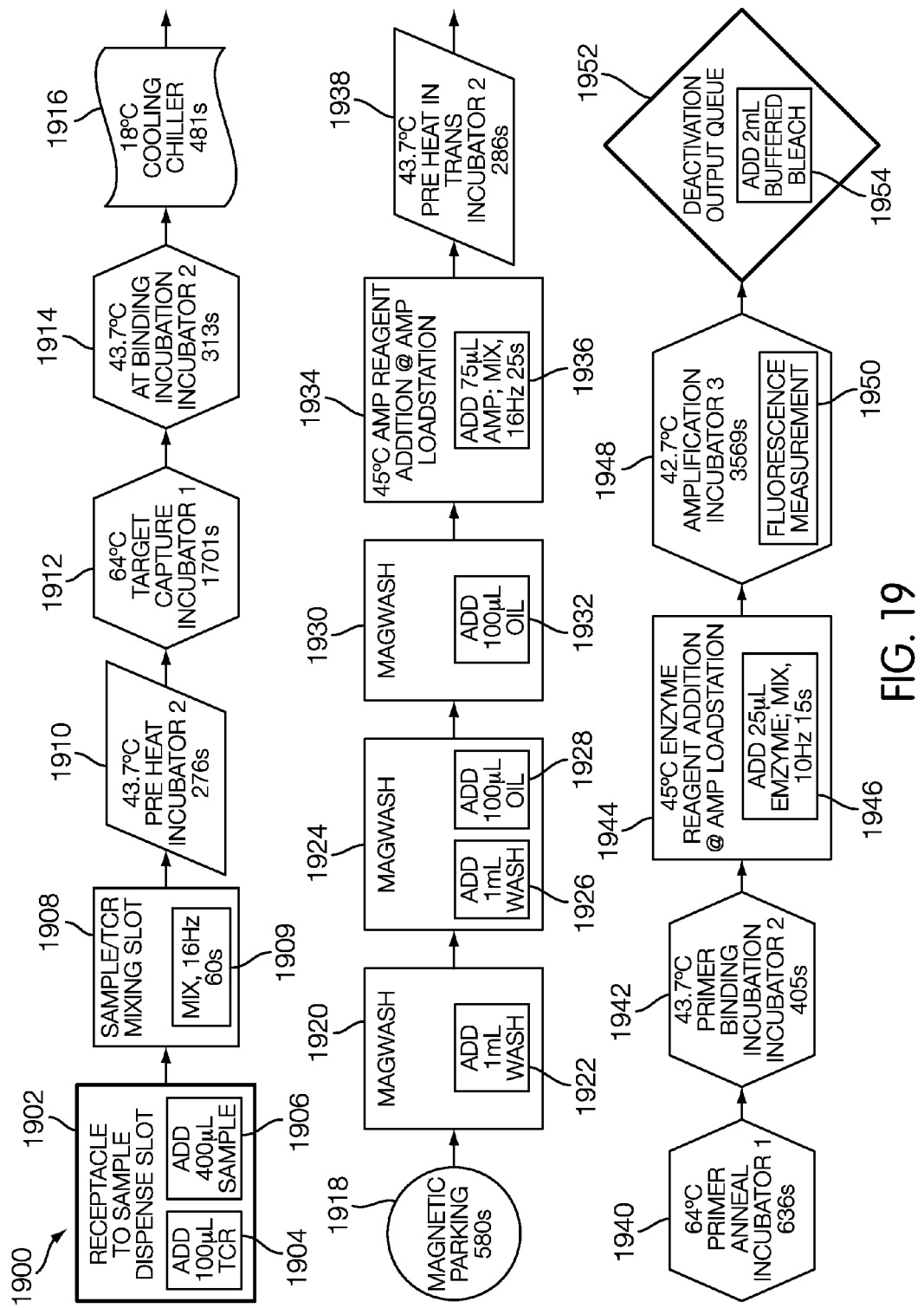
FIG. 19 is a flow chart showing the protocols of a preferred real-time amplification assay in accordance with aspects of the present invention.

The process steps of a real-time amplification assay procedure 1900 performed in accordance with aspects of the present invention are illustrated in the flow chart shown in FIG. 19. The procedure 1900 is performed by a diagnostic analyzer of which one or more incubators, such as incubator 200, is a component and which is controlled by a computer (microprocessor) executing software that includes an algorithm embodying procedure 1900 encoded or stored on a computer-readable medium. The process shown in FIG. 19 is similar to an analogous process described in detail in Lair et al., U.S. Pat. No. 8,008,066. The steps described represent exemplary TAA procedures only. Persons of ordinary skill will recognize that the steps described below may be varied or omitted or that other steps may be added or substituted in accordance with other real-time amplification assay procedures now known or yet to be developed. Reagent formulations for performing a host of amplification procedures are well known in the art and could be used in or readily adapted for use in the present invention. See, e.g., Kacian et al., U.S. Pat. No. 5,399,491; Becker et al., U.S. Pat. No. 7,374,885; Linnen et al., Compositions and Methods for Detecting West Nile Virus, U.S. Pat. No. 7,115,374; Weisburg et al., "Compositions, Methods and Kits for Determining the Presence of Trichomonas Vaginalis in a Test Sample," U.S. Pat. No. 7,381,811; and Kacian, "Methods for Determining the Presence of SARS Coronavirus in a Sample," U.S. Patent Application Publication No. 2010-0279276 A1, the disclosure of each of which is incorporated by reference.

The process steps of an exemplary real-time TAA amplification assay begin with step 1902, in which a receptacle, such as an MRD 160, is moved to a pipetting position in a sample transfer station (not shown). In step 1904, a sample pipette assembly (not shown) dispenses 100 μL of a target capture reagent ("TCR") including magnetically-responsive particles into the receptacle, e.g., into each receptacle vessel 162 of the MRD 160. The target capture reagent includes a capture probe, a detergent-containing lytic agent, such as lithium lauryl sulfate, for lysing cells and inhibiting the activity of RNAses present in the sample material, and about 40 μg Sera-Mag™ (MG-CM) Carboxylate Modified (Seradyn, Inc., Indianapolis, Ind.; Cat. No. 24152105-050250), 1 micron, super-paramagnetic particles having a covalently bound poly(dT)14. The capture probe includes a 5' target binding region and a 3' region having a poly(dA)30 tail for binding to the poly(dT)14 bound to the magnetic particle. The target binding region of the capture probe is designed to bind to a region of the target nucleic acid distinct from the regions targeted by the primers and the detection probe.

In step 1906, 400 μL of sample is dispensed into the receptacle. In step 1908, the receptacle, e.g., MRD 160, is moved to a mixer (not shown), and in step 1909, the sample and TCR are mixed, preferably at 16 Hz for 60 seconds. Note that the times given in FIG. 19 and the description thereof are desired times, and the actual times may, in practice, vary from the given desired times.

In one embodiment, the diagnostic analyzer includes three incubators maintained at three different temperatures: a first incubator maintained at 64° C. for target capture and primer annealing, a second incubator maintained at 43.7° C. for pre-heating receptacles, AT binding, and primer binding, and a third incubator maintained at 42.7° C. for amplification. The first, second, and third incubators may be configured the same as incubator 200 described above, although the first and second incubators may omit the signal detectors 400.

In step 1910, the receptacle is moved to the second incubator to pre-heat the receptacle and its contents at a temperature of 43.7° C. for 276 seconds. In other embodiments, the receptacle may be placed in a temperature ramping station (i.e., a temperature-controlled enclosure configured to receive and hold one or more receptacles (not shown)) for the pre-heating step. In step 1912, the receptacle is moved to the first incubator (i.e., target capture ("TC") incubator) where it resides at 64° C. for 1701 seconds for hybridization of the capture probe to target nucleic acids extracted from the sample (though not wishing to be bound by any particular theory, at this temperature, there will be no appreciable hybridization of the capture probe to the immobilized poly(dT)14 oligonucleotide.) In step 1914, the receptacle is moved from the TC incubator to the second incubator for AT binding where it is held for 313 seconds at 43.7° C. to allow for immobilized oligonucleotides associated with the magnetic particles to bind to the capture probes. In step 1916, the receptacle is moved to a cooling chiller (i.e., a temperature-controlled enclosure configured to receive and hold one or more receptacles (not shown)) where the receptacle is held at 18° C. for 481 seconds.

In step 1918, the receptacle is moved to a magnetic parking station (not shown), which is a structure configured to hold one or more receptacles in proximity to one or more magnets so that the contents of each receptacle vessel 162 are exposed to a magnetic field to draw the magnetically-responsive particles of the target capture reagent to a portion of the receptacle adjacent to the magnet and out of suspension. A suitable magnetic parking station is described in Davis, et al., U.S. Patent Application Publication No. 2010/0294047, "Method and System for Performing a Magnetic Separation Procedure," the disclosure of which is incorporated by reference.

In step 1920, the receptacle is moved to a magnetic separation station (not shown) for the magnetic separation wash procedure, such as is described in Lair et al., U.S. Pat. No. 8,008,066. Within the magnetic separation station, magnets, which are selectively placed in close proximity to the reaction vessel, are used to draw and hold the magnetically-responsive particles to a portion of the vessel. Once the magnetically-responsive particles, and any target nucleic acid bound thereto, are thus immobilized, the hybridized nucleic acid can be separated from non-hybridized nucleic acid by aspirating fluid from the reaction vessel. After the initial aspiration of the fluid contents from the vessel, 1 mL of wash solution is added to the receptacle in step 1922. Step 1924 comprises a second magnetic wash, which includes, after the fluid contents of the receptacle are aspirated, adding 1 mL wash solution to the receptacle in step 1926 and adding 100 µL oil (e.g., silicone oil), or other surface treating agent, to the receptacle in step 1928. In step 1930, a final magnetic wash procedure is performed (in other embodiments, more or fewer magnetic wash procedures can be performed) followed by a final dispense of 100 µL oil (e.g., silicone oil), or other surface treatment agent, in step 1932.

An advantage of adding a surface treating agent, such as silicone oil, to the sample solution in steps 1928 is that it reduces the amount of material that adheres to the inner surfaces of the reaction vessels 162 during the rinsing and aspiration steps of a magnetic separation wash procedure, thereby facilitating a more effective magnetic separation wash procedure. Although the MRDs 160 are preferably made of a hydrophobic material, such as polypropylene, small droplets of material, such as wash solution, may still form on the inner surfaces of the MRD receptacle vessels 162 during the aspiration steps of a magnetic separation wash procedure. If not adequately removed from the receptacle vessels 162 during the magnetic separation wash procedure, this residual material, which may contain nucleic acid amplification inhibitors, could affect assay results. In alternative approaches, the surface treating reagent could be added to the receptacle vessels 162 and removed prior to adding TCR and sample or the surface treating agent could be added to the reaction tubes after TCR and sample have been aspirated from the reaction tubes, possibly with the wash solution, and then removed prior to adding amplification and enzyme reagents to the reaction tubes. The objective is to provide inner surfaces of the receptacle vessels 162 with a coating of the surface treating agent Inhibitors of amplification reactions are known in the art and depend on the sample source and amplification procedure to being used. Possible amplification inhibitors include the following: hemoglobin from blood samples; hemoglobin, nitrates, crystals and/or beta-human chorionic gonadotropin from urine samples; nucleases; proteases; anionic detergents such as sodium dodecyl sulfate (SDS) and lithium lauryl sulfate (LLS); and EDTA, which is an anticoagulant and fixative of some specimens that binds divalent cations like magnesium, which, as noted above, is a cofactor used in nucleic acid-based amplification reactions. See, e.g., Mahony et al., J. Clin. Microbiol., 36(11):3122-2126 (1998); Al-Soud, J. Clin. Microbiol., 39(2):485-493 (2001); and Kacian et al., "Method for Suppressing Inhibition of Enzyme-Mediated Reactions By Ionic Detergents Using High Concentration of Non-Ionic Detergent," U.S. Pat. No. 5,846,701, the disclosure of each of which is incorporated by reference. Silicone oil is added to each reaction vessel 162 of the MRD 160 in step 1932 to prevent evaporation and splashing of the fluid contents during subsequent manipulations.

In step 1934, amplification reagent, which is stored in a chilled environment, is added to each receptacle while the receptacle is held at 45° C. at an amplification load station (not shown). In step 1936, 75 mL of an amplification reagent are dispensed into the receptacle disposed within the load station, and the receptacle is then mixed for 25 seconds at 16 Hz by a mixer incorporated into the load station. For the exemplary TAA reactions, the amplification reagents contain an antisense promoter-primer having a 3' target binding region and a 5' promoter sequence recognized by an RNA polymerase, a sense primer that binds to an extension product formed with the promoter-primer, nucleoside triphosphates (e.g., dATP, dCTP, dGTP, dTTP, ATP, CTP, GTP and UTP, including modified nucleotides or nucleotide analogs), and cofactors sufficient to perform a TAA reaction. For the real-time TAA amplification assay, the amplification reagent also contains strand displacement, molecular torch probes having interacting label pairs (e.g., interacting fluorescent and quencher moieties joined to the 5' and 3' ends thereof by conventional means) and a target specific region capable of detectably hybridizing to amplification products as the amplification is occurring and, preferably, not to any non-target nucleic acids which may be present in the receptacles. See Kacian et al., U.S. Pat. No. 5,399,491; Becker et al., "Single-Primer Nucleic Acid Amplification," U.S. Pat. No. 7,374,885 (disclosing an alternative TAA-based amplification assay in which an antisense primer and a sense promoter oligonucleotide blocked at its 3' end are employed to minimize side-product formation); and Becker et al., U.S. Pat. No. 6,361,945, the disclosure of each of which is incorporated by reference.

In step 1938, the receptacle is moved to the second incubator and preheated at 43.7° C. for 286 sec. In step 1940, the receptacle is moved to the first incubator and incubated at 64° C. for 636 seconds for primer annealing. In step 1942, the receptacle is moved to the second incubator and incubated for 405 seconds at 43.7° C. for binding of the promoter-primer to a target nucleic acid. The preferred promoter-primer in this particular TAA example has a promoter sequence recognized by a T7 RNA polymerase.

In step 1944, the receptacle is moved to the load station for enzyme reagent addition at 45° C. In step 1946, 25 µL of enzyme are added and the MRD is mixed at 10 Hz for 15 seconds. In step 1948, the receptacle is moved to the third incubator (amplification incubator), where the receptacle contents are incubated at 42.7° C. for 3569 seconds for amplification. During amplification, real-time fluorescence measurements are taken in step 1950. The enzyme reagent of this example contains a reverse transcriptase and a T7 RNA polymerase for performing TAA.

After the nucleic acid-based assay is complete, and to avoid possible contamination of subsequent amplification reactions, the reaction mixture can be treated with a deactivating reagent which destroys nucleic acids and related amplification products in the reaction vessel. In such an example, following amplification and real-time measurements, in step 1952, the receptacle is moved to a deactivation queue, or module (not shown), and, in step 1954, 2 mL of a bleach-based agent are provided to each receptacle to deactivate nucleic acid (i.e., alter the nucleic acid such that it is non-amplifiable) present in the receptacle. Such deactivating agents can include oxidants, reductants and reactive chemicals, among others, which modify the primary chemical structure of a nucleic acid. These reagents operate by rendering nucleic acids inert towards an amplification reaction, whether the nucleic acid is RNA or DNA. Examples of such chemical agents include solutions of sodium hypochlorite (bleach), solutions of potassium permanganate, formic acid, hydrazine, dimethyl sulfate and similar compounds. More details of a deactivation protocol can be found in, e.g., Dattagupta et al., U.S. Pat. No. 5,612,200, and Nelson et al., U.S. Patent Application Publication No. US 2005-0202491 A1, the disclosure of each of which is hereby incorporated by reference.

As noted above, the incubator 200 includes a number of signal detectors 400 configured to measure in real time the concentration of unquenched fluorescent dye molecules located in the MRD 160. As discussed above, the assay is designed such that the fluorescent signal increases as the concentration of the target is increased by amplification. The detectors 400, therefore, may be used to monitor the amplification process by monitoring the emergence of the fluorescent signal.

As also noted above, incubator 200 may include between 3 and 6 detectors 400. Each of the detectors 400 can itself have a number of fluorometers. For instance, according to some embodiments of the present invention, each detector 400 includes five fluorometers, or channels. Preferably there are as many fluorometers as there are receptacles 162 in the MRD 160. Each fluorometer, or channel, includes two optical paths: an excitation path and an emission path.

Optical crosstalk between adjacent channels of a single signal detector 400 and/or between adjacent signal detectors 400 can take a number of forms. Crosstalk can occur when one channel detects the excitation light from another channel (of the same or different signal detector 400) or when one fluorometer picks up emission light from a receptacle 162 that is excited by a different fluorometer. In addition, crosstalk can occur when an excitation signal for a particular dye color excites a dye of a color that is not intended for that fluorometer. For example, as shown in FIG. 17, which shows excitation intensity versus wavelength for several different fluorescent dyes, the excitation wavelengths of FAM and JOE, JOE and TAMRA, and TAMRA and ROX overlap to a certain extent.

Figure 24:
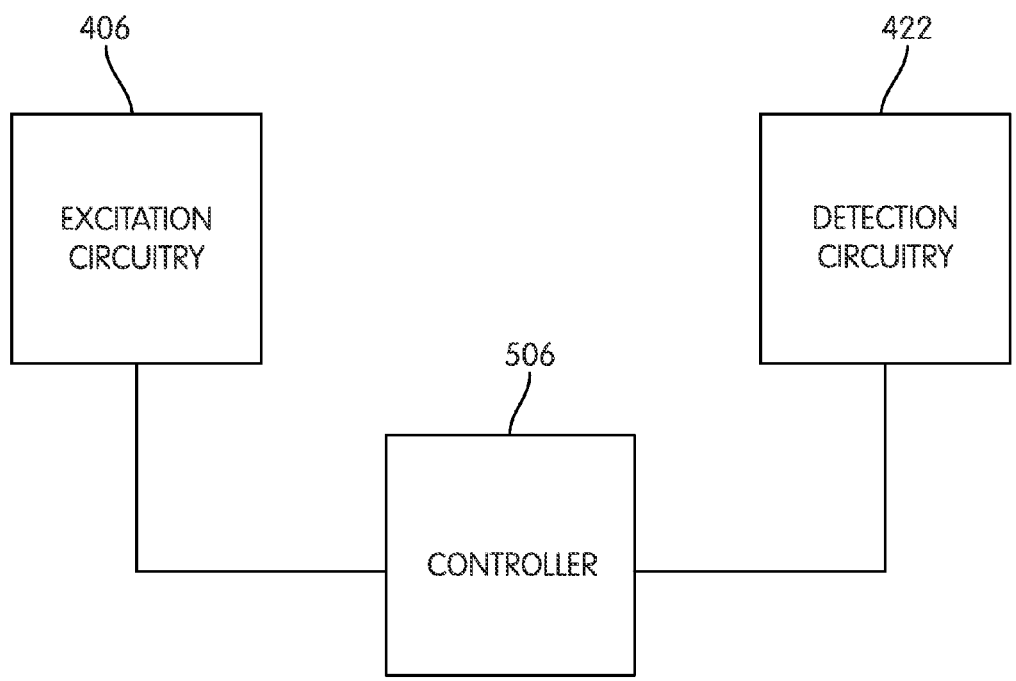
FIG. 24 is a block diagram schematically illustrating excitation and detection architecture.

The data acquisition system and process can be described at a high level with reference to FIG. 24. In general, the system and process include three components: excitation 406, detection 422, and control 506. In the Excitation branch 406, a power source generates an alternating current ("AC") waveform (e.g., square or sinusoidal) from a voltage-controlled current source and sends that waveform to the light source (e.g., an LED) to generate an excitation light signal that is modulated in a manner corresponding to the AC wave form. The detection branch 422 includes a light detector (e.g., a photodiode) that converts photons of light that impinge on the detector to a current. The detection branch 422 further includes a component, such as a transimpedance amplifier, that converts the current from the light detector into a voltage having a waveform that is the analog of the photons that impinge on the light detector. The control branch, or controller, 506 includes, among other components, an analog to digital (A/D) converter and a demodulator. The A/D converter converts the analog voltage into digital data, and the demodulator identifies the frequency components of the digital data by digital signal processing ("DSP") techniques, such as those described below, and, in particular, identifies the component of the digital data having a frequency corresponding to the frequency of the AC waveform that was used to drive the excitation signal.

Synchronous detection is one means for reducing some forms of crosstalk. Other means for reducing crosstalk include the use of narrow bandwidth spectrum filters for conditioning excitation and emission light, focusing elements (e.g., lenses or narrow apertures) for providing a spatially tight excitation and/or emission beam, and isolating elements for optically isolating signal detectors from one another. Synchronous detection creates a narrow bandwidth frequency filter that is sensitive to only a narrow range of frequencies in the emission signal centered at a modulation frequency of the excitation signal. In this process, each photodetector 423 is connected to a transimpedance amplifier on the detector PCB 422, and each LED light source 405 is connected to a DAC controlled current source on the excitation PCB 406. The LED current is modulated. The signal from the photodiode at the output of the transimpedance amplifier is demodulated at the modulation frequency of the LED forming a synchronous detection system that can reject cross-talk signals and ambient light.

In addition to cross-talk, synchronous detection also greatly reduces the noise due to other sources, such as ambient light, allowing the use of an incubator that is not light-tight (i.e., permitting a certain amount of ambient light entry into the interior of the incubator). Using synchronous detection, the system is sensitive to signals that are at the modulation frequency of the excitation signal and is insensitive to signals that are not at the excitation modulation frequency. Ambient light is typically not at the modulation frequency of the system and so it is rejected or not measured. For example, sunlight is not modulated; it is DC, so that its intensity is not frequency-dependent. Also, interior room lights are typically modulated at 50, 60, 100, or 120 Hz. Thus, by setting modulation frequencies of the excitation signals away from typical frequencies that would be produced by ambient light, the system becomes insensitive to the ambient light.

Crosstalk between emission signals of neighboring receptacles 162 of an MRD 160 can occur because the emission channels 420 and excitation channels 404 of the signal detector 400 are arranged in close proximity to one-another, e.g., as closely-adjacent channels arranged in a row. Two methods are used to reduce this type of crosstalk. For example, the optics are designed to have a narrow excitation and detection spot 2 mm in width. The emission optical path of the signal detector 400 accepts light in a narrow range of angles within this small spot. This reduces the amount of light that can leak between adjacent receptacles 162 of the MRD 160. In addition to the optical means, the synchronous detection system is used to reduce this type of cross talk as well. The modulation frequency of the excitation signal of each of the five excitation channels 404 of the signal detector 400 is set at one of two frequencies, for example, that alternate between adjacent channels. For example, the modulation frequency of the excitation signal of the first channel corresponding to the first receptacle 162 is set to frequency A, the modulation frequency of the excitation signal of the second channel corresponding to the second receptacle 162 is set to frequency B, the modulation frequency of the excitation signal of the third channel corresponding to the third receptacle 162 is set to frequency A, the modulation frequency of the excitation signal of the fourth channel corresponding to the fourth receptacle 162 is set to frequency B, and the modulation frequency of the excitation signal of the fifth channel corresponding to the fifth receptacle 162 is set to frequency A, where frequency A and frequency B are set to values that are far enough apart that each channel is insensitive to its neighbors. Specifically, for the FAM signal detector, the modulation frequency is set to 200 Hz for the first, third and fifth receptacles 162 and to 250 Hz for second and fourth receptacles 162.

Figure 30:
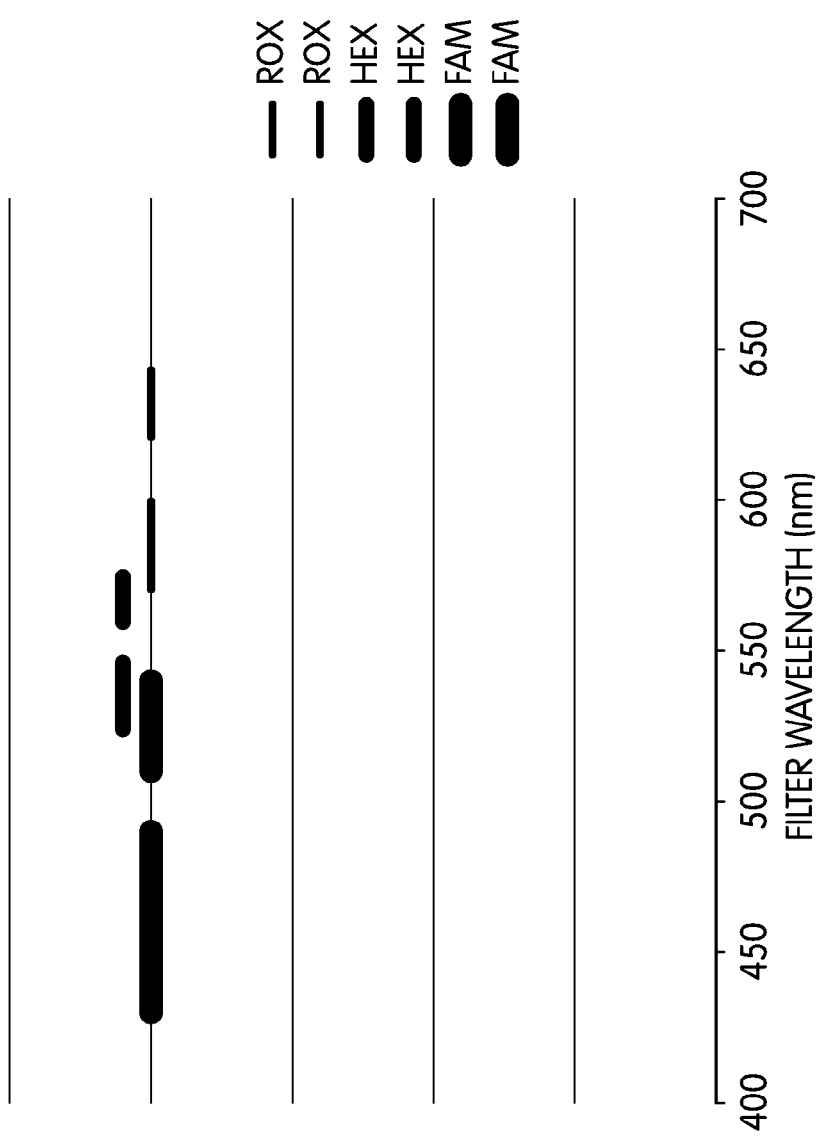
FIG. 30 shows the bandwidths of excitation and emission filters used in optical signal detectors for detecting different fluorescent dyes.
Figure 31:
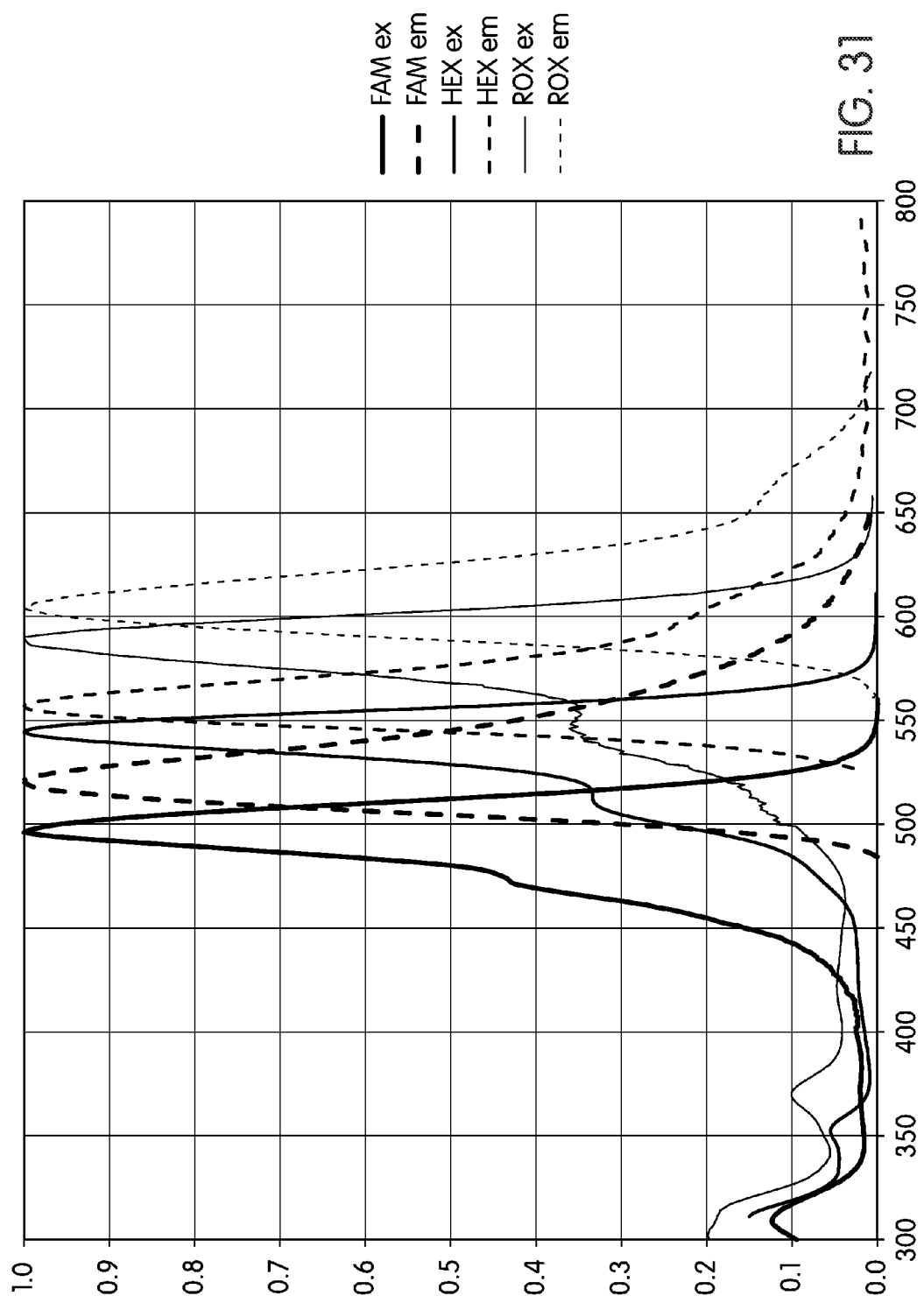
FIG. 31 is a graph showing excitation and emission fluorescence spectra for FAM, HEX, and ROX dyes.

Crosstalk can also occur between detection of one color and excitation of another color. For example, the FAM emission filter overlaps with the HEX excitation filter such that the excitation light of HEX can be detected by the FAM fluorometer. This is not the case for the HEX detector and the FAM excitation, because these two filters do not overlap. Crosstalk between detection and excitation of adjacent colors is reduced by two methods. One is to arrange the band pass of the filters, where possible, so that they don't overlap. As the filter bandwidth is widened, a broader spectrum of light passes through the filter, and more signal can be obtained, but the amount of cross-talk also generally increases. Accordingly, the filter bandwidth can be adjusted to provide for a balance between crosstalk and signal strength to permit detection of a clear emission signal. As shown in FIG. 30, which shows the bandwidths of excitation and emission filters for ROX, HEX, and FAM dyes (for each dye, the excitation bandwidth is to the left of the emission bandwidth), the spectral bandwidths of FAM and ROX filters preferably do not overlap. As shown in FIG. 31, which shows normalized excitation and emission fluorescence versus wavelength for FAM, HEX, and ROX dyes, the HEX excitation wavelength band partially overlaps with FAM emission wavelength band, and the ROX excitation wavelength band partially overlaps with HEX emission wavelength band. See also Table 1 above. For acceptable performance, it is preferable that the FAM emission and HEX excitation filters overlap because they are very closely spaced. Typically there is overlap in filters between colors that are close, so in the progression of colors from FAM to HEX to ROX, there is overlap between FAM emission and HEX excitation and between HEX emission and ROX excitation, but not between FAM (excitation or emission) and ROX (excitation and emission).

Synchronous detection is used to reduce the crosstalk between neighboring colors as follows. The alternating of two modulation frequencies was already described to eliminate crosstalk between the neighboring receptacles 162. In this case, the same method is used; two modulation frequencies, different from the modulation frequencies used for the FAM signal detector, are selected for the HEX signal detector and are alternated between receptacles 162, and then the FAM modulation frequencies are used for the ROX signal detector. This arrangement is outlined below in Table 4:

TABLE 4

| Dye | Receptacle 1 | Receptacle 2 | Receptacle 3 | Receptacle 4 | Receptacle 4 |
|---|---|---|---|---|---|
| FAM | 200 Hz | 250 Hz | 200 Hz | 250 Hz | 200 Hz |
| HEX | 300 Hz | 350 Hz | 300 Hz | 350 Hz | 300 Hz |
| ROX | 200 Hz | 250 Hz | 200 Hz | 250 Hz | 200 Hz |

Figure 25:
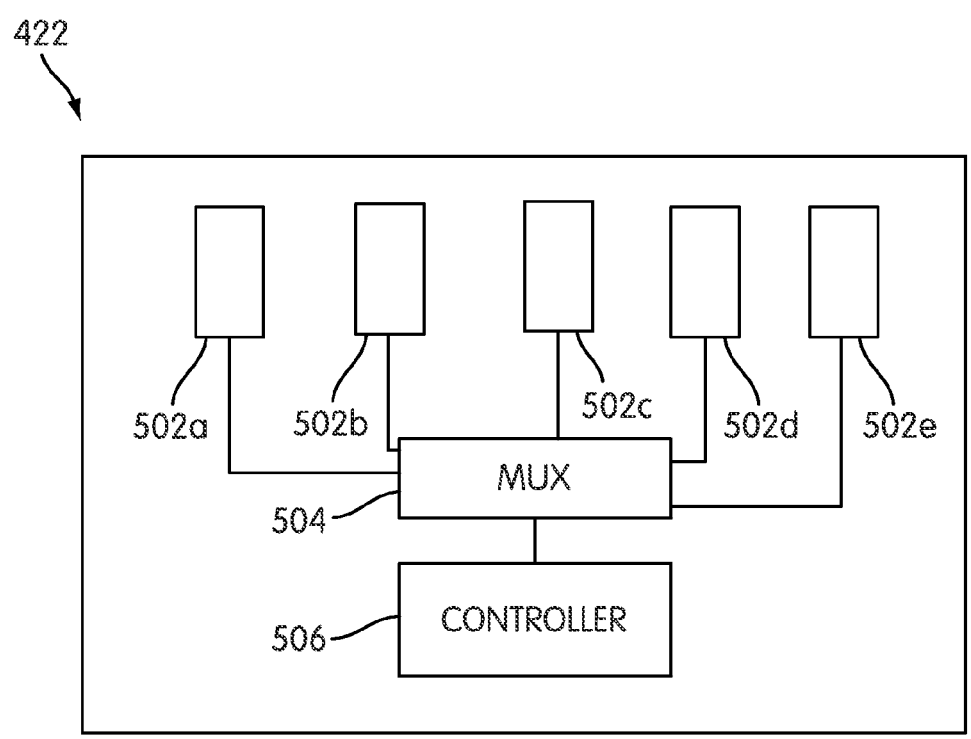
FIG. 25 is a block diagram schematically illustrating an arrangement of detection circuitry embodying aspects of the invention.

FIG. 25 depicts a logical block diagram of an arrangement of the detection circuitry 422 according to embodiments of the present invention. The detection circuitry on the detector PCB 422 can include detector circuits 502a-502e, which are configured to detect fluorescent light and to convert the detected light to a voltage signal that can be processed by the controller 506. The output from the detector circuits 502a-502e can be connected to controller 506 either directly or through a multiplexer 504, as is shown in FIG. 25.

Figure 27:
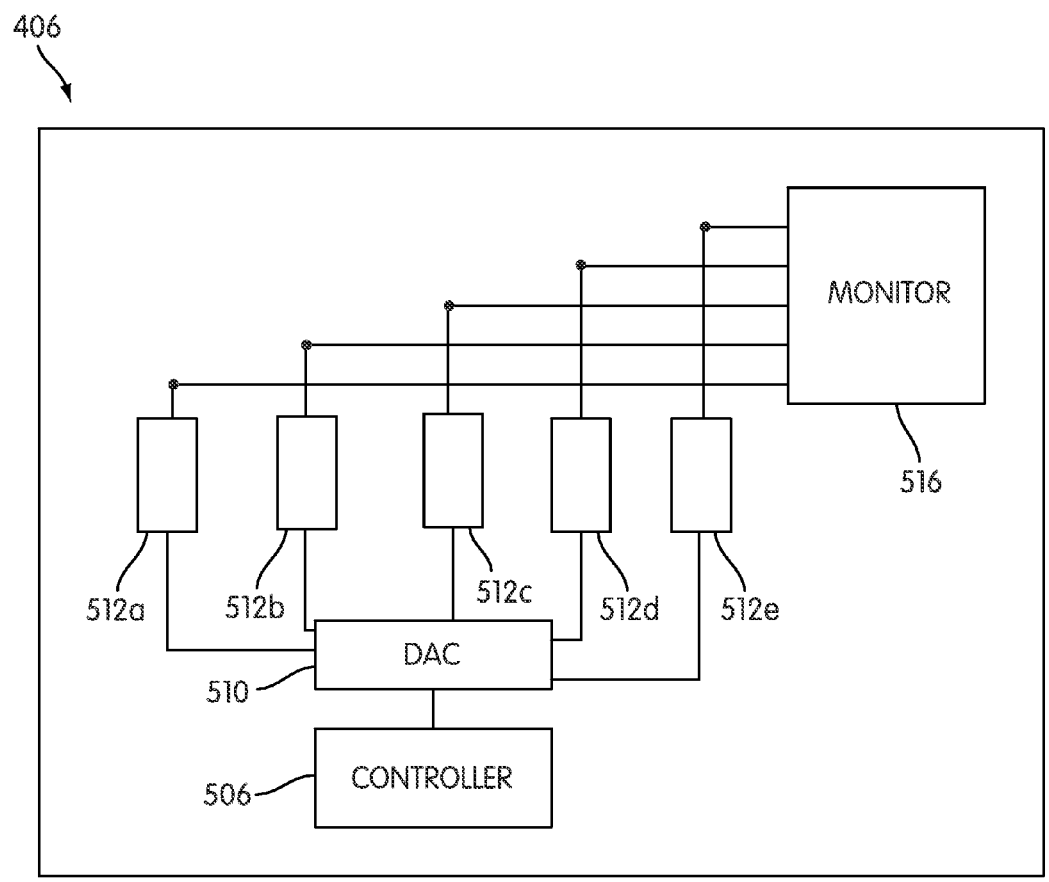
FIG. 27 is a block diagram schematically illustrating an arrangement of excitation circuitry embodying aspects of the invention.

FIG. 27 depicts a logical block diagram of an arrangement of the excitation circuitry according to embodiments of the present invention. As shown in FIG. 27, which is a block diagram schematically illustrating an arrangement of excitation circuitry embodying aspects of the invention, excitation circuitry can include the controller 506 and a digital to analog converter (DAC) 510. The excitation circuitry on the excitation PCB 406 includes excitation circuits 512a-512e for driving each excitation source 405 of each excitation channel 404. The excitation circuits 512a-512e are driven by a digital to analog converter (DAC) controlled current source. The current source is a voltage to current amplifier that controls the current flowing through the excitation source 405.

A monitor 516 can be connected to excitation circuits 512a-512e to facilitate process control of the excitation voltage. Checking the voltage across the LED and the current through the LED give a good indication if the LED is functioning correctly. This is a diagnostic capability that can be used in a variety of ways. For example, the LED could be checked at power-on, during a self-test, so when the fluorometer powers up it could put a known current through the LED, and if the forward voltage of the LED is in and expected range, then the system would pass the self-test. These values could also be checked during an assay to monitor correct functioning of the LED.

Figure 28:
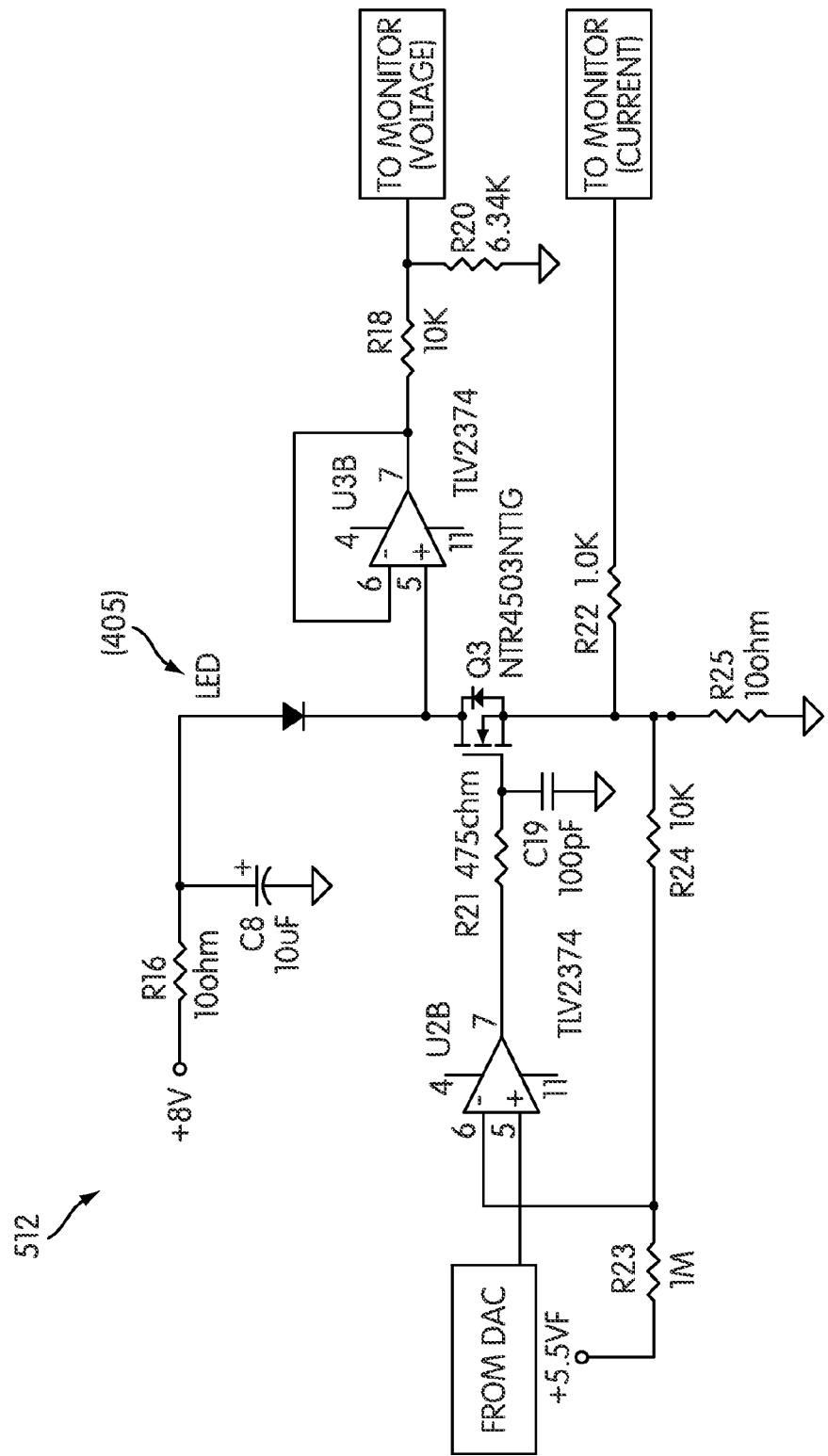
FIG. 28 is a circuit diagram illustrating a fluorometer excitation circuit embodying aspects of the invention.

According to embodiments of the invention, each of the LEDs (corresponding to excitation source 405) in circuits 512a-512e can be driven by a digital to analog converter controlled current source, as shown in FIG. 28, which is a circuit diagram illustrating a fluorometer excitation circuit. The current source can be a voltage to current amplifier that controls the current flowing through LED (corresponding to excitation source 405).

In addition to performing the function of driving a computer controlled current waveform through the LED, the current source shown in FIG. 28 allows for process control based on LED current and voltage. The output of the circuit formed by U3 is a monitor of the voltage across the LED and can be digitized by monitor 516 using an A/D converter. Similarly the output of R22 (the side away from transistor Q3) can be used to monitor the current passing through the LED and similarly digitized by an A/D converter located in monitor 516. The current through the LED is monitored for diagnostic purposes, as described above.

Figure 26A:
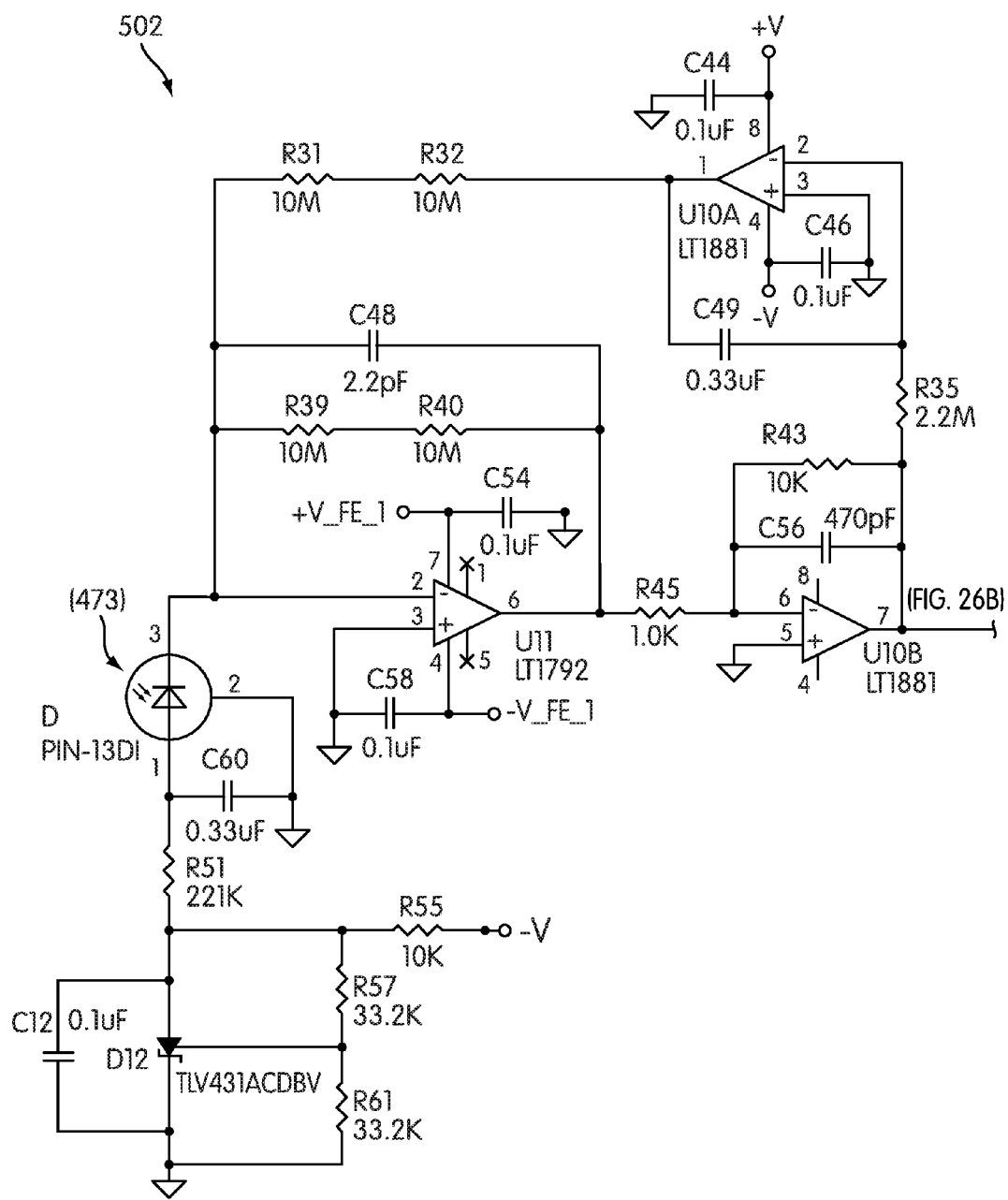
FIGS. 26A and 26B are two parts of a circuit diagram illustrating a fluorometer detection circuit embodying aspects of the invention.
Figure 26B:
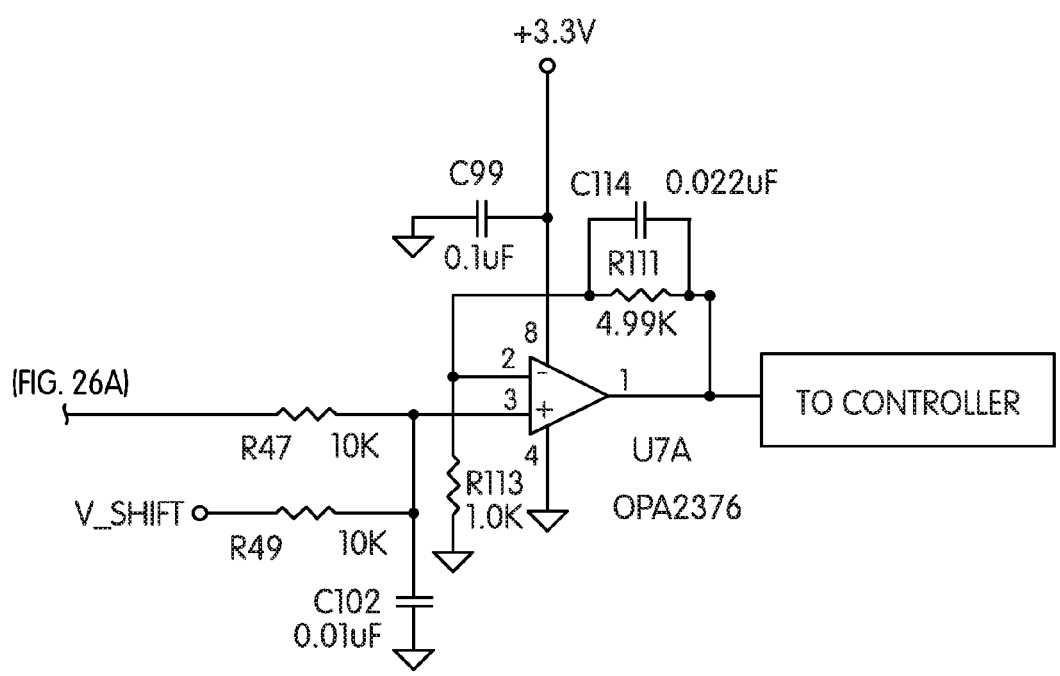

The fluorometer circuits 502a-502e could be configured as shown in FIGS. 26A and 26B. Each detector circuit 502 includes a pre-amplifier circuit, which includes U11, and the amplifier formed by pins 5-7 of U10 (designated as U10B). The pre-amplifier circuit receives current from the photodiode D (corresponding to detector element 423) and converts it to an amplified voltage. As shown, the amplifier that includes pins 1-3 of U10 (designated as U10A) provides a bias current to compensate for the electrical current out of photodiode D caused by un-modulated ambient light incident on the photodiode D. As with circuitry 1790, this is to prevent the ambient light from saturating the output of the pre-amplifier.

Amplifiers U11 and U10B form the first two stages of amplification of the current signal (corresponding to the emission signal) from the photodiode D (423). C54, C44, and C58 provide power supply bypassing/filtering to the amplifiers. C12, D12, R55, R57, and R61 form a filtered power supply that biases the anode of the photodiode D. Feedback resistors R31 and R32 convert electrical current from the photodiode D into a voltage while C48 provides filtering for higher frequency signals. The voltage divider formed by R43 and R45 provides a voltage gain of 10 in the next pre-amplification state while capacitor C56 provides additional low pass filtering.

The detector circuits 502a-502e are configured to use a level shifter formed by U7A. Though not wishing to be bound by theory, the purpose of the level shifter is to move the zero level of the pre-amp up to the middle range of a unipolar analog to digital converter. This allows the use of A/D converters employed by certain microcontrollers so that an additional A/D converter is not required.

The circuit configuration shown in FIGS. 26A and 26B does not require a demodulator circuit. Instead, the detection circuitry of the detector PCB 422 can employ five identical preamplifier circuits on the controller board. The output of each of the preamplifier circuits can then connect directly to the A/D converter input of the controller 506. This allows synchronous detection to be accomplished by DSP using an algorithm executed in the microcontroller 506, instead of using an analog demodulator and filter circuit as in synchronous detection circuits.

According to some embodiments, the signal from each of the detector circuits 502a-502e is digitized at a rate that is at least twice the modulation frequency of the excitation source 405, preferably substantially more than twice the modulation frequency. For instance, in one implementation, the modulation frequency is around 250 Hz, and the digitization rate is 4 kHz. According to some embodiments, the microcontroller 506 identifies frequency components of an emission signal by executing a Goertzel algorithm modified as described below. The amplitude of the frequency component that matches the excitation modulation frequency can then be calculated, thus identifying the emission signal that is due to the intended excitation signal and digitally "filtering" out signal components due to cross-talk and ambient light.

In other embodiments, however, the digitized signal is processed by any of a number of different algorithms for identifying the amplitude of a specific frequency component, including discrete Fourier transform (DFT), Fast Fourier transform (FFT), or digital lock-in detection.

The Goertzel algorithm employed is a digital signal processing technique for identifying frequency components of a signal, published by Dr. Gerald Goertzel in 1958. While the general Fast Fourier transform algorithm computes evenly across the bandwidth of the incoming signal, the Goertzel algorithm detects frequencies in a single frequency band and is more efficient than the FFT. The modified Goertzel Algorithm calculates the frequency component using the last 2 terms of the filter and normalizes the output to be independent of the number of samples.

Figure 23:
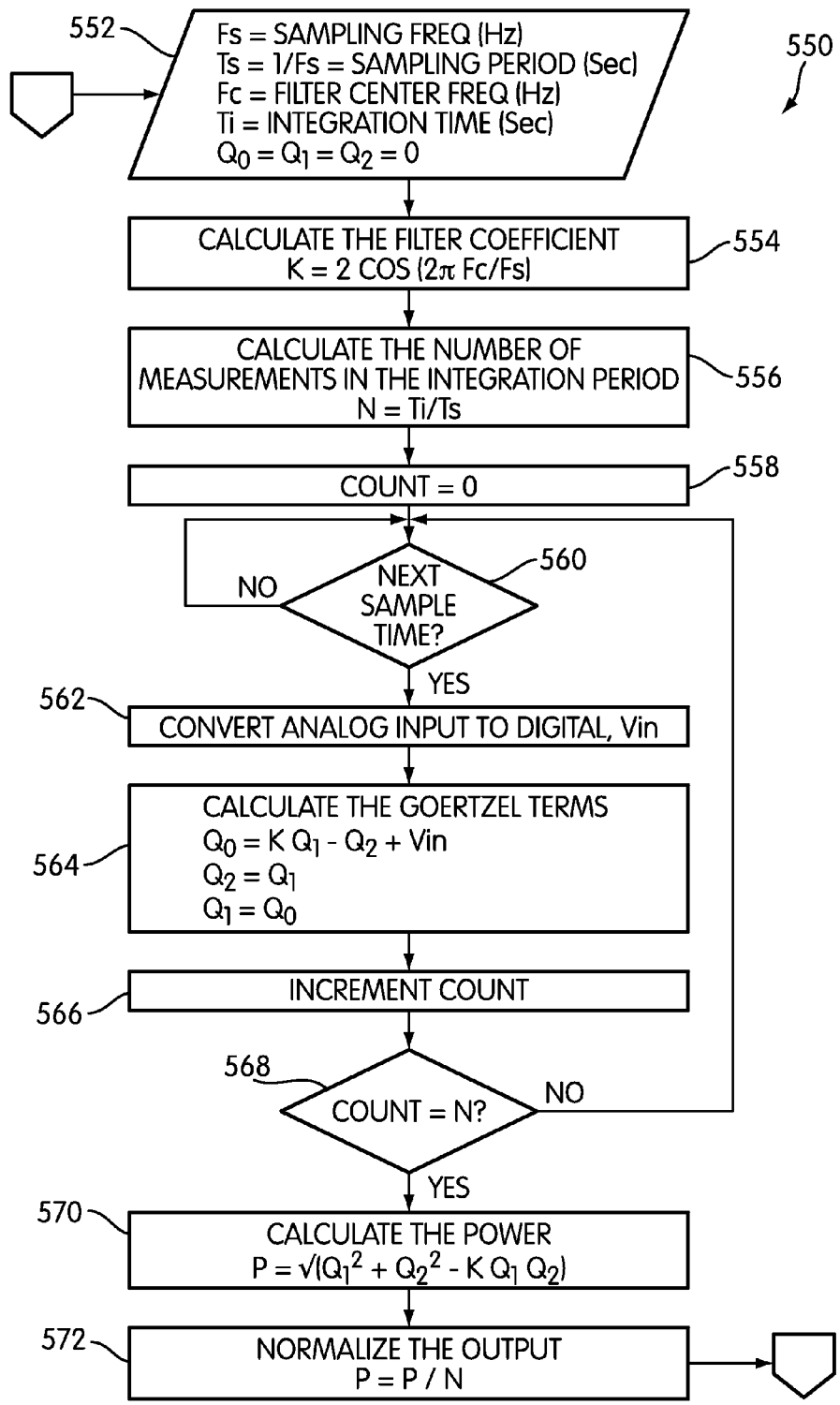
FIG. 23 is a flow chart illustrating an algorithm for performing phase synchronous detection of an emission signal from the contents of a reaction receptacle to detect the frequency component of the emission signal that is due to the correct excitation signal.

In embodiments of the invention that employ the modified Goertzel algorithm, the power of a signal at a certain frequency can be calculated according to method 550 depicted in FIG. 23, which can be implemented by means of software stored on a computer-readable medium and executed by a microprocessor (i.e., a programmed computer), such as controller 506. According to method 550, several variables are initialized at step 552. Fs is initialized to the frequency at which the signal is sampled (i.e., the digitization frequency). Ts is set to the sampling period, or 1/Fs. Fc is set to the center frequency of the filter in Hz (i.e., the modulation frequency for excitation of the particular dye being detected). Ti is initialized to an integration time. Preferably, a center frequency Fc is chosen that is an integer multiple of the sampling period Ts, and an integration time Ti is chosen that is an integer multiple of the center frequency Fc, since it has been found that choosing such center frequencies and integration times minimizes digital processing noise. Finally, the Goertzel terms $Q_0$, $Q_1$, and $Q_2$ are set to zero.

At step 554, a filter coefficient K is calculated using the following formula:

$$K=2\cos(2\pi F_c/F_s)$$

With the filter coefficient K calculated, at step 556 the number of measurements in the integration period N can then be calculated by dividing the integration period Ti by the sampling period Ts, and the "COUNT" variable can be set to zero at step 558. Step 560 pauses the process until the next sample time has elapsed. At the next sample time, the analog output from the detector circuit 502 is converted to a digital input Vin at step 562. At step 564, the Goertzel terms are recalculated in the following order:

$$Q_0=KQ_1-Q_2+Vin$$

$$Q_2=Q_1$$

$$Q_1=Q_0$$

That is, first $Q_0$ is calculated, then $Q_2$ is set to the current value of $Q_1$, and then $Q_1$ is reset to the newly calculated value of $Q_0$.

Since the basic Goertzel Algorithm is essentially a discrete Fourier transform ("DFT") that produces a sequence of terms related to a single frequency of interest, the algorithm is "modified" in the current implementation by the following steps:

The counter is incremented at step 566, and it is determined whether N measurements have been taken at step 568. If N measurements have not been taken, then the method loops back to step 560. If N measurements have been taken, then the power P of the signal can be calculated at step 570 from the last 2 terms (Q1 & Q2) at the end of the sampling period according to the following formula:

$$P=\sqrt{Q_1^2+Q_2^2-KQ_1Q_2}$$

At this point, the calculation of the power output can be normalized by dividing P by the number of measurements taken at step 572.

As explained below, processing of the signal depends on measurement of the actual linear power. Without these modifications, the output is not linear and is also dependent on the number of samples. The number of samples is a configurable parameter and is not the same for all channels in all signal detectors.

Figure 29:
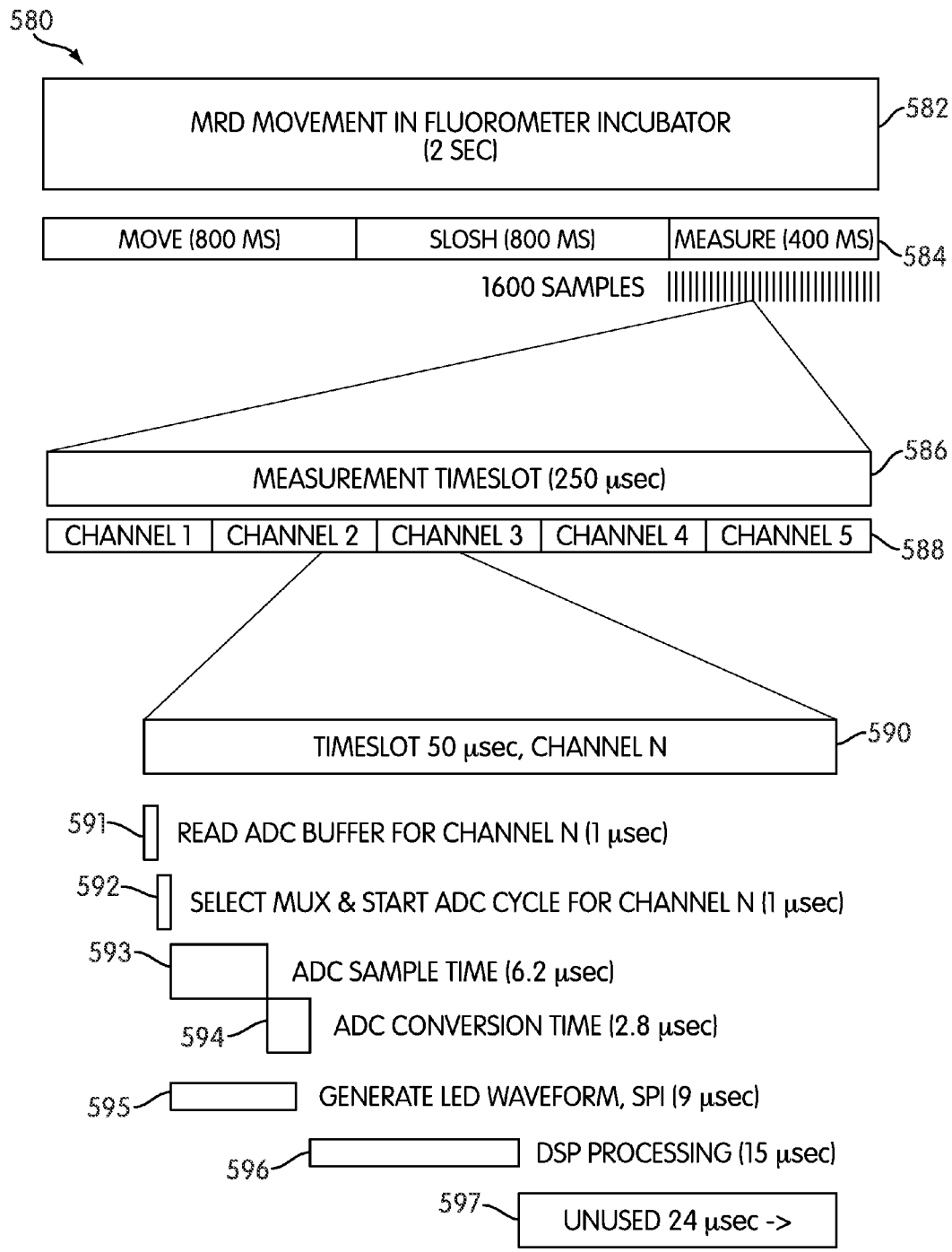
FIG. 29 is scheduling diagram showing movement of reaction receptacles, measurement of emission signals from the reaction receptacles, and processing of the signals measured from the reaction receptacles.

FIG. 29 is a timing diagram 580 of the movement of the MRD 160 by the carrier 242 and MRD interaction with each detector 400. As can be seen, the total MRD movement time 582 (e.g., 2 seconds) for each detector 400 is divided into several components. Referring to the timing blocks indicated at 584, according to some embodiments, a period (e.g., 0.8 second (800 msec)) is specified for moving the receptacle carrier 242 to place the MRD 160 in an operative position with respect to the signal detector 400, a slosh period (e.g., 0.8 second (800 msec)) is specified, and a measurement period (e.g., 400 ms) is specified. The slosh time delay is provided to allow the fluid within the receptacle 162 to stop sloshing (following the starting and stopping of the receptacle carrier 242) and to allow any mechanical vibrations to damp out before an emission signal measurement is taken. The measurement period is divided into measurement timeslots 586 of 250 μsec duration, and each timeslot is subdivided into 50 μsec timeslots 588 for each of the five channels of the signal detector 400 corresponding to the five receptacles 162 of the MRD 160. Thus, each of the channels is sampled every 250 μsec during the 400 ms measurement period, resulting in 1600 samples (0.400/0.00025). These 1600 samples are averaged to provide a single data point for the 400 ms measurement period.

The times are configurable. For example, a 700 ms slosh period and a 200 ms measurement period may be used. A 200 ms measurement period would result in 800 samples for a 250 μsec measurement timeslot, and the 800 samples would be averaged to provide a measurement data point for the 200 ms measurement period.

Each 50 μsec timeslot 590 for each channel N is divided into different tasks. During an initial time period 591 (e.g., 1 μsec) the detector 400 reads an analog to digital converter ("ADC") buffer to get the result of the previous A/D conversion. More specifically, during each 50 μsec timeslot 590, a different channel is sampled: channel 1 (i.e., a first receptacle vessel 162, See FIG. 1) is sampled during one 50 μsec timeslot 590, then channel 2 is sampled during the next 50 μsec timeslot 590, then channel 3 is sampled during the next 50 μsec timeslot 590, then channel 4 is sampled during the next 50 μsec timeslot 590, and then channel 5 is sampled during the next 50 μsec timeslot 590. In each 50 μsec time slot, one of the channels is sampled and one of the channels is processed. So, for example, when sampling channel 2, channel 1 is processed, when sampling channel 3, channel 2 is processed, then channels 4 and 3, then channels 5 and 4, then channels 1 and 5, etc. As explained above, for each channel, the signal detector converts photons to an analog voltage, and that voltage is digitized by the A/D converter. The digitized voltage is temporarily stored in the ADC buffer. As the signal detector begins the process for measuring the optical signal (and converting the signal to digital data), the digital value for the previous channel that is stored in the ADC buffer is read from the buffer and the value from the previous channel will be replaced in the ADC buffer by the value derived for the next channel.

This parallel sampling and processing saves time. The data previously converted for the previous channel is read, and then a conversion on currently measured data of the next channel begins. While the A/D conversion of the voltage analog corresponding to the detected optical signals proceeds on the present channel, data from the previous conversion and the previous channel, which was read from the ADC buffer, is processed by DSP to identify the component having the correct excitation frequency. Thus, processing and measurement overlap.

Returning to FIG. 29, during a subsequent time period 592 (e.g., 1 μsec) after reading the ADC buffer, the correct channel N is multiplexed, or activated, and the A/D cycle begins for that channel. There is an analog multiplexer that enables selection of one of N analog signals to be routed to the input of the A/D converter. This step selects one of the five channels in the signal detector 400 (since there is one channel for each receptacle 162 of the MRD 160 in each color) and starts an analog to digital conversion on that channel. The signal is measured by a two-step process. During the sampling time, block 593 (e.g., 6.2 pee), the analog signal is connected by the multiplexer to a sample and hold amplifier. The sampling time is necessary for the sample and hold amplifier to settle to an accurate representation of the analog signal. After the sampling time, the A/D conversion is started, block 594 (e.g., 2.8 pee). During conversion, the analog signal is disconnected from the sample and hold amplifier, and the voltage stored by the sample and hold amplifier is converted into digital bits by the A/D convertor. Thus, the signal measured during sampling time slot 593 is converted to a digital measurement of voltage during the conversion time slot 594 and is stored in the ADC buffer register, replacing the previously-stored value, which is then read in the beginning of the next 50 μsec time slot The processor calculates a digital value which is a representation of the next current data point in the LED current waveform. In parallel with time blocks 593 and 594, during time block 595 (e.g., 9 μsec), the next LED current data point in the AC waveform can be sent to a digital to analog converter ("DAC") using, for instance, a serial peripheral interface (SPI) for generating the excitation signal point for the channel N. The current waveform can be a sine wave, square wave, or other shape. This is configurable and both sine and square waves have been used with similar performance.

During time block 596 (e.g., 15 μsec), the digital signal processing ("DSP") (using, for instance, the modified Goertzel algorithm described above) is performed to calculate the power from the data read from the ADC buffer during time block 591.

According to some embodiments of the invention, a time block 597 (e.g., 24 pee) may be unused during each channel's 50 μsec timeslot, which may be used for performing other tasks.

Figure 21:
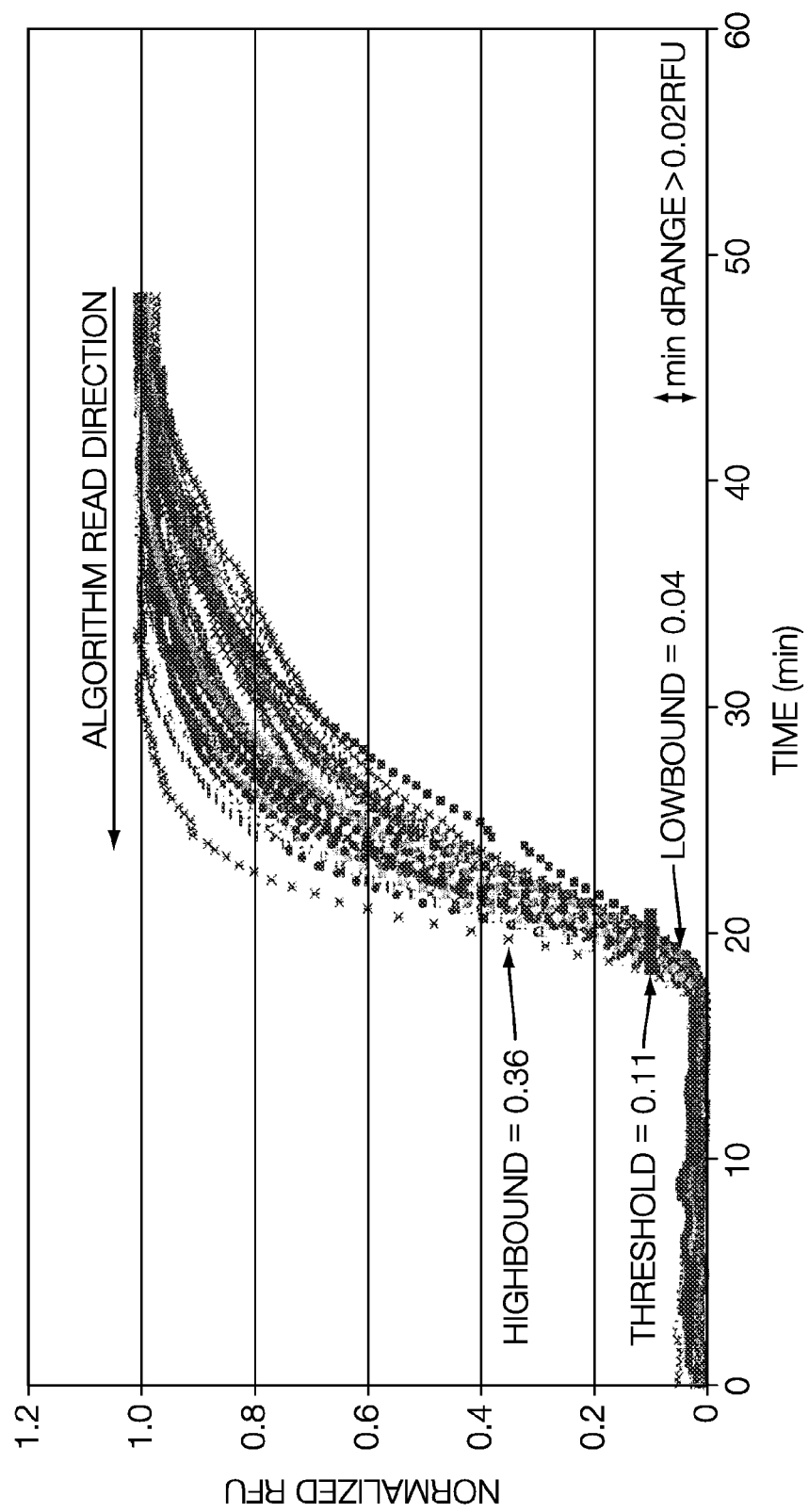
FIG. 21 is a time plot of real-time fluorometer data.

Once the data has been collected by measuring fluorometric emissions from each receptacle at prescribed intervals for a prescribed period of time, the data is processed to determine the concentration of a particular analyte (e.g., target nucleic acid) in the sample. The measured data, that is, the measure signal, will be referred to in terms of a Relative Fluorescent Unit ("RFU"), which is the signal generated by the detection PCB 422 of the signal detector 400 based on the amount of emission fluorescence focused onto the detection element 423. Each data point, measured at a given time interval, is RFU(t). Plots of RFU(t) for a variety of data sets, known as "growth curves" are shown in FIG. 21. In general, each RFU(t) plot is generally sigmoidal in shape, characterized by an initial, flat portion (known as the "static level" or "baseline phase") at or near a minimum level, followed by an abrupt and relatively steeply sloped portion (known as the "growth phase"), and ending with a generally flat portion at or near a maximum level (known as the "plateau phase").

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement—RFU (y-axis). Some, but not all, growth curves have a sigmoid-shape. The "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero. The "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease. The "plateau phase" refers to the final phase of the curve. In the plateau phase, the rate of measurable product formation is substantially lower than the rate of amplicon production in the log-linear growth phase, and may even approach zero.

Figure 20:
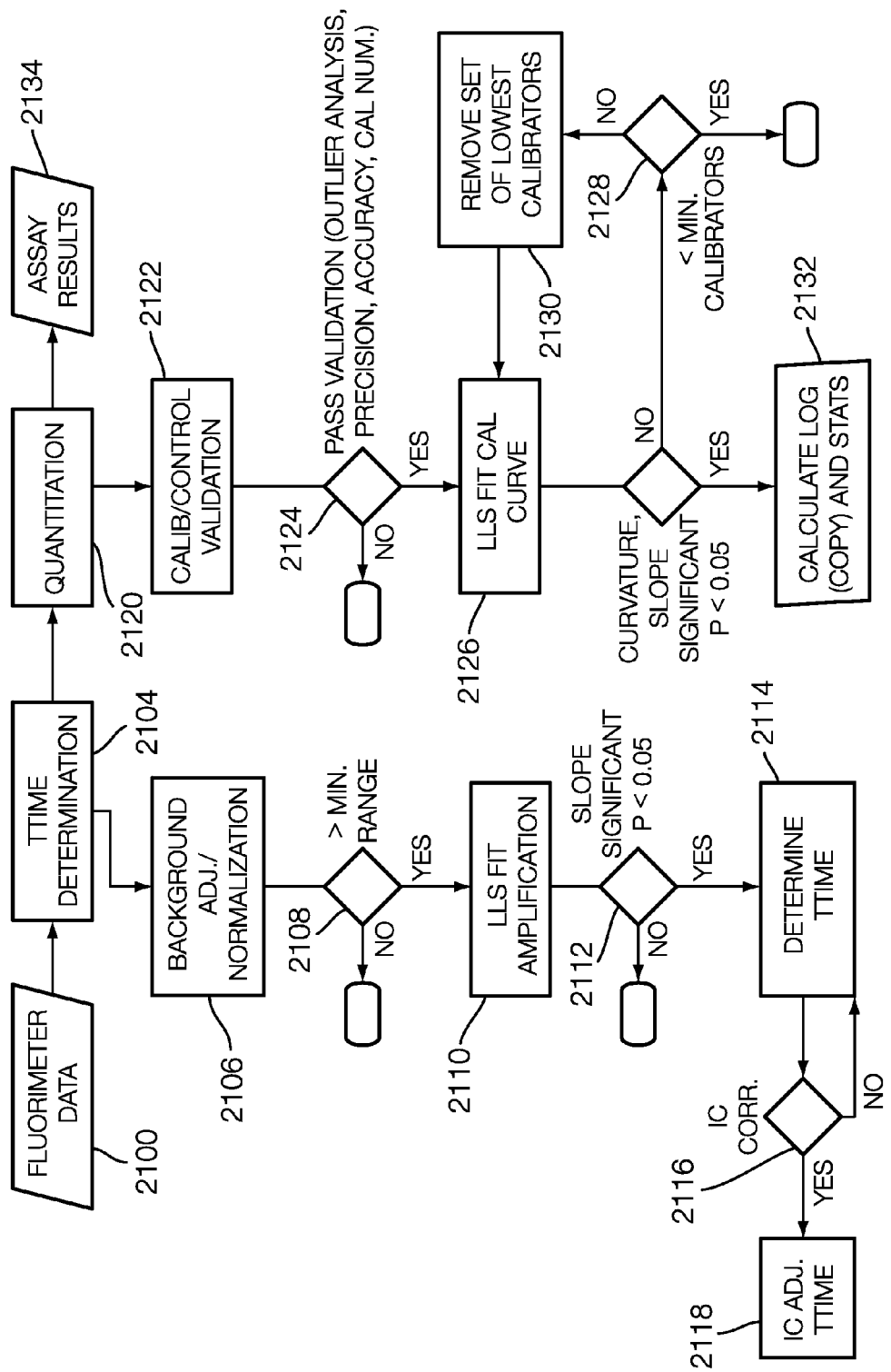
FIG. 20 is a flow chart showing an analyte quantification process.

A process for calculating an analyte concentration is shown by means of a flow chart in FIG. 20. The RFU(t) data from the signal detector 400 is input as represented at box 2100. The RFU(t) data is demodulated by the detector 400, for example, using the Goertzel algorithm described above. The RFU(t) data goes to threshold time determination, which begins at 2104. Threshold time, or T-time, (also known as time of emergence) refers to the time at which the data RFU(t), normalized as discussed below, reaches a predefined threshold value. Using calibration curves, as will be described in more detail below, the T-time determined for a particular sample can be correlated with an analyte concentration, thereby indicating the analyte concentration for the sample. In general, the higher the concentration of the analyte of interest, the sooner the T-time is reached.

The first step of the T-time determination procedure is background adjustment and normalization of the data, as represented at box 2106. Background adjustment is performed to subtract that portion of the signal data RFU(t) that is due to background "noise" from, for example, stray electromagnetic signals. That is, the background noise includes that part of the RFU(t) signal due to sources other than the analyte of interest. Background adjustment is performed by subtracting a background value "BG" from the data RFU(t) to obtain adjusted data RFU*(t). That is, RFU*(t)=RFU(t)−BG.

The background BG can be determined in a number of ways.

In accordance with one method for determining the background noise, the first step is to determine the time intervals between data points. The time interval is determined by multiplying cycle time (i.e., the time between consecutive data measurements) by the data point (i.e., $0^{th}$ data point, $1^{st}$ data point, $2^{nd}$ data point, ..., $n^{th}$ data point) and divide by 60 seconds. For example, assuming a cycle time of 30 seconds, the time interval for the $15^{th}$ data point is (15×30 sec.)/60 sec.=7.5.

The next step is to find the midpoint of the signal data by adding the minimum signal data point and the maximum signal data point and dividing by two. That is: $(RFU_{max}+RFU_{min})/2$ Starting at the time corresponding to the midpoint value and working backwards, calculate the slope for each pair of data points: $(RFU(t)-RFU(t-1))/\Delta t(t \rightarrow t-1)$.

Next, determine where the slope of RFU(t) flattens out by finding the first slope value that is less than the static slope value (i.e., the value before the RFU(t) curve begins its upward slope). A representative static slope value, also known as the "delta value," includes 0.0001. Once this slope is found, find the next cycle in which the slope that is not negative or is, for example, above the negative delta value (i.e., −0.0001); this value is $H_{index}$. Next, take the mean of the entire range of RFU(t) values starting at the first data point and go to the RFU value that corresponds to the $H_{index}$ value. The mean of this data may be computed using the Excel TRIMMEAN function on this range of data using a static back trim value of 0.15 (that is, the lowest 7.5% of RFU values in the specified range and the highest 7.5% RFU values in the specified range are excluded). This mean value is the background, BG. Alternatively, the background can be determined in accordance with the procedure described above using a delta value other than 0.0001.

A further alternative method for determining the background eliminates the delta value criterion and instead take a TRIMMEAN mean of the RFU data from cycle 1 to a prescribed end point, such as the first cycle before 5.5 minutes. For this alternative, the static back trim value may be adjusted to, for example, 0.40 (that is, the lowest 20% of RFU values in the specified range and the highest 20% RFU values in the specified range are excluded from the background calculation).

A further alternative method for determining the background is to perform a curve fit on all or a portion of the RFU data to derive an estimate of the baseline value, which is the background to be subtracted. Any curve fit technique suitable for fitting a curve to the RFU data can be used.

An exemplary curve fit technique is to use a portion of the equation derived by Weusten et al. for curve fit of the typically sigmoidal curves associated with nucleic acid amplification. See Weusten et al., Nucleic Acids Research, 30(6e26):1-7 (2002), the disclosure of which is incorporated by reference. For background subtraction, it is only necessary to ascertain the baseline level. Thus, it is also only necessary to fit a curve to the first portion of the RFU data encompassing the baseline, usually toward the beginning of the curve.

The curve fit may be performed on the RFU(t) data from cycle 1 to the cycle just before 75% of the maximum RFU. The following polynomial equation (3), which, as mentioned above, is a portion of the equation derived by Weusten et al, is used to generate a best fit model of the RFU data:

$$RFU(t)=Y0+a1a2[e^{a2(t-a3)}/(1+e^{a2(t-a3)})]\ln(1+e^{a2(t-a3)}) \quad (3)$$

Initial estimates for the variables Y0, a1, a2, and a3, as discussed below, are input to the curve-fit equation and an iterative solution fitting the equation to the RFU data is performed, for example, using the SOLVER function of Microsoft EXCEL, to yield the final equation and the final values for Y0, a1, a2, and a3.

Y0=is the baseline; an initial value can be RFU(1).

a1=relates to the steep portion (growth phase) of the RFU(t) data; 0.05 can be a suitable initial estimate for a1.

a2=relates to the steep portion (growth phase) of the RFU(t) data; 1.0 can be a suitable initial estimate for a2.

a3=relates to the transition between the baseline and the slope feature; the time, or cycle, at which RFU(t) reaches a value just before 25% of $RFU_{max}$ is a suitable initial estimate for a3.

When the final values of Y0, a1, a2, and a3 have been derived, Y0 is treated as the back ground, and is subtracted from the RFU(t) data for which the curve fit was performed.

Curve fit equations other than that described above can be used. For example, the commercially available TABLECURVE software package (SYSTAT Software Inc.; Richmond, Calif.) can be used to identify and select equations that describe exemplary real-time nucleic acid amplification curves. One such exemplary resulting equation, used for mathematical modeling, is given by equation (4):

$$RFU(t)=Y0+b(1-\exp(-(t-d*\ln(1-2^{-(-1/e)})-c)/d))^{-e} \quad (4)$$

Still another exemplary resulting equation is given by equation (5):

$$RFU(t)=Y0+b(1-\exp(-(t-d*\ln(2^{-(1/e)}-1)-c)/d))^{-e} \quad (5)$$

In each case, as described above, the equation can be solved, for example, using the SOLVER function of Microsoft EXCEL, to yield the final equation and the final values for Y0 and the other parameters, and the solutions yields a Y0 that is the background to be subtracted from the RFU(t) data.

To normalize the data, each data point, adjusted for the background, is divided by the maximum data point, also adjusted for the background. That is:

$$\text{Normalized } RFU = RFU_n(t)$$
$$= \frac{RFU^*(t)}{RFU^*_{max}}$$
$$= \frac{(RFU(t) - BG)}{(RFU_{max} - BG)}$$

Thus, the $RFU_n(t)$ will be from −1 to 1.

In step 2108, the range of data is calculated by subtracting $RFU_{n(min)}$ from $RFU_{n(max)}$. If the calculated range does not meet or exceed a specified, minimum range (e.g., 0.05), the data is considered suspect and of questionable reliability, and, thus, the T-time will not be calculated. The minimum range is determined empirically and may vary from one fluorescence measuring instrument to the next. Ideally, the specified minimum range is selected to ensure that the variation of data values from minimum to maximum exceeds the noise of the system.

In step 2110, a curve fit procedure is applied to the normalized, background-adjusted data. Although any of the well-known curve fit methodologies may be employed, in a preferred embodiment, a linear least squares ("LLS") curve fit is employed. The curve fit is performed for only a portion of the data between a predetermined low bound and high bound. The ultimate goal, after finding the curve that fits the data, is to find the time corresponding to the point at which the curve intersects a predefined threshold value. In the preferred embodiment, the threshold for normalized data is 0.11. The high and low bounds are determined empirically by fitting curves to a variety of control data sets and observing the time at which the various curves cross the chosen threshold. The high and low bounds define the upper and lower ends, respectively, of the range of data over which the curves exhibit the least variability in the times at which the curves cross the given threshold value. In the preferred embodiment, the low bound is 0.04 and the high bound is 0.36—See FIG. 21. The curve is fit for data extending from the first data point below the low bound through the first data point past the high bound.

At step 2110, determine whether the slope of the fit is statistically significant. For example, if the p value of the first order coefficient is less than 0.05, the fit is considered significant, and processing continues. If not, processing stops. Alternatively, the validity of the data can be determined by the R2 value.

The slope m and intercept b of the linear curve y=mx+b are determined for the fitted curve. With that information, T-time can be determined at step 2104 as follows:

$$T\text{-time} = \frac{\text{Threshold} - b}{m}$$

Figure 22:
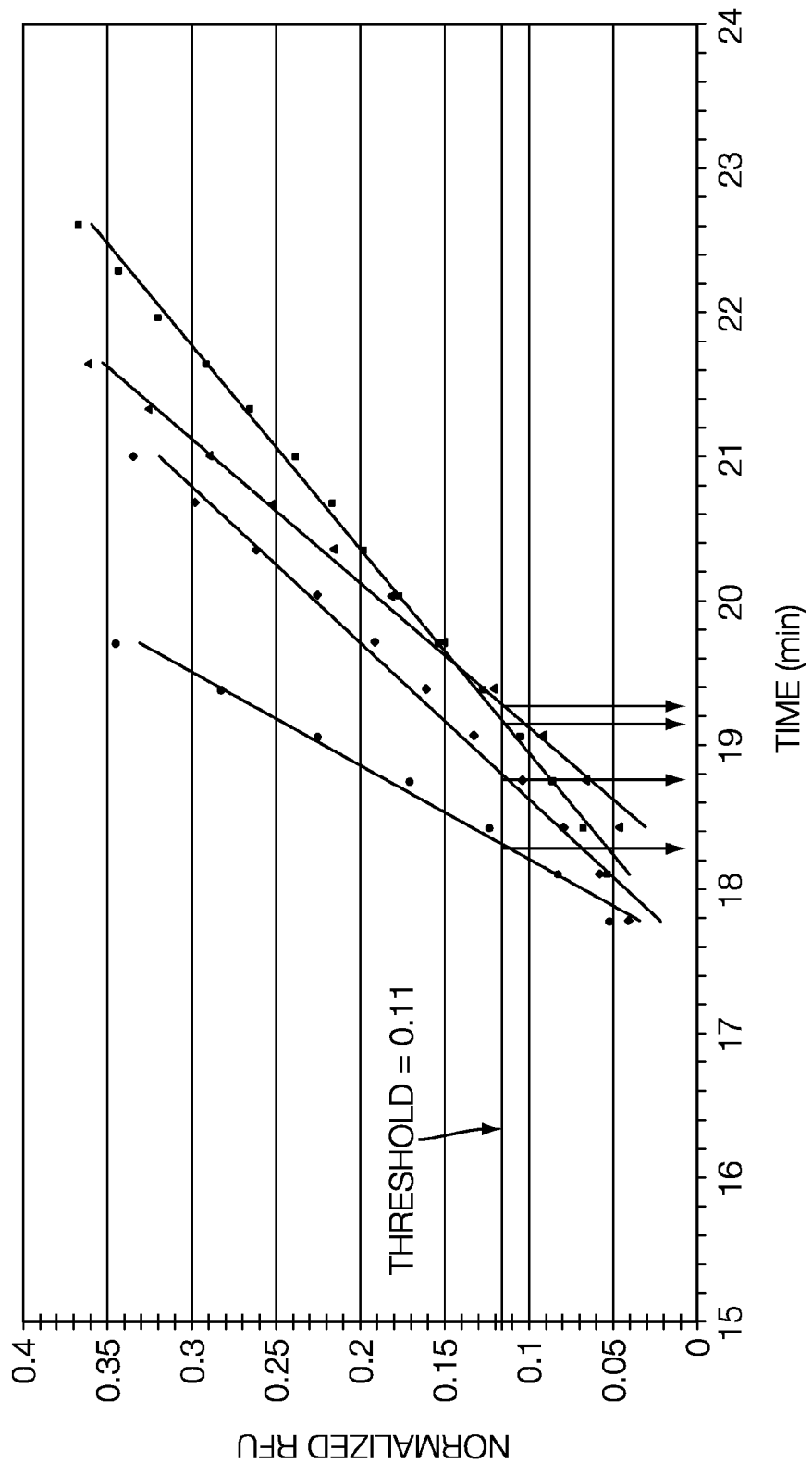
FIG. 22 is a plot showing a method for fitting a curve to real-time fluorometer data and using the fit to determine a threshold time.

The technique of using the fitted curve to determine T-times is illustrated graphically in FIG. 22.

Returning to FIG. 20, at step 2116, it is determined whether or not internal control/calibrator adjustments are desired. Typically, a test procedure would include at least one reaction vessel with a known concentration of a nucleic acid (other than a nucleic acid of interest) as a control, or, alternatively, a control nucleic acid sequence can be added to each sample. The known concentration can be simply used as control to confirm that a reaction did take place in the reaction vessel. That is, if the known concentration is amplified as expected, successful reaction is confirmed and a negative result with respect to the target analyte is concluded to be due to absence of target in the sample. On the other hand, failure to amplify the known concentration as expected indicates a failure of the reaction and any result with respect to the target is ignored.

The known concentration can be used to calibrate the concentration of the target. The T-times corresponding to a series of standards containing internal control and target sequences are determined for a statistically valid number of data sets. Using this data, a calibration plot is constructed from which the test sample's concentration is interpolated as described below.

One method of constructing the calibration plot places the known concentrations of target analyte on the x-axis versus the difference between target and control T-times on the y-axis. Subsequently, the test sample's concentration is interpolated from the calibration curve fit. Another method of constructing the calibration plot places the known concentration of target analyte on the x-axis versus the fraction (target T-time/internal control T-time) on the y-axis. Subsequently, the test sample's concentration is interpolated from the calibration curve fit. An example of this is disclosed in Haaland, et al., "Methods, Apparatus and Computer Program Products for Determining Quantities of Nucleic Acid Sequences in Samples Using Standard Curves and Amplification Ratio Estimates," U.S. Pat. No. 6,066,458, the disclosure of each of which is incorporated by reference. A further alternative method of constructing the calibration plot utilizes a parametric calibration method, such as the method described in Carrick et al., "Parametric Calibration Method," U.S. Pat. No. 7,831,417, the disclosure of which is incorporated by reference.

Occasionally, data sets exhibit a dip just after the initial static baseline (i.e., the initial, flat part of the RFU(t) curve, see FIG. 21) and just before the data begins its upward slope. To identify and correct such data, and prior to determining the T-time for that data, the following algorithm is employed. Starting at Hindex, check each RFU(t) value to determine if it is less than the background value, BG. If yes, subtract RFU(t) from BG (the result should be a positive number). This will be the CorValue. Add the CorValue to the background subtracted value, this in turn will bring RFU(t) up to the baseline. Perform this analysis working forward on each RFU(t) value until the latest CorValue is less than the preceding CorValue. Add the greatest CorValue to each of the remaining background subtracted RFU(t) values. Now, the corrected data set can be normalized and the T-time determined as described above.

If a curve fit method is used to derive the background level, it may not be necessary to perform the dip correction described above. It may also be desirable to perform outlier detection on the data set to identify and, if necessary, discard data points that exhibit abnormal values as compared to the remaining data points. Any of the well-known outlier detection methodologies can be used.

The quantitation procedure 2120 is the second part of the analyte concentration determination. T-times are determined for known concentrations of analytes for known conditions. Using this data, relationships between analyte concentrations (typically expressed as log copy) and T-times can be derived. After a T-time is determined for a particular sample, the derived relationship (Log copy=f (T-time)) can be used to determine the analyte concentration for the sample.

More specifically, at steps 2122 and 2124, calibration/control data sets for a control analyte of known concentrations are validated by, for example, outlier analysis and/or any other known data validation methodologies. If the data is found to be valid, calibration continues, otherwise, calibration stops.

T-times for the control data sets are determined, and T-time vs. Log copy is plotted for all samples of a particular condition (e.g., samples processed with reagents from a particular batch lot). In step 2126, a curve fit, such as a linear least squares fit, is performed on a portion of the T-time vs. Log copy plot to find the slope m and intercept b of the line that best fits the data. If the number of available T-time vs. Log copy data points (known as "calibrators") is not less than a predefined minimum number of calibrators (as determined at step 2128), lowest calibrators, if any, are removed at step 2130, as follows:

After finding the best fit line for the calibrator data points, $2^{nd}$ and $3^{rd}$ order curve fits are tested as well. If these fits are significantly better than the 1st order, linear fit, the calibrator data point that is furthest from the linear curve fit is discarded, and $1^{st}$, $2^{nd}$, and $3^{rd}$ fits are found and compared again with the remaining calibrators. This process is repeated—assuming that the number of calibrators is not less than the minimum acceptable number of calibrators—until the 2nd and 3rd order fits are not significantly better than the $1^{st}$ order, linear fit.

When the linear T-time vs. Log copy equation has been derived, the concentration (as Log copy) of the analyte of interest for a sample is determined, at step 2132, by plugging the T-time for that sample into the equation. Thus, the assay results are obtained 2134.

Contemplated enhancements of the RT incubator 608 include self-checking optical detection modules. In such a module, a known, standard excitation signal is emitted by the LED 1732 (or, alternatively, a separate, dedicated LED) and the excitation light is directed to the photo diode 1780 (and/or a separate, dedicated comparator photo diode) to ensure that the excitation signals, emission signals, and the signal output of the printed circuit board 1790 are all correct.

All documents referred to herein are hereby incorporated by reference herein. No document, however, is admitted to be prior art to the claimed subject matter.

While the invention has been described in connection with what are presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

Furthermore, those of the appended claims which do not include language in the "means for performing a specified function" format permitted under 35 U.S.C. § 112(¶6), are not intended to be interpreted under 35 U.S.C. § 112(¶6) as being limited to the structure, material, or acts described in the present specification and their equivalents.

The invention claimed is:

1. A system for detecting an optical signal emitted from a receptacle, said system comprising:
   an excitation source controlled by an excitation circuit to (a) generate an optical excitation signal having a predetermined excitation wavelength that excites an emission moiety which emits an optical emission signal that is associated with the excitation wavelength and has a predetermined emission wavelength and (b) modulate the optical excitation signal at a predetermined modulation frequency;
   excitation optics configured to direct the optical excitation signal at the receptacle;
   a detector circuit including a photodetector configured to detect an optical signal including an optical emission signal emitted from the receptacle and to convert the detected optical signal to an analog detection signal; and
   a controller directly or indirectly connected to the detector circuit and programmed with a signal-digitizing algorithm to digitize the analog detection signal and generate digitized detection data;
   wherein the controller is further programmed with a digital signal-processing algorithm for determining from the digitized detection data an amplitude of the optical emission signal at the predetermined modulation frequency to thereby ascertain the portion of the detected optical signal corresponding to the associated optical emission signal.

2. The system of claim 1, further comprising a processor programmed with a signal-processing algorithm for determining the amount of an analyte present within the receptacle based on data relating to the portion of the detected optical signal corresponding to the associated optical emission signal.

3. The system of claim 1, further comprising:
   a plurality of excitation sources in fixed positions with respect to each other, each excitation source being controlled by an excitation circuit to (a) generate an optical excitation signal having a predetermined excitation wavelength that excites an emission moiety that emits an associated optical emission signal having a predetermined emission wavelength and (b) modulate the optical excitation signal at a predetermined modulation frequency;
   excitation optics configured to direct each optical excitation signal at a different receptacle; and
   a plurality of detector circuits including photodetectors in fixed positions with respect to each other, each detector circuit being configured to detect an optical signal including an optical emission signal emitted from a receptacle and to convert the detected optical signal to an analog detection signal,
   wherein each excitation source corresponds with an associated detector circuit such that the generated optical excitation signal and the detected optical signal of each associated excitation source and detector circuit are directed at, and emitted from, an associated receptacle,
   wherein the controller is configured to digitize the analog detection signal associated with each detector circuit and generate digitized detection data; and
   wherein the controller is configured to determine from the digitized detection data associated with each detector circuit an amplitude of the emission signal at the associated predetermined modulation frequency and to ascertain the portion of the associated detected optical signal that corresponds to the associated optical emission signal.

4. The system of claim 3, wherein the different associated receptacles comprise a plurality of receptacles arranged in a linear, side-by-side arrangement and wherein the associated predetermined modulation frequencies for adjacent receptacles are different.

5. The system of claim 4, wherein each receptacle is releasably fixed within the side-by-side arrangement.

6. The system of claim 4, wherein the associated predetermined modulation frequencies for alternate receptacles are the same.

7. The system of claim 3, further comprising a receptacle moving apparatus constructed and arranged to move the different associated receptacles relative to the plurality of excitation sources and photodetectors.

8. The system of claim 3, comprising two or more sets of the plurality of excitation sources and associated photodetectors, wherein each set is spatially distinct from each other set within the system.

9. The system of claim 8, comprising three to six sets of the plurality of excitation sources and associated photodetectors.

10. The system of claim 8, wherein each set of the plurality of excitation sources and associated photodetectors is arranged radially around a central axis.

* * * * *